(12) United States Patent
Diwan

(10) Patent No.: US 12,128,200 B2
(45) Date of Patent: *Oct. 29, 2024

(54) EAR CLEANING DEVICES AND METHODS

(71) Applicant: SafKan, Inc., Renton, WA (US)

(72) Inventor: Aadil Diwan, Renton, WA (US)

(73) Assignee: SafKan, Inc., Redmond, WA (US)

( * ) Notice: Subject to any disclaimer, the term of this patent is extended or adjusted under 35 U.S.C. 154(b) by 585 days.

This patent is subject to a terminal disclaimer.

(21) Appl. No.: 17/068,242

(22) Filed: Oct. 12, 2020

(65) Prior Publication Data

US 2021/0268168 A1 Sep. 2, 2021

Related U.S. Application Data

(63) Continuation of application No. 16/577,986, filed on Sep. 20, 2019, now Pat. No. 10,799,629, which is a
(Continued)

(51) Int. Cl.
*A61M 3/02* (2006.01)
*A61M 1/00* (2006.01)
*A61F 11/00* (2022.01)

(52) U.S. Cl.
CPC ............ *A61M 3/0287* (2013.01); *A61M 1/77* (2021.05); *A61M 3/0275* (2013.01);
(Continued)

(58) Field of Classification Search
CPC ......... A61F 11/006; A61M 2210/0662; A61M 2205/502; A61M 3/022; A61M 16/0683;
(Continued)

(56) References Cited

U.S. PATENT DOCUMENTS 4,201,212 A   5/1980  Bradley
5,364,343 A * 11/1994 Apolet ................ A61M 3/0283
                                                    604/35
(Continued)

FOREIGN PATENT DOCUMENTS

CH          702267 A2    5/2011
CN        201320359 Y   10/2009
(Continued)

OTHER PUBLICATIONS

Australian Office Action for Application No. AU2017289488 dated Jul. 7, 2022, 3 pages.
(Continued)

*Primary Examiner* — Brandy S Lee
(74) *Attorney, Agent, or Firm* — COOLEY LLP

(57) ABSTRACT

A system and method to irrigate a user's auditory canal. A fluid can be dispensed from a reservoir through a fluid path and out through openings of a delivery element into the auditory canal. A pump may be used to facilitate the process of dispensing the fluid. The fluid can be delivered to the user's auditory canal for a predetermined period of time. Such a time period may be user selectable. The discharge from the irrigation is removed from the user's auditory canal via a discharge port located on the delivery element. The discharge exits the delivery element and proceeds to a discharge reservoir via a discharge path. A vacuum may be used to generate a negative pressure to facilitate the removal of the discharge from the auditory canal.

19 Claims, 34 Drawing Sheets

Related U.S. Application Data continuation of application No. 16/235,469, filed on Dec. 28, 2018, now Pat. No. 10,420,877, which is a continuation-in-part of application No. PCT/US2017/027763, filed on Apr. 14, 2017.

(60) Provisional application No. 62/357,320, filed on Jun. 30, 2016.

(52) U.S. Cl.
CPC .......... *A61F 11/006* (2013.01); *A61M 3/0208* (2014.02); *A61M 3/0212* (2014.02); *A61M 3/022* (2014.02); *A61M 2205/502* (2013.01); *A61M 2209/088* (2013.01); *A61M 2210/0662* (2013.01)

(58) Field of Classification Search
CPC .............. A61M 1/77; A61M 2209/088; A61M 3/0208; A61M 3/0212; A61M 3/0275; A61M 3/0287
See application file for complete search history.

(56) References Cited

U.S. PATENT DOCUMENTS

| | | | |
|---|---|---|---|
| 5,685,851 | A | 11/1997 | Murphy et al. |
| 5,944,711 | A | 8/1999 | Pender |
| D453,376 | S | 2/2002 | McMahon et al. |
| D453,829 | S | 2/2002 | McMahon et al. |
| 6,458,094 | B1 | 10/2002 | McMahon et al. |
| D475,132 | S | 5/2003 | Randolph |
| D602,583 | S | 10/2009 | Pidgeon et al. |
| D602,584 | S | 10/2009 | Pidgeon et al. |
| 7,699,820 | B1 | 4/2010 | French |
| 8,187,236 | B1 | 5/2012 | French |
| 8,328,830 | B1 * | 12/2012 | Pandit ................. A61M 3/0208 606/162 |
| 8,603,152 | B2 * | 12/2013 | Smith ..................... A61F 7/007 607/113 |
| 8,840,546 | B2 | 9/2014 | Truong et al. |
| 9,713,710 | B2 | 7/2017 | Morriss et al. |
| 10,420,877 | B2 * | 9/2019 | Diwan .................... A61M 1/77 |
| 10,799,629 | B2 | 10/2020 | Diwan |
| 11,141,525 | B1 | 10/2021 | Zhang et al. |
| 2002/0173746 | A1 | 11/2002 | McMahon et al. |
| 2003/0130613 | A1 | 7/2003 | Harmon et al. |
| 2010/0016787 | A1 * | 1/2010 | Shapiro ............... A61M 3/0208 604/35 |
| 2010/0198135 | A1 | 8/2010 | Morriss et al. |
| 2010/0217296 | A1 | 8/2010 | Morriss et al. |
| 2011/0015489 | A1 | 1/2011 | Raghuprasad |
| 2011/0295073 | A1 | 12/2011 | Truong et al. |
| 2012/0302957 | A1 | 11/2012 | Vlodaver et al. |
| 2013/0338568 | A1 | 12/2013 | Mehta |
| 2019/0143029 | A1 | 5/2019 | Diwan |
| 2020/0009313 | A1 | 1/2020 | Diwan |

FOREIGN PATENT DOCUMENTS

| | | |
|---|---|---|
| CN | 201968023 U | 9/2011 |
| CN | 203195842 U | 9/2013 |
| CN | 204907265 U | 12/2015 |
| EP | 0099759 A2 | 2/1984 |
| EP | 3478233 B1 | 6/2021 |
| JP | 5932455 B2 | 6/2016 |
| WO | WO-8706456 A1 | 11/1987 |
| WO | WO-2005079564 A1 | 9/2005 |
| WO | WO-2018004785 A1 | 1/2018 |
| WO | WO-2018027102 A1 | 2/2018 |

OTHER PUBLICATIONS

Chinese Office Action for Application No. CN20178050222 dated Feb. 8, 2022, 20 pages.
Chinese Office Action for Application No. CN20178050222 dated Jul. 4, 2022, 5 pages.
European Search Report issued for 21178350.1, mailed on Jan. 27, 2022, 3 pages.
International Preliminary Report on Patentability for the International Application No. PCT/US2017/027763, mailed Jan. 1, 2019, 9 pages.
International Search Report and Written Opinion issued for the International Application No. PCT/US2017/027763, mailed Sep. 21, 2017, 11 pages.
Office Action for Australian Application No. 2017289488, mailed Aug. 12, 2022, 3 pages.
Office Action for Australian Application No. 2017289488, mailed Aug. 25, 2021, 7 pages.
Office Action for Canadian Application No. CA3029401 dated May 25, 2023, 3 pages.
Office Action for European Application No. EP20210178350 mailed Dec. 15, 2022, and received Dec. 15, 2022, 8 pages.
Office Action for Indian Application No. 201914054184 mailed Jan. 16, 2023, 5 pages.
Office Action for Japanese Application No. 2018-568928 mailed Jan. 25, 2021, 5 pages.
Office Action for Japanese Application No. 2018-568928 mailed Oct. 1, 2021, 5 pages.
Supplementary European Search Report issued for EP17820700, mailed on Jan. 15, 2020.

* cited by examiner

EAR CLEANING DEVICES AND METHODS

CROSS-REFERENCE TO RELATED APPLICATIONS

This application is a continuation of U.S. patent application Ser. No. 16/577,986, filed Sep. 20, 2019, titled "Ear Cleaning Devices and Methods," which is a continuation of U.S. patent application Ser. No. 16/235,469, filed Dec. 28, 2018, titled "Ear Cleaning Devices and Methods," which is a continuation-in-part application of International Application No. PCT/US2017/027763, filed Apr. 14, 2017, titled "Wearable Ear Cleaning Device," which claims priority to and the benefit of U.S. Provisional Patent Application No. 62/357,320, filed Jun. 30, 2016, titled "Wearable Ear Cleaning Device," the disclosures of each of these incorporated herein by reference.

TECHNICAL FIELD

The present disclosure relates generally to an ear cleaning device, and specifically to systems, devices, and methods for irrigating an ear canal of a subject.

BACKGROUND

Ear wax, also known as cerumen, naturally forms in the outer portion of a person's ear, and serves to protect and lubricate the ear canal or auditory canal. The motion of a person's jaw assists in moving old ear wax towards the outside of the auditory canal where it dries up and falls away. Unfortunately, ear wax may build up in the auditory canal to the point that it impacts a person's hearing. For example, built-up ear wax may accumulate at any point in or about the auditory canal, and at any point on or along a surface of the auditory canal. Some people may attempt to clean their ears with physical objects, such as cotton swabs, that can generally push ear wax deeper into the auditory canal towards the ear drum. For this reason, attempting to clean the auditory canal with such objects can actually harm a person's hearing without providing any substantial benefit. Due to the drawbacks of existing systems and methods, it is desirable to have a device for cleaning an ear of a person that effectively removes ear wax from the ear canal without such drawbacks.

SUMMARY

According to embodiments disclosed herein, a device to irrigate ear canals of human ears may include a first over-ear earpiece sized and dimensioned to be worn over human ears and having a cavity sized and dimensioned to receive one human ear, the first over-ear earpiece comprising: a first cleaning agent reservoir to hold cleaning agents; a first discharge collection reservoir to collect discharge from irrigation; a first cannula coupler interface to which cannulas are selectively detachably physically coupleable; a first cleaning fluid fluidly communicative path that provides fluid communication between the first cleaning agent reservoir and the first cannula coupler interface; and a first discharge fluidly communicative path that provides fluid communication between the first discharge collection reservoir and the first cannula coupler interface.

The device may further include a second over-ear earpiece sized and dimensioned to be worn over human ears and having a cavity sized and dimensioned to receive one human ear, the second over-ear earpiece comprising: a second cleaning agent reservoir to hold cleaning agents; a second discharge collection reservoir to collect discharge from irrigation; a second cannula coupler interface to which cannulas are selectively detachably physically coupleable; a second cleaning fluid fluidly communicative path that provides fluid communication between the second cleaning agent reservoir and the second cannula coupler interface; and a second discharge fluidly communicative path that provides fluid communication between the second discharge collection reservoir and the second cannula coupler interface.

The device may further include an adjustable head strap that adjustably connects the first over-ear earpiece and the second over-ear earpiece in spaced apart relation from one another, the adjustable head strap sized and dimensioned to be worn on a human head with the first over-ear earpiece positioned over a first ear and the second over-ear earpiece positioned over a second ear.

The device may further include at least a first pivot coupler that pivotally couples the first over-ear earpiece to the adjustable head strap to pivot about a first axis; and at least a second pivot coupler that pivotally couples the second over-ear earpiece to the adjustable head strap to pivot about a second axis, the first and the second axes perpendicular to an axis that extends between the respective cannula coupler interfaces of the first and the second over-ear earpieces.

The first cleaning agent reservoir may have a port, the first discharge collection reservoir may have a port, and the first over-ear earpiece may further include a first housing, the first housing comprises a pan and a lid which form an interior of the first housing, with a first passage that extends through the first housing and which is aligned with and sized and dimensioned to mate with the port of the first cleaning agent reservoir and a second passage that extends through the first housing and which is aligned with and sized and dimensioned to mate with the port of the first discharge collection reservoir, the interior of the first housing sealed from the first and the second passages.

The first over-ear earpiece may further include a first annular bracket, the first annular bracket pivotally coupled to the adjustable head strap, and the first housing selectively detachably coupled to the first annular bracket.

The first over-ear earpiece may further include a resilient or conformable annular membrane which at least partially forms the cavity sized and dimensioned to receive one ear.

The first over-ear earpiece may further include a first shell that forms the first cleaning agent reservoir and a second shell that forms the first discharge collection reservoir. The first discharge collection reservoir may be selectively detachable with respect to the first cleaning agent reservoir. The first cleaning agent reservoir may be selectively detachable with respect to the first discharge collection reservoir.

The first over-ear earpiece may further include a first cover that is detachable securable to the second shell and which forms the first discharge collection reservoir along with the second shell.

The first over-ear earpiece may further include a second cover that is detachably securable to the first shell and which forms the first cleaning agent reservoir along with the first shell.

The first over-ear earpiece may further include a first housing to which the first discharge collection reservoir and the first cleaning agent reservoir are selectively detachable.

The first over-ear earpiece may further include a first pair of ferromagnetic couplers that detachably magnetically couple the first cleaning reservoir to the first housing.

The first over-ear earpiece may further include a second pair of ferromagnetic couplers that detachably magnetically couple the first discharge collection reservoir to the first housing.

The first over-ear earpiece may further include at least one pump fluidly coupled to move cleaning agent along the first cleaning fluid fluidly communicative path from the cleaning agent reservoir toward the first cannula coupler interface.

The first over-ear earpiece may further include at least one pump fluidly coupled to apply a negative pressure to move discharge along the first discharge fluidly communicative path from the first cannula coupler interface toward the first discharge collection reservoir.

The first over-ear earpiece may further include a first housing, at least one pump fluidly coupled to at least one of the first cleaning fluid fluidly communicative path or the discharge fluidly communicative path, and a first set of controller circuitry housed in the first housing and communicatively coupled to control the at least one pump.

The first over-ear earpiece may further include a number of user-actable selectable controls accessible from an exterior of the first over-ear earpiece, the user-actable selectable controls communicatively coupled to the first set of controller circuitry communicatively coupled to control the at least one pump.

The first over-ear earpiece may further include a disposable cannula having a proximate end and a distal end, an irrigation inlet port positioned at the proximate end, a discharge collection outlet port positioned at the proximate end, a plurality of irrigation outlet apertures positioned relatively toward the distal end with respect to the irrigation inlet port, the irrigation outlet apertures in fluid communication with the irrigation inlet port, and a discharge collection inlet port positioned relatively toward the distal end with respect to the discharge collection outlet port, the discharge collection inlet port in fluid communication with the discharge collection outlet port.

The disposable cannula may further include a flow path that extends between the discharge collection inlet port and the discharge collection outlet port and a trap positioned in the flow path between the discharge collection inlet port and the discharge collection outlet port.

The device may further include a first processor, and a first nontransitory computer-readable medium communicatively coupled to the first processor, wherein the first nontransitory computer-readable medium stores first processor-executable instructions that specifically program the first processor to: provide a number of signals to at least one pump that causes the at least one pump to dispense a first quantity of cleaning fluid along the first cleaning fluid fluidly communicative path from the first cleaning agent reservoir and to produce a negative pressure along at least a portion of the first discharge fluidly communicative path. The first processor-executable instructions may specifically program the first processor to time-delay the production of the negative pressure from the dispensation of the first quantity of cleaning fluid for a first period of time. The first processor-executable instructions may specifically program the first processor to time-delay the production of the negative pressure from the dispensation of the first quantity of cleaning fluid for at least one minute.

According to embodiments disclosed herein, a cannula may be summarized as including a body, the body having a length, a proximate end, and a distal end, the distal end opposite the proximal end across the length of the body, the body additionally having an irrigation inlet port positioned at the proximal end, a discharge collection outlet port positioned at the proximal end, a plurality of irrigation outlet apertures positioned relatively toward the distal end with respect to the irrigation inlet port, and a discharge collection inlet port positioned at the distal end, the body further having at least one irrigation passage that provides at least one irrigation flow path between the irrigation inlet port and the plurality of irrigation outlet apertures, at least one discharge collection passage that provides at least one discharge flow path that extends between the discharge collection inlet port and the discharge collection outlet port, and at least one trap positioned in the discharge passage between the discharge collection inlet port and the discharge collection outlet port in the at least one discharge flow path.

The body may further include an interface sized and dimensioned to removably physically couple to a complementary interface of an over-ear earpiece and to align the irrigation inlet port of the cannula with a cleaning agent port of the over-ear earpiece and to concurrently align the discharge collection outlet port with a vacuum port of the over-ear earpiece when the cannula is physically coupled to the over-ear earpiece. The at least one trap may be a filter that extends at least partially across the discharge collection passage. The discharge collection passage may have an inside perimeter, wherein the at least one trap may include a plurality of projections that extend radially inward from the inside perimeter of the discharge collection passage towards a central axis of the discharge collection passage. The at least one trap may be sized and dimensioned to trap physical debris of at least one defined dimension while passing at least one of a quantity of a liquid and air. The plurality of irrigation outlet apertures may include at least three irrigation outlet apertures proximate the distal end. At least one of the at least three irrigation outlet apertures may be sized and shaped to direct a flow of cleaning agent that exits the at least one of the at least three irrigation outlet apertures radially outward from the distal end of the cannula. The proximal end may have a respective cross-sectional area, the distal end may have a respective cross-sectional area and the cross-sectional area of the distal end may be less than the cross-sectional area of the proximal end, and the body of the cannula may taper from the proximal end towards the distal end. The tapered body may be sized and shaped such that as the cannula is inserted into a human auditory canal that has a side wall and leads to an ear drum, a portion of the body of the cannula impacts the side wall of the human auditory canal before the distal end of the cannula impacts the ear drum. The body of the cannula may form a frustro-conical shape and the distal end may include a beveled portion. The proximal end may include an interior wall with an outside diameter and an exterior wall with an interior diameter, and the interior wall and the exterior wall may be sized and shaped to removably securely engage a complementary interface of an over-ear earpiece between the outside diameter of the interior wall and the interior diameter of the exterior wall. The body may be a unitary single-piece plastic body and may have a form that is a body of rotation. The irrigation inlet port may be radially offset from the discharge collection outlet port. The body may have a central/longitudinal axis and the discharge collection inlet port may be disposed about the central/longitudinal axis. The body may have a central/longitudinal axis and the irrigation outlet apertures may be radially offset outwardly from the central/longitudinal axis.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

As noted above, ear wax, also known as cerumen, naturally forms in the outer portion of a person's auditory canal, and serves to protect and lubricate the auditory canal. In some cases, ear wax may build up in the auditory canal to the point that the ear wax can impact a person's hearing. Moreover, objects inserted into the auditory canal (e.g., cotton swabs, fingers) can push ear wax deeper into the auditory canal towards the ear drum, which can further negatively impact a person's hearing.

To clean the auditory canal with reduced risk of harming a person's hearing, physicians have developed ear cleaning techniques in which a mixture of saline, hydrogen peroxide, and/or water is used to irrigate the auditory canal and remove an excessive build-up of ear wax. In some cases, irrigating the auditory canal by way of such techniques may, however, require a visit to a physician and the use of devices that require multiple people to operate. In addition, such devices and techniques that are used to irrigate the auditory canal may result in used cleaning agent or cleaning fluid, usually carrying flushed ear wax, to exit the auditory canal and impact the patient (e.g., by contact of [ ] with the patient). After a cleaning procedure, a physician or other individual needs to clean a surrounding area and/or components used to collect used cleaning agent or flushed ear wax. Accordingly, it can be desirable to have a system for cleaning an auditory canal that overcomes the aforementioned problems, which can be operable by a single user, to safely and effectively clean the auditory canal, e.g., by irrigation and removal of excessive ear wax.

Embodiments of the present disclosure are directed to an ear irrigation and cleaning device and system. The ear cleaning device and system can be operable by a single user to safely and effectively clean an auditory canal by irrigation and removal of excessive ear wax.

The ear of a user, patient, or subject includes an auricle and an auditory or ear canal (collectively, e.g., "outer ear", "external ear", etc.). The auricle is a visible portion of the ear residing on an outside of the user's head. The ear canal includes a portion of the ear extending inwardly from the auricle towards an eardrum ("eardrum" or "tympanic membrane") to connect the eardrum to the auricle. Ear wax can build up or accumulate along a surface of the auricle and/or the ear canal. Systems, devices, and methods described herein facilitate the removal and/or cleaning of ear wax from a subject's ear.

Figure 1:
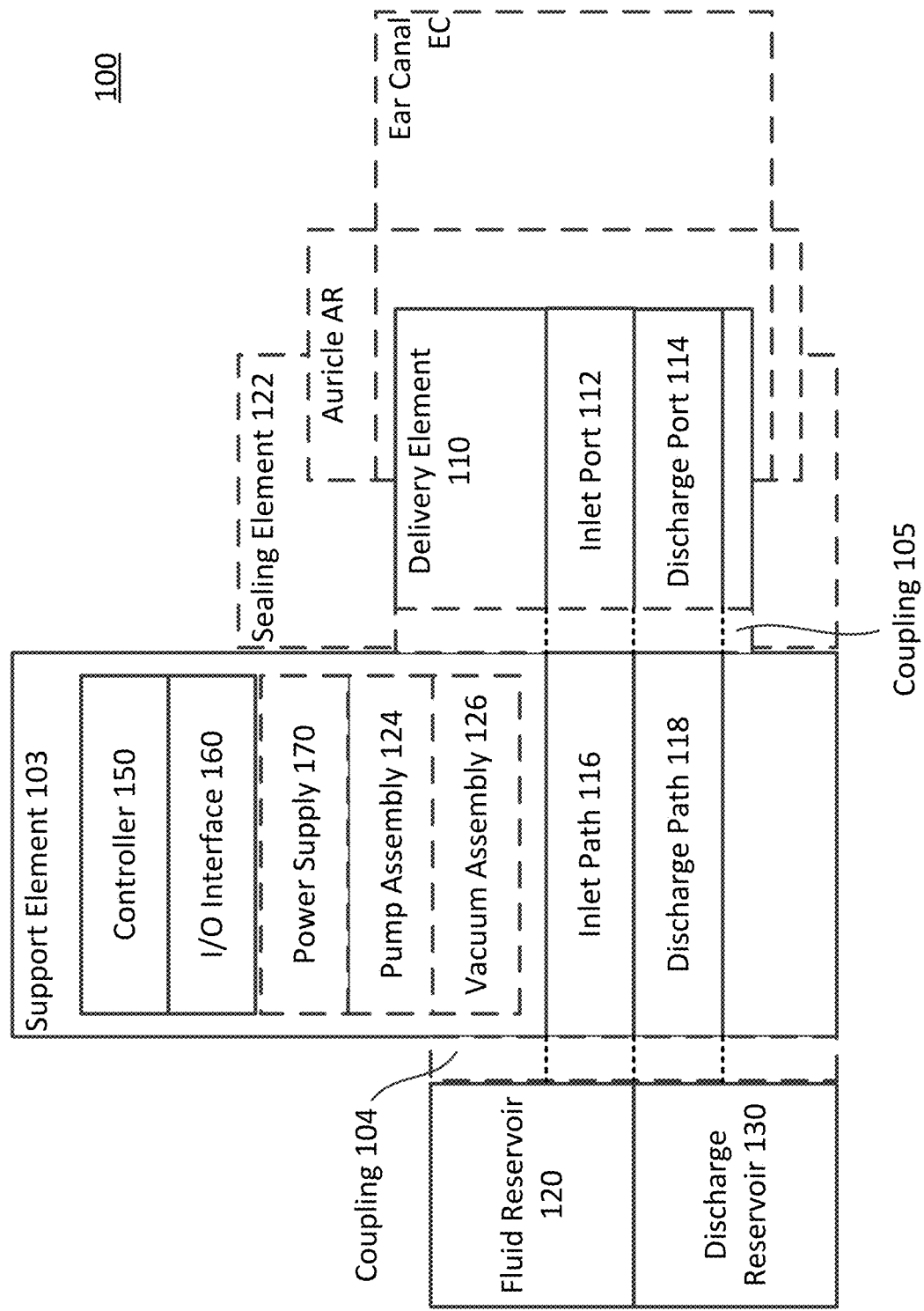
FIG. 1 is a schematic diagram depicting an ear cleaning or irrigation device, according to an embodiment.

FIG. 1 is a schematic diagram depicting an ear cleaning or irrigation device 100, according to an embodiment. As shown, the ear cleaning device 100 may include, for example, a delivery element or cannula 110, an inlet port 112, a discharge port 114, a fluid reservoir 120 ("fluid reservoir 120" or "cleaning agent reservoir 120" or "fluid cleaning agent reservoir 120"), a discharge reservoir 130, a support element 103, an inlet path 116, and a discharge path 118.

The ear cleaning device 100 represents, for example, a ear cleaning device. As an example, the ear cleaning device 100 may be worn on or by a user (e.g. on a head of the user), by positioning the support element 103 adjacent to auricle AR and mounting delivery element 110 in ear canal EC, to clean the ear canal EC by irrigation and removal of excessive ear wax. In some implementations, the irrigation and removal of excessive ear wax may include, for example, delivering a fluid cleaning agent to ear canal EC from the fluid reservoir 120 via the inlet path 116 and the inlet port 112. The fluid can be delivered at a preset pressure and/or preset flow rate sufficient to dislodge excessive ear wax from surfaces located in the ear canal EC. In some implementations, the fluid can be pre-pressurized within the fluid reservoir 120 such that the fluid, when released from the fluid reservoir 120 (e.g., by a valve), is delivered under a preset pressure and/or preset flow rate. The irrigation and removal of excessive ear wax may further include removing applied fluid from ear canal EC by discharge of the applied fluid through discharge port 114. The discharged fluid may be received in discharge reservoir 130 for later disposal via discharge path 118. The applied fluid may include a mixture of applied cleaning fluid and dislodged and entrained excessive ear wax from the ear canal EC.

Various portions of ear cleaning device 100 may be anatomically sized to fit a user, such as with respect to an anatomical size of auricle AR and/or ear canal EC, as shown in FIG. 1. For example, in some implementations, ear cleaning device 100 may include a delivery element (e.g. delivery element 110) having a longitudinally tapering or constant diameter, cross-section, or the like, to facilitate insertion and fit in ear canal EC. In some implementations, delivery element 110 may include, for example, a longitudinally tapering diameter having variation within a range of approximately 4 to 7 millimeters (mm). In some implementations, delivery element 110 may include a longitudinally tapering diameter having variation within a range suitable and compatible for use with an anatomical size of a user, patient, or subject. In some implementations, delivery element 110 may include a longitudinally tapering shape that gradually decreases in diameter from a proximal end (e.g. as in the end adjacent to the support element 103) to a distal end (e.g. as in the end disposable in ear canal EC). Delivery element 110 may otherwise include a longitudinally constant diameter.

The delivery element 110 may include, for example, a nozzle. The nozzle may include an inlet port 112 and a discharge port 114. In some implementations, the delivery element 110 may be disposable and/or recyclable. For example, in some implementations, the delivery element 110 include or be may be made partially or entirely of disposable and/or recyclable plastic materials. The delivery element 110 can be sized for use by different patient populations, e.g., for use by an adult, a child, and/or other populations.

In some implementations, ear cleaning device 100 may optionally include sealing element 122. Sealing element 122 may be positioned adjacent to a perimeter of delivery element 110 to form a seal about delivery element 110. For example, sealing element 122 may include an annular membrane concentrically arranged at or about the perimeter of delivery element 110. In some implementations, the annular membrane 111 may be sized and shaped to resemble a portion of a solid torus (e.g., the top half of a doughnut). Such a curved or partially toroidal surface may be used to create a seal or barrier about delivery element 110, so as to contain communicated fluid to increase the user's comfort when wearing the ear cleaning device 100.

Inlet port 112 may include, for example, one or more fluid delivery apertures or ports to enable and facilitate fluid communication from inlet port 112 to ear canal EC for introducing and applying fluid (e.g., having cleaning agent) to ear canal EC under pressure. In some implementations, inlet port 112 may be configured based on parameters relating to, for example, flow rate, flow type (e.g., laminar, turbulent, etc.), dimensions, shape, and the like. Inlet port 112 may be connected to inlet path 116 by way of coupling 105 for fluid communication with fluid reservoir 120 by way of coupling 104. In some implementations, inlet port 112 may be dimensioned for integration with or coupling to delivery element 110. For example, inlet port 112 may be embedded in or coupled to delivery element 110. In general, inlet port 112 may be fluidly connected to or otherwise formed as a part of delivery element 110 in any suitable manner to enable delivery and application of fluid to ear canal EC.

Discharge port 114 may include, for example, one or more fluid discharge apertures or ports to enable and facilitate fluid communication from ear canal EC to discharge port 114 for receiving and discharging applied fluid from ear canal EC (e.g., for disposal in discharge reservoir 130). In some implementations, discharge port 114 may be configured based on parameters related to flow rate, flow type (e.g., laminar, turbulent, etc.), dimensions, shape, and the like. In some implementations, discharge port 114 may include a valve, such as a non-return valve, check-valve 1-way valve, or the like, such as to prevent recirculation of applied fluid in ear canal EC. The valve may be configured based on parameters related to cracking pressure, dimensions, shape, and the like. In some implementations, discharge port 114 may be connected to discharge path 118 by way of coupling 105 for fluid communication with discharge reservoir 130 by way of coupling 104. Discharge port 114 may be dimensioned for integration with or coupling to delivery element 110 such as in a manner similar to that described with reference to inlet port 112. In general, discharge port 114 may be fluidly connected to or otherwise formed as part of delivery element 110 in any suitable manner to enable receipt and discharge of applied fluid from ear canal EC.

Fluid reservoir 120 may be configured to contain a liquid, e.g., a liquid including a cleaning agent for irrigation and cleaning of a user's auditory canal (e.g., ear canal EC). The cleaning agent can include, for example, an antimicrobial agent, an antifungal agent, an antibacterial agent, an acidic agent, an alkaline agent, a neutral agent, etc. In some embodiments, the liquid can include a buffer solution for maintaining a specific pH. In some implementations, the fluid cleaning agent may include, for example, water, a saline solution, and/or a hydrogen peroxide solution. The fluid reservoir 120 may connect to inlet path 116 by way of coupling 104, and inlet path 116 may connect to inlet port 112 by way of coupling 105 to establish fluid communication therebetween. Fluid reservoir 120 may be or include, for example, a reservoir, container, or the like. In some implementations, the fluid reservoir 120 may be disposable or recyclable. In some implementations, the fluid may alternatively or additionally include, for example, an anti-bacterial agent, an antibiotic agent, or the like.

In some implementations, fluid reservoir 120 may be configured to heat a contained supply of fluid cleaning agent to, for example, a temperature range having limits substantially equal to, above, and/or below body temperature (e.g., of a user), such as to support a comfort level of the user during use of the irrigation device 100. In such implementations, the fluid reservoir 120 may include, for example, a heating component such as a heater or resistive element configured to heat and maintain the contained supply of fluid at a predefined (e.g., user-selected) temperature. In such implementations, the fluid reservoir 120 may be insulated. In such implementations, the fluid reservoir 120 may include a temperature sensor such as a thermometer for measuring the temperature of a contained supply of fluid. In some implementations, the cleaning agent reservoir 120 may be filled with a supply of cleaning agent at approximately body temperature. For example, in some implementations, the fluid reservoir 120 may be pre-filled (e.g., come pre-packaged with a supply of a fluid cleaning agent). In other implementations, a user or someone (e.g., a physician or other medical practitioner) administering the fluid cleaning agent can prepare and/or fill the fluid reservoir 120 with a supply of fluid cleaning agent, as described with reference to FIG. 18.

The discharge reservoir 130 may connect to a discharge path 118 by way of a coupling 104, and the discharge path 118 may connect to a discharge port 114 by way of a coupling 105, to establish fluid communication therebetween. The discharge reservoir 130 may include, for example, a container or reservoir for receiving and containing applied fluid from a user's auditory canal (e.g. for later disposal). For example, the fluid received by and contained in the discharge reservoir 130 may include a mixture of applied fluid having dislodged and entrained excessive ear wax from ear canal EC. In some implementations, the discharge reservoir 130 may be disposable and/or recyclable. For example, in some implementations, the discharge reservoir 130 may be made of disposable and/or recyclable plastic materials. In some implementations, the fluid reservoir 120 and/or the discharge reservoir 130 may be enclosed within one or more containers configured for removable attachment to the support element 103, as shown in FIG. 1.

In some implementations, the support element 103 may include a controller 150, an input/output (I/O) or user interface 160 ("I/O interface 160" or "user interface 160"), an inlet path 116, and a discharge path 118.

The support element 103 may be configured, sized, and shaped to fit on, over, or about an ear of a user at a position adjacent to auricle AR to facilitate mounting of delivery element 110 in ear canal EC, and further, to facilitate establishing and maintaining fluid communication between fluid reservoir 120 and inlet port 112 as well as between discharge reservoir 130 and discharge port 114, respectively. For example, in some implementations, inlet path 116 may be connected at a proximal end to fluid reservoir 120 by way of a first fluid coupling (e.g. coupling 104), and at a distal end to inlet port 112 by way of a second fluid coupling (e.g. coupling 105), as shown in FIG. 1. Similarly, discharge path 118 may be connected at a proximal end to discharge reservoir 130 by way of a third fluid coupling (e.g. of coupling 104), and at a distal end to inlet port 112 by way of a fourth fluid coupling (e.g. of coupling 105), as shown in FIG. 1.

Each coupling 104 and 105 may include one or more suitable fluid interfaces, adaptors, fittings, couplings, and the like. Coupling 104 may include the first and third fluid couplings and coupling 105 may include the second and fourth fluid couplings. In some implementations, couplings 104 and/or 105 may include peripheral components for confirming connections, such as between one or more of inlet port 112, inlet path 116, and/or fluid reservoir 120, as well as between discharge port 114, discharge path 118, and/or discharge reservoir 130. For example, couplings 104 and/or 105 may include components that generate an auditory signal (e.g., a "click" noise), a haptic signal, a visual signal, and/or otherwise indicate proper coupling between the different components of the ear cleaning device 100.

The controller 150 may be configured to provide control to a user over the operations of the ear cleaning device 100. The controller 150 may include any suitable type of controller or processor. The controller 150 may be connected to the I/O interface 160 for data communications. In some implementations, the controller 150 and the I/O interface 160 may be coupled for data communications. For example, the controller 150 may be configured to send, receive, transmit or otherwise communicate data (e.g., user input data, operational status data, etc.) to and from I/O interface 160. The data communications between the controller 150 and the I/O interface 160 may be transmitted via wired, wireless, or fiber optic connections. For example, the controller 150 may include control circuitry (not depicted) for communicating and/or executing machine-executable program instructions (e.g., as may be stored on machine-readable storage media). In the example, the controller 150 may execute a set of machine-executable instructions corresponding to an ear cleaning operation or procedure, such as may be stored on machine-readable storage media, upon command by a user. The ear cleaning device 100 may be controlled (e.g., by a user) by way of the controller 150 and the I/O interface 160 with respect to a target treatment volume or area, such as the space or surface in, about, or along ear canal EC and/or auricle AR.

The I/O interface 160 may be configured to receive user inputs and commands from a user. In some implementations, the I/O interface 160 may include, for example, a button, switch, touch screen, and/or any other suitable actuation mechanism to receive the user inputs and commands. The I/O interface 160 may additionally or alternatively include, for example, a display or screen (not depicted) for displaying feedback such as device or operational status to the user, such as with respect to irrigation operation to be performed, and the like. The I/O interface 160 may be electrically and communicatively coupled to the controller 150 for data communications. The data communications may include, for example, user inputs received by the I/O interface 160 from the user, which may be communicated or sent to the controller 150 for execution in performing a user-selected ear cleaning operation. The user inputs may include, for example, selections of one or more of a plurality of irrigation programs (e.g., respectively stored as sets of processor-executable instructions on one or more memories), as described in further detail with reference to FIG. 4.

In some implementations, the I/O interface 160 may include a touchscreen device. The touchscreen device may be configured to, for example, receive user inputs from and provide feedback to the user such as by way of a display to facilitate user selection, adjustment, and configuration of irrigation operations to be performed by the ear cleaning device 100. In some implementations, the touchscreen device of the I/O interface 160 may be configured to render and display one or more graphical user interface symbols or elements resembling one or more corresponding user interface elements, such as buttons, scales, bars, panels, switches, or any other user interface element corresponding to a control signal or user-selectable input or command.

With continued reference to FIG. 1, in some implementations, the ear cleaning device 100 may include a power supply 170, a pump assembly 124, and a vacuum assembly 126.

The power supply 170 may be configured to store and supply power to various power-consuming components of the ear cleaning device 100, such as the controller 150, the I/O interface 160, the pump assembly 124, and/or the vacuum assembly 126. In some implementations, for example, the power supply 170 may include a portable power source such as a battery, or the like, having a power storage capacity sufficient to supply power to the power-consuming components of the ear cleaning device 100 for performance of an irrigation operation.

In some implementations, for example, the pump assembly 124 may include any suitable pneumatic, hydraulic, or mechanical pump configured to move fluid from the fluid reservoir 120 to the ear canal EC under pressure (e.g. at a positive pressure greater than one atmosphere, or ambient pressure). The pump assembly 124 may be configured to couple to fluid reservoir 120, inlet path 116, and inlet port 112 to move a supply of fluid from the fluid reservoir 120 to the ear canal EC under a preset pressure and/or at a preset flow rate. For example, the pump assembly 124 may include a positive displacement pump such as a peristaltic pump, a diaphragm pump, or the like. In some implementations, the pump assembly 124 may be configured to move the supply of fluid in conjunction with one or more peripheral devices such as pressure storage reservoir (e.g., a hydraulic accumulator), flow-control valves, an energy storage device such as an internal, elastic diaphragm positioned in the fluid reservoir 120, and the like.

The vacuum assembly 126 may include, for example, a vacuum or suction pump (e.g., a scroll pump) or any other suitable type of pump for generating and applying a vacuum or suction (e.g., at negative pressure less than one atmosphere or ambient pressure), such as with respect to the discharge reservoir 130, to draw fluid from the ear canal EC. Vacuum assembly 126 may couple to discharge reservoir 130, discharge path 118, and discharge port 114 to apply the vacuum to ear canal EC for discharge and receipt of previously applied fluid, having dislodged and entrained excessive ear wax from ear canal EC. In some implementations, ear cleaning device 100 does not include a vacuum assembly 126, and in such implementations, fluid may drain from the ear, e.g., due to a pressure differential between the ear canal EC and one or more of the discharge port 114, discharge path 118, and discharge reservoir 130. Such a pressure differential can result from the delivery of pressurized fluid into the ear canal EC and/or due to a pre-set vacuum within discharge reservoir 130. In some implementations, while ear cleaning device 100 does not include a vacuum assembly 126, ear cleaning device 100 can be coupled to a vacuum that can draw fluid out from the ear via discharge port 114 and/or another fluid path (not depicted). For example, a vacuum can be coupled to discharge reservoir 130 to generate a vacuum for withdrawing fluid from the ear canal EC.

As an example, in some implementations, a device (e.g., ear cleaning device 100) to irrigate ear canal(s) of human ear(s) (e.g., auricle AR and ear canal EC) may include a first over-ear earpiece (e.g., support element 103) sized and dimensioned to be worn over human ears and having a cavity sized and dimensioned to receive one human ear. The device (e.g., ear cleaning device 100) may include a first cleaning agent reservoir (e.g., fluid reservoir 120) to hold cleaning agents, and a first discharge collection reservoir (e.g., discharge reservoir 130) to collect and hold discharge from irrigation. The device (e.g., the ear cleaning device 100) may further include a first cleaning interface (e.g., delivery element 110) to which one or more cleaning agent delivery elements are selectively, detachably, and physically coupleable. The device (e.g., the ear cleaning device 100) may further include a first fluid communication path (e.g., extending between fluid reservoir 120 and inlet port 112 across inlet path 116) that provides fluid communication for the cleaning agent between the first cleaning agent reservoir and the first cleaning interface, and a second fluid communication path (e.g., extending between discharge reservoir 130 and discharge port 114 across discharge path 118) that provides fluid communication for communication of the discharge between the first discharge collection reservoir and the first cleaning interface. The device (e.g., ear cleaning device 100) may be implemented by a user (e.g., via I/O interface 160) to perform (e.g., via controller 150) an ear cleaning operation or procedure to clean the auricle AR and the ear canal EC by irrigation and removal of excessive ear wax.

Figure 2:
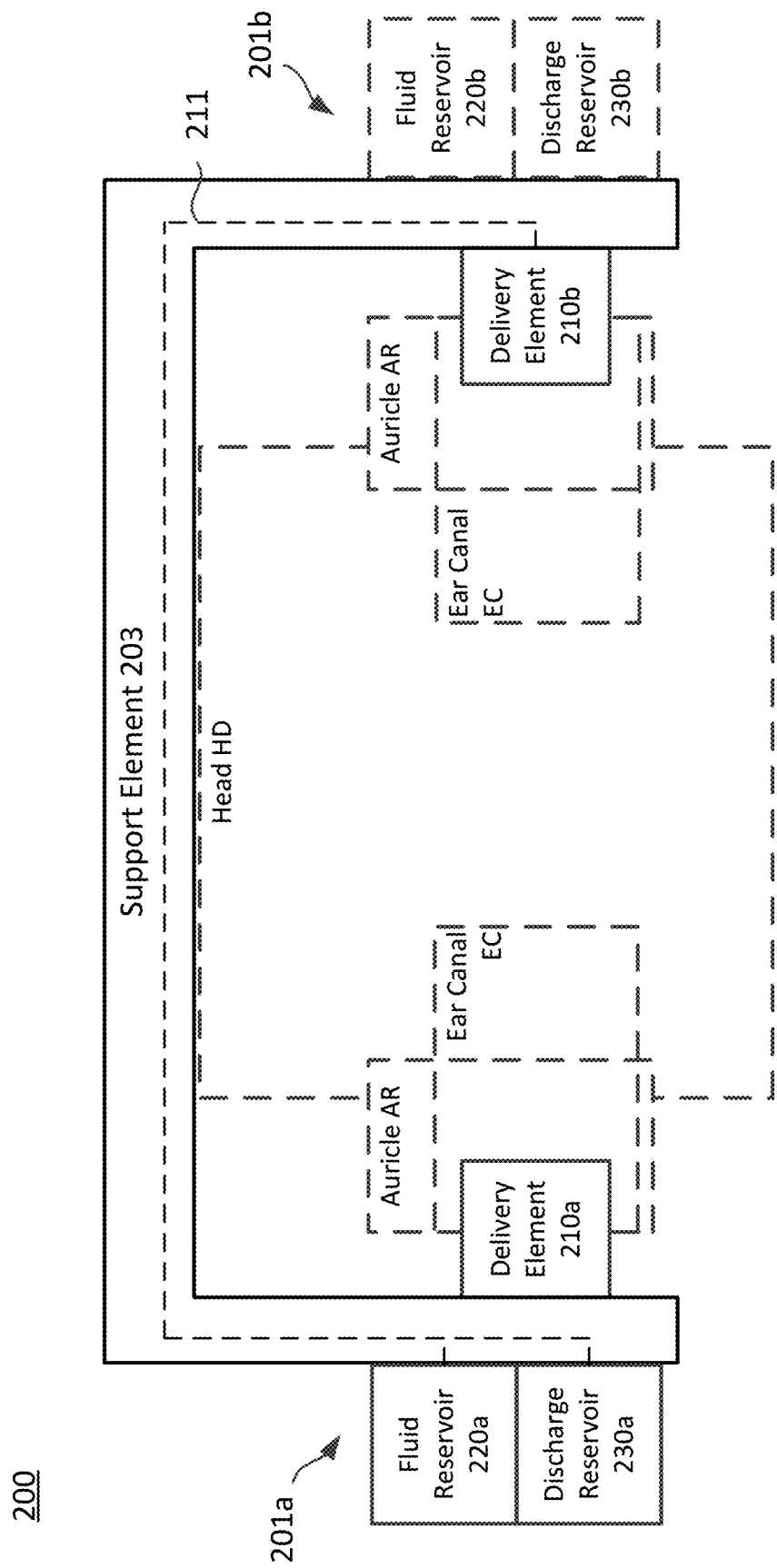
FIG. 2 is a schematic diagram depicting an ear cleaning or irrigation device, according to an embodiment.

FIG. 2 is a schematic diagram depicting an ear cleaning or irrigation device 200, according to an embodiment. As shown, the ear cleaning device 200 may include, for example, first and second earsets or over-ear earpieces 201*a* and 201*b* (collectively, "earset(s) 201" or "over-ear earpiece(s) 201"), connected to one another by a support element 203. Further, the over-ear earpieces 201*a* and 201*b* may respectively include first and second delivery elements 210*a* and 210*b* (collectively, "delivery element(s) 210"), configured for respective insertion and mounting in first and second ear canals EC, first and second fluid reservoirs 220*a* and 220*b* (collectively, "fluid reservoir(s) 220" or "cleaning agent reservoir(s) 220" or "fluid cleaning agent reservoir(s) 220"), and first and second discharge reservoirs 230*a* and 230*b* (collectively, "discharge reservoir(s) 230"). In some implementations, the over-ear earpieces 201 and/or the support element 203 may be similar in structure, form, and/or function to that of the ear cleaning device 100 and the support element 103, as described with reference to FIG. 1.

The earsets 201 represent, for example, individual ear cleaning devices such as that described with reference to FIG. 1. In some implementations, the earsets 201 may be operably connected to one another by the support element 203, as shown in FIG. 2, and may be configured for concurrent or individual use in cleaning ear canals EC— simultaneously or one at a time—by irrigation and removal of excessive ear wax. For example, as shown in FIG. 2, the ear cleaning device 200 may be worn on or by a user by positioning the support element 203 atop head HD and adjacent auricles AR, and mounting delivery elements 210 in the ear canals EC, to clean the ear canals EC simultaneously or one at a time by irrigation and removal of excessive ear wax therefrom.

The earsets 201 may be similar in structure, form, and/or function. In some implementations, for example, the first earset 201a may include delivery element 210a, fluid reservoir 220a, and discharge reservoir 230a, and the second earset 201b may include delivery element 210b, and in some optional instances, fluid reservoir 220b, and discharge reservoir 230b. The fluid reservoirs 220, the discharge reservoirs 230, and the delivery elements 210 may be analogous (e.g., as in structure, form, or function) to the fluid reservoir 120, the discharge reservoir 130, and the delivery element 110, as described with reference to FIG. 1. Further, while not depicted, in some implementations the earsets 201 may respectively include one or more of the components described with reference to the ear cleaning device 100, including, for example, the sealing element 122, the controller 150, the I/O interface 160, the power supply 170, the pump assembly 124, and/or the vacuum assembly 126. The earsets 201 may each respectively include a vertical axis (not depicted) oriented substantially perpendicular to the ground when a user wearing ear cleaning device 200 is in an upright position, and a horizontal or lateral axis oriented substantially parallel to the ground when the user wearing ear cleaning device 200 is in the upright position. While discussed with respect to an upright positon for ease of reference, it should be noted that a user does not necessarily need to be in an upright position during use of ear cleaning device 200.

In some implementations, the earsets 201 may be operably connected to one another, for example, by way of respective fluid couplings and one or more fluid communication paths 211. As shown in FIG. 2, in some implementations, the one or more fluid communication paths 211 may be configured to enable fluid communication between the delivery element 210b and the fluid reservoir 220a as well as the discharge reservoir 230a. In such implementations, the first fluid reservoir 220a may include a fluid capacity sufficient to contain a supply of fluid for performing an irrigation operation (e.g., at least 70 milliliters), in which the fluid is delivered into both the first and second ear canals EC of a user via respective delivery elements 210a and 210b. Further, in such implementations, the first discharge reservoir 230a may include a fluid capacity equal to or greater than that of the fluid reservoir 220a, to contain applied fluid removed from both the first and second ear canals EC of the user via the respective delivery elements 210a and 210b during the irrigation operation. In other implementations, the delivery element 210b may additionally or alternatively be configured for fluid communication with the fluid reservoir 220b and the discharge reservoir 230b. For example, the one or more fluid communication paths 211 may be configured to alternatively or additionally enable fluid communication between the delivery element 210b and the fluid reservoir 220b as well as the discharge reservoir 230b.

In some implementations, the irrigation of and removal of excessive ear wax from the first ear canal EC may include, for example, delivering fluid under pressure from the first fluid reservoir 220a to the first ear canal EC by way of the first delivery element 210a, as shown in FIG. 2. In such implementations, the irrigation and removal of excessive ear wax from the first ear canal EC may further include, for example, removing, by way of the first delivery element 210a, the delivered and applied fluid from the first ear canal EC for disposal in the discharge reservoir 230a. In some implementations, the irrigation and removal of excessive ear wax from the second ear canal EC may include, for example, delivering fluid under pressure from the first and/or second fluid reservoirs 220a and 220b to the second ear canal EC by way of the second delivery element 210b. In such implementations, the irrigation of and removal of excessive ear wax from the second ear canal EC may further include, for example, removing, by way of the second delivery element 210b, the delivered and applied fluid from the second ear canal EC for disposal in the first and/or second discharge reservoirs 230a and 230b.

Various portions of ear cleaning device 200 may be anatomically sized to fit various users, such as with respect to various anatomical sizes of and/or spatial relations between head HD, auricle AR, and/or ear canal EC, as shown in FIG. 2. In some implementations, the support element 203 may include, for example, an adjustable (e.g., deformable or flexible) head strap, one or more vertical adjustors (not depicted), and one or more pivot couplers (not depicted) to enable and facilitate adjustment and variation of the relative spatial positions of the first and second earsets 201 by a user. The adjustment and variation of the relative spatial positions of the first and second earsets 201 may include, for example, lateral or horizontal displacement of the first or second earsets 201 with respect to a lateral axis extending between points on the first and second earsets 201, vertical displacement of the first or second earsets 201 with respect to a vertically-oriented axis, and the like. Accordingly, the ear cleaning device 200 may be configured to accommodate various head shapes and sizes of various users (e.g., various circumferential distances between the ears of the various users) by enabling selective spatial positioning and fitting adjustment of the first and second earsets 201.

In some implementations, the one or more pivot couplers with which each earset 201 may individually and respectively couple or connect may be configured to enable and facilitate independent rotational displacement ("rotational displacement" or "rotational motion" or "pivoting motion" or "pivotal motion") of each earset 201 about respective, spaced-apart axes. Accordingly, the pivot couplers may be configured to enable and facilitate more comfortable and individualized fit of the earsets 201 on various users, by accommodation of the unique contours and shapes of individual user's heads.

In some implementations, the first and second earsets 201a-b may include respective annular brackets (not depicted). Each annular bracket may be individually sized and shaped to be slightly larger than a portion of a perimeter of a respectively associated earset (e.g., the first earset 201a or the second earset 201b). As an example, in some implementations, a first annular bracket may be sized and shaped to run along the top half of the perimeter of a respectively associated earset including the first earset 201a, and a second annular bracket may be sized and shaped to run along the top half of the perimeter of a respectively associated earset including the second earset 201b. Each annular bracket may be pivotally coupled to support element 203 at and by way of a junction, interface, or physical coupling, to enable and facilitate independent, rotational motion of the first and second earsets 201a-b, as described in further detail with reference to FIGS. 3A-3B, 18, 19A-19B, and 20A-20B.

Figure 3A:
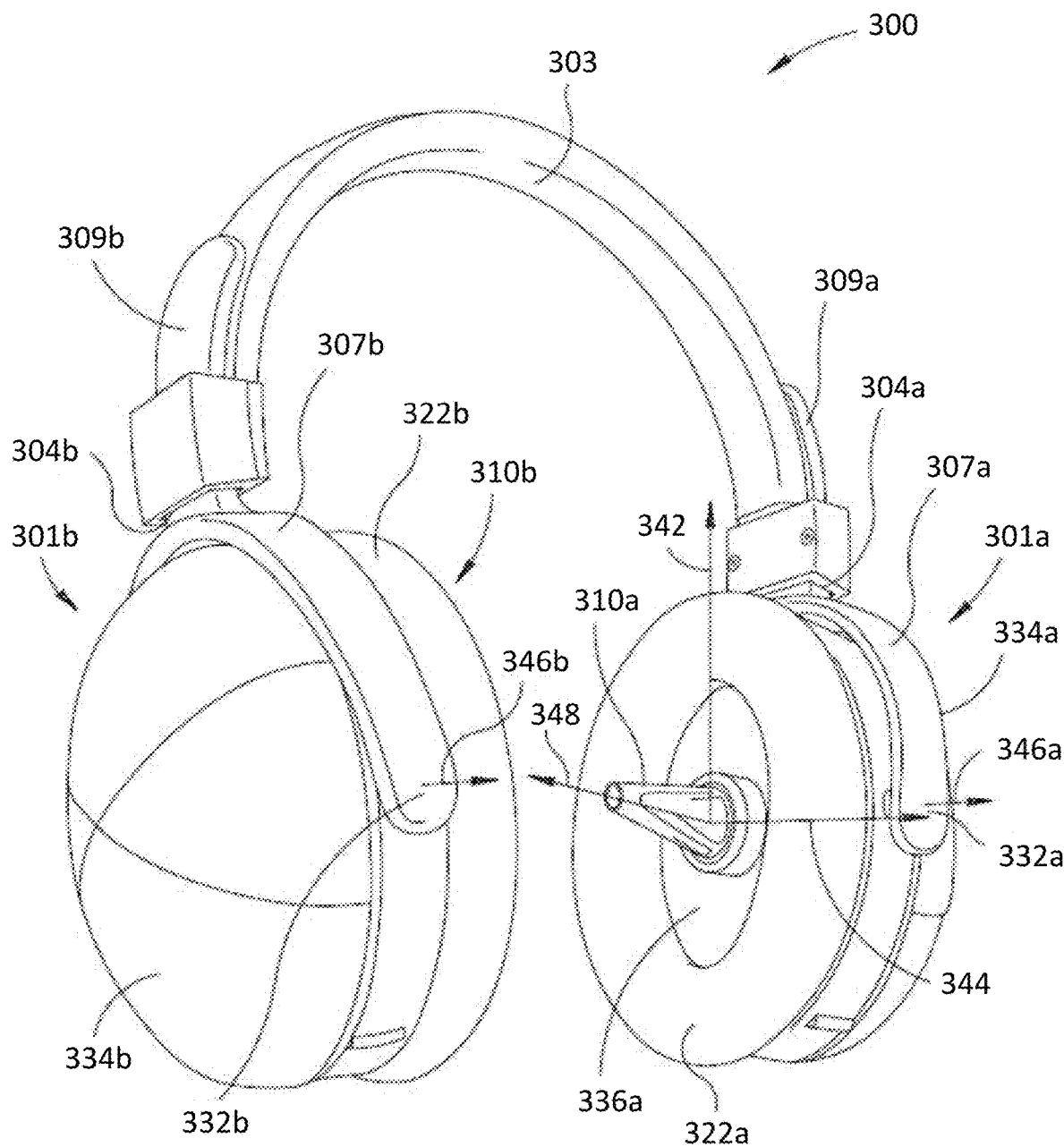
FIGS. 3A-3B are perspective views of an ear cleaning or irrigation device, according to an embodiment.
Figure 3B:
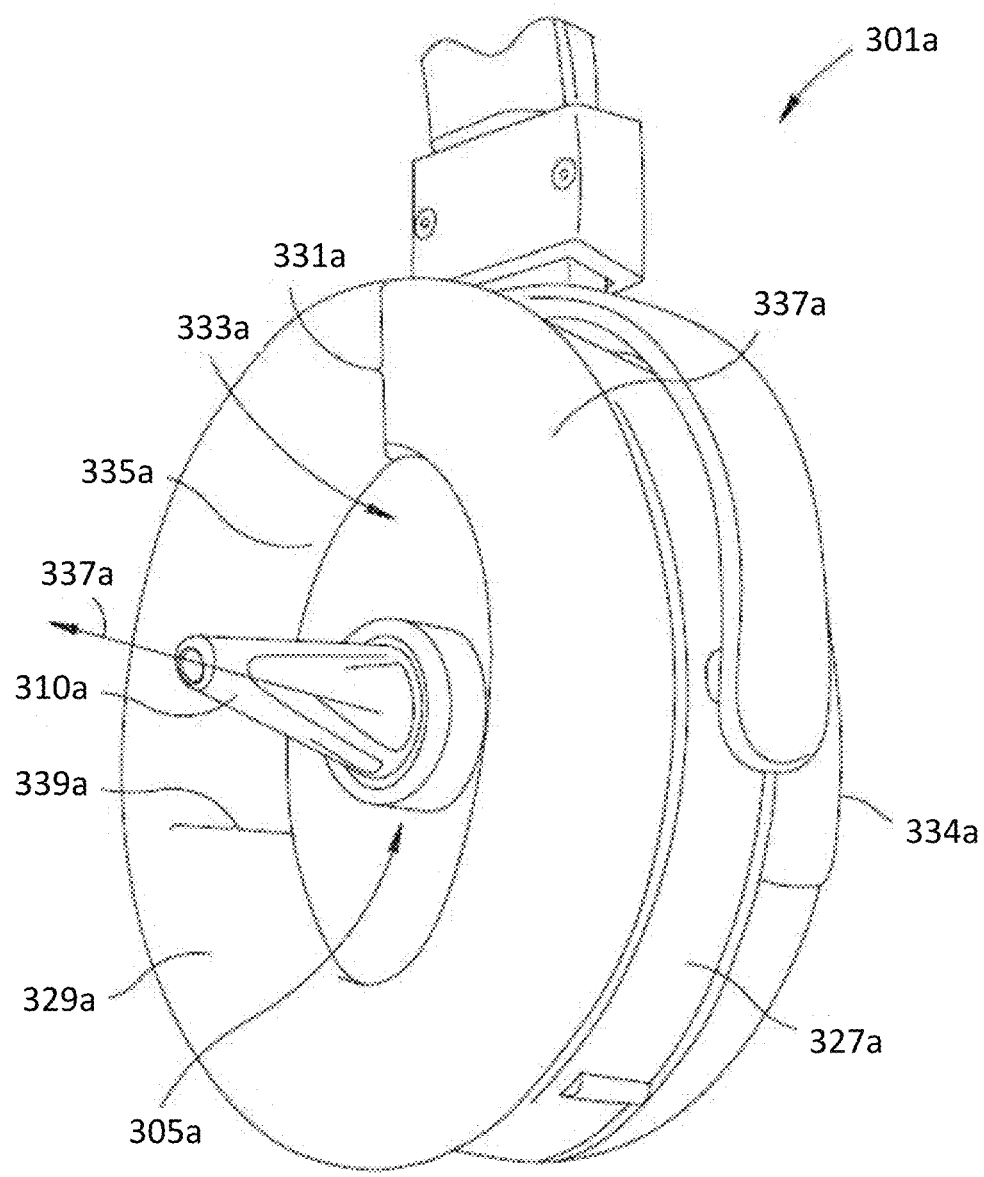

FIGS. 3A-3B are perspective views of an ear cleaning or irrigation device 300, according to an embodiment. As shown, the irrigation device 300 may include first and second over-ear earpieces or earsets 301a and 301b (collectively, "over-ear earpiece(s) 301" or "earset(s) 301"), a support element implemented as an adjustable head strap 303, and first and second delivery elements or cannulas 310a and 310b (collectively, "delivery element(s) 310" or "cannula(s) 310"), connected to respective cannula coupler interfaces 305a and 305b (collectively, "cannula coupler interface(s) 305"). While FIG. 3B shows the first over-ear earpiece 301a (depicted in FIG. 3A), it should be noted that FIG. 3B can reference the first over-ear earpiece 301a or the second over-ear earpiece 301b.

In some implementations, the irrigation device 300 may be sized and shaped such that the first over-ear earpiece 301a fits over a user's right ear, and the second over-ear earpiece 301b fits over the user's left ear. In some implementations, the irrigation device 300 may be sized and shaped such that the first over-ear earpiece 301a fits over a user's right or left ear, and the second over-ear earpiece 301b fits over the user's left or right ear. For example, each over-ear earpiece 301 may be sized and shaped for interchangeable fit over either of a user's right and left ears. Each over-ear earpiece may have a vertical axis 342, e.g., that is substantially perpendicular to the ground when a user wearing the irrigation device 300 is in an upright position, and a horizontal axis 344, e.g., that is substantially parallel to the ground when the user wearing the irrigation device 300 is in the upright position. While discussed with respect to an upright positon for illustration purposes, it is noted that a user does not necessarily need to be in an upright position during use of the irrigation device 300. For example, a user can be in a reclined position or a laying position, and in such position, the axes 342, 344 can be at other angles with respect to the ground.

With reference to FIG. 3B, each over-ear earpiece 301 may include an interior side 336a and an opposing exterior side 334a. The interior side 336a may be configured to be directed towards and positioned adjacent to a region about an ear of a user's head when the user wears the irrigation device 300. Each over-ear earpiece 301 may have a perimeter 327a that extends between the interior side 336a and the exterior side 334a. The perimeter 327a may be sized and shaped to enable the over-ear earpiece 301a to enclose a wide range of various ear shapes. In some implementations, for example, the perimeter 327a may be substantially circular, oval, or elliptical in shape.

In some implementations, the over-ear earpieces 301a and 301b may respectively include sealing elements, e.g., similar to the sealing element 122 described with reference to FIG. 1. In some implementations, the sealing elements may include, for example, annular membranes 322a and 322b (collectively, "annular membrane(s) 322"). For example, the annular membranes 322 may be respectively positioned on the interior sides 336 of the over-ear earpieces 301, at or proximate their perimeters 327. In some implementations, the annular membranes 322, such as shown with respect to the annular membrane 322a, may have an interior wall 335a and an exterior wall 337a that are separated by a distance 331a such that the interior wall 335a is concentric with and partially or completely enclosed by the exterior wall 337a. The interior wall 335a and the exterior wall 337a may be connected by a rim 329a that traverses the distance 331a. In some implementations, the rim 329a include a surface that curves outward, away from the over-ear earpiece 301a. For example, in some implementations, the annular membranes 322 may be sized and shaped to resemble a portion of a solid torus (e.g., the top half of a doughnut). Such a curved or partially toroidal surface may be used to increase the user's comfort when wearing the irrigation device 300. In some implementations, the rim 329a include a substantially flat surface that is substantially perpendicular to one or both of the interior and exterior walls 335a and 337a. While not depicted, it will be apparent to those of ordinary skill in the art that any of the aforementioned elements can also be applied in a similar manner to any analogous element of the over-ear earpiece 301b.

In some implementations, the annular membrane 322a may be made of a cushioning material that is deformable (e.g., compressible) upon application of force or pressure. In some implementations, the annular membrane 322a may be at least partially comprised of resilient material, such as to increase durability, and the like. For example, the cushioning material may include elastomeric or elastomer-based materials, such as closed-cell foam (e.g., polyurethane), open cell foam, gel in a pouch, silicone, and/or rubber which may include an outer cover of plastic, leather, leatherette material, and the like. Such cushioned and/or resilient materials may be configured to provide a comfortable fit for a user when wearing the irrigation device 300. Further, such cushioned and/or resilient materials may be configured to enable the annular membranes 322a, 322b to conform to the shape of the user's head when using the irrigation device 300. Accordingly, each annular membrane 322a, 322b may be configured to form a seal against the user's head to thereby trap cleaning agent that would otherwise escape, for example, from the respective cannula 310a, 310b and/or the user's auditory canals (e.g., ear canal EC) during an irrigation procedure. In some implementations, the annular membrane 322a may be formed of an inner core, composed at least in part of elastomer-based materials, and an outer protective cover encompassing the inner core, composed of resistant material such as a water-resistant plastic or some other synthetic material that does not wear or degrade when wet. Accordingly, the outer protective cover may be configured to protect the inner core from various elements in the environment. In some implementations, the annular membrane 322a may be detachably removable from the over-ear earpiece 301a to thereby enable periodic replacement, such as after each use of the irrigation device 300. While not depicted, it will be apparent to those of ordinary skill in the art that any of the aforementioned elements can also be applied in a similar manner to any analogous element of the over-ear earpiece 301b.

The interior wall 335a of the annular membrane 322a may form a cavity 333a that is sized and shaped to receive and enclose individual, variously sized and shaped ears of users. The size and shape of the annular membrane 322a and the cavity 333a may further be configured to position the cannula 310a within a user's auditory canal when the user is wearing the irrigation device 300. In some implementations, the cavity 333a may be cylindrical in shape to thereby create a cylindrical space in which the cannula 310a may be oriented, such as along a central axis 337a of the cavity 333a. In some implementations, the cavity 333a may be elongated such that the perimeter of the interior wall 335a forms a substantially elliptical or oval shape. In such implementations, the cavity 333a may be relatively longer along the vertical axis 342, and relatively shorter along the horizontal axis 344. Elongating the cavity 333a as such may improve or provide for a better, more comfortable fit for the user. While not depicted, it will be apparent to those of ordinary skill in the art that any of the aforementioned elements can also be applied in a similar manner to any analogous element of the over-ear earpiece 301b.

The cavity 333a may have a depth formed by a height 339a of the interior wall 335a. In some implementations, the depth of the cavity 333a may be less than a height of the cannula 310a, enabling the cannula 310a to extend past the rim 329a of the annular membrane 322a to thereby enter the user's auditory canal when the user wears the irrigation device 300. In some implementations, as further described below, the cannula 310a may be tapered such that a tip of the cannula 310a gradually narrows towards a base of the cannula 310a, to assist in insertion and positioning of the tip of the cannula 310a into the user's auditory canal. The tapering of the cannula 310a can be configured such that a portion of the cannula 310a between the tip and the base makes contact with the outside opening of the user's auditory canal, so as to prevent the tip of the cannula 310a from making contact with and potentially injuring the ear drums of the user. It will be apparent to those of ordinary skill in the art that any of the aforementioned elements can also be applied in a similar manner to any analogous element of the over-ear earpiece 301b (e.g., cannula 310b), in accordance with the present disclosure.

In some implementations, the irrigation device 300 may include a support element implemented as an adjustable head strap 303, configured to adjustably connect the first over-ear earpiece 301a and the second over-ear earpiece 301b in spaced apart spatial relation and position along a lateral axis 348. For example, as shown in FIG. 3A, the lateral axis 348 may be oriented coaxially with respect to a nozzle of the delivery element or cannula 310a. As another example, while not depicted in FIG. 3A, a lateral axis such as the lateral axis 348 may be oriented coaxially with respect to a nozzle of the delivery element or cannula 310b. The adjustable head strap 303 may be sized and shaped to fit over a user's head to thereby position the first over-ear earpiece 301a over the user's first ear, and the second over-ear earpiece 301b over the user's second ear. For example, in some implementations, the adjustable head strap 303 may be configured to be flexible such that the first over-ear earpiece 301a and the second over-ear earpiece 301b can be individually moved or flexed laterally, such as along or about the lateral axis 348.

The irrigation device 300 can include coupling elements implemented as vertical adjustors 309a and 309b (collectively, "vertical adjustor(s) 309"). In some implementations, for example, the vertical adjustors 309 may be configured to couple to one of the over-ear earpieces 301 to thereby enable each respectively coupled over-ear earpiece 301 to independently or otherwise move or rotate about the vertical axis 342, with respect to and along the adjustable head strap 303, when a user is wearing the irrigation device 300. Accordingly, the vertical adjustors 309 may be implemented in adjusting a fit of the irrigation device 300, such as to accommodate different user head sizes with respect to the various circumferential distances between different users' ears (e.g., from one ear of a user, over the top of the user's head, and to the other ear of the user).

In some implementations, the irrigation device 300 can include coupling elements implemented as pivot couplers 332a and 332b (collectively, "pivot coupler(s) 332") configured to respectively connect to the over-ear earpieces 301a and 301b, to thereby enable respective rotational and pivotal motion of the over-ear earpieces 301a and 301b about axes 346a and 346b, as shown in FIG. 3A. Accordingly, the pivot couplers 332 may be implemented in conjunction with the over-ear earpieces 301 to enable the irrigation device 300 to more comfortably fit on a user's head with respect to the contours of the user's head when the user dons the irrigation device 300.

In some implementations, the irrigation device 300 can include coupling elements implemented as annular brackets 307a and 307b (collectively, "annular bracket(s) 307"). The annular brackets 307 may be respectively sized and shaped to have a perimeter slightly larger than the perimeters 327a and 327b of the over-ear earpieces 301a and 301b to which each annular bracket 307 may respectively connect. For example, the annular brackets 307a and 307b may be respectively sized and shaped to run along the top half of the perimeters 327 (e.g., to partially fit about or encompass the perimeters 327) of the over-ear earpieces 301a and 301b. In some implementations, the annular brackets 307a and 307b may be pivotally coupled to the adjustable head strap 303 at junctions 304a and 304b to thereby enable each of the over-ear earpieces 301 to independently pivot at the junctions 304a and 304b.

Figure 4:
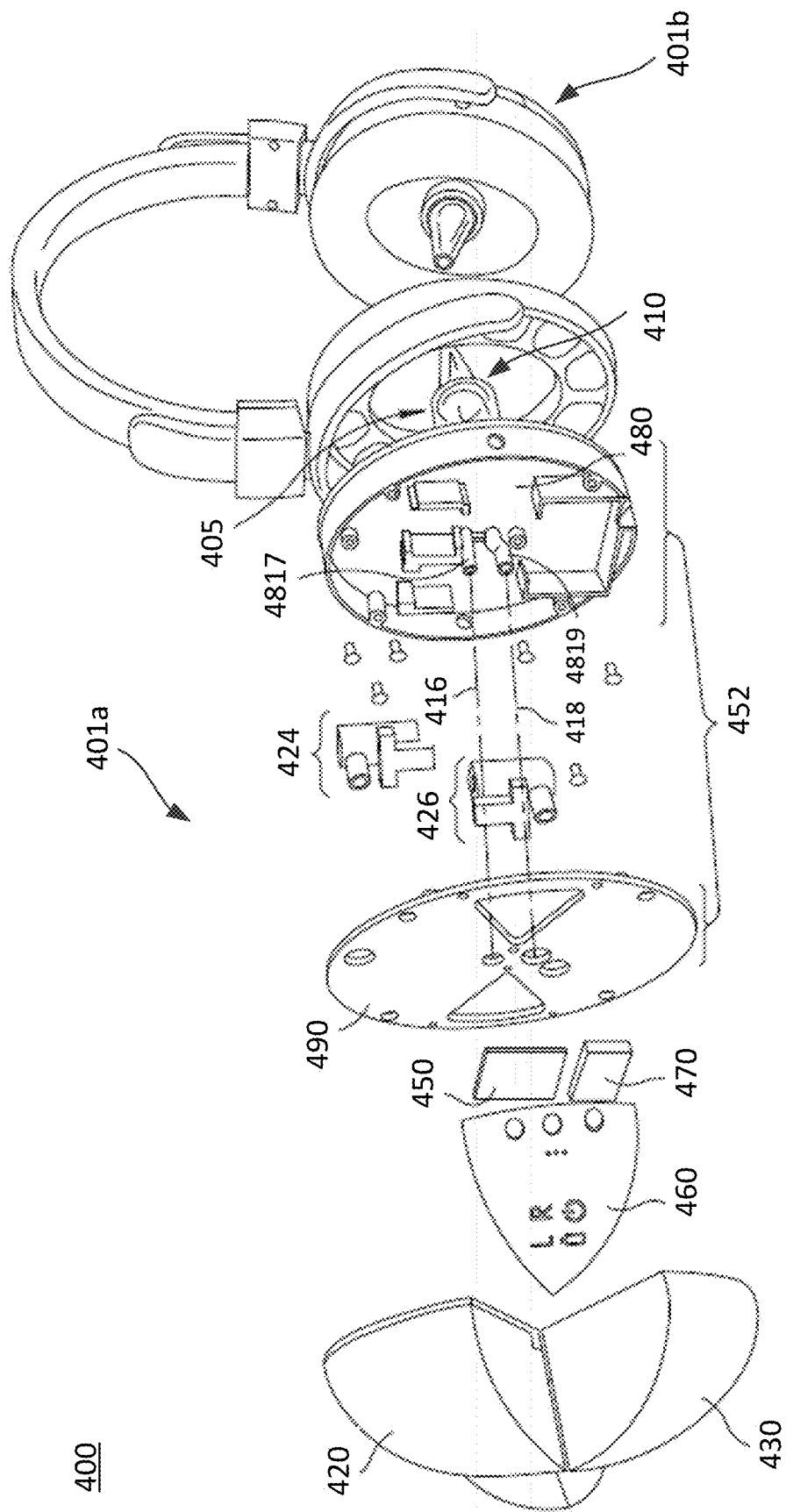
FIG. 4 is an exploded view of an over-ear earpiece or earset of an ear cleaning or irrigation device, according to an embodiment.

FIG. 4 is an exploded view of an over-ear earpiece or earset 401a of an ear cleaning or irrigation device 400, according to an embodiment. Similar to the irrigation device 300 described above, irrigation device 400 can include two earsets 401a, 401b that include structurally and functionally similar elements, but can be adapted for respective ears of a user. The irrigation device 400 can include components that are structurally and/or functionally similar to other irrigation devices described here, e.g., irrigation device 100. As shown, the over-ear earpiece 401a may include, for example, a delivery element implemented as a cannula 410, a fluid reservoir 420 ("fluid reservoir 420" or "cleaning agent reservoir 420" or "fluid cleaning agent reservoir 420"), a coupling or cannula coupler interface 405, a discharge reservoir 430 ("discharge reservoir 430" or "discharge collection reservoir 430"), a pump assembly 424, a vacuum assembly 426, a support element including a housing 452 including a lid 490 and a pan 480, controller circuitry 450, one or more power supply elements 470, and a user interface 460 having a set of user selectable controls ("user interface 460" or "set of user-actable selectable controls 460"). While not depicted in FIG. 4, it should be apparent to those of ordinary skill in the art that any of the aforementioned elements can be applied in a similar manner to any analogous element of the over-ear earpiece 401b, in accordance with embodiments of the present disclosure.

The cleaning agent reservoir 420 can contain a liquid (e.g., water, saline) such as, for example, a liquid including a cleaning agent (e.g., a supply of fluid cleaning agent) for irrigation and cleaning of a user's auditory canal (e.g., ear canal EC). The cleaning agent may include, for example, hydrogen peroxide. In some implementations, the cleaning agent reservoir 420 may be filled with a supply of liquid at a temperature approximately above, below, or equal to body temperature. For example, the cleaning agent reservoir 420 may be configured to be filled with and contain a supply of liquid with a cleaning agent at a temperature slightly above or below body temperature.

In some implementations, the cleaning agent reservoir 420 may include or be coupled to a heater (e.g., resistive heating component, etc.) and a temperature sensor (e.g., thermometer). The heater may be configured to heat the cleaning agent to, or maintain the cleaning agent at a predetermined (e.g., user-selected or preset) temperature (e.g., body temperature). The temperature sensor may be configured to measure temperatures of the cleaning agent with respect to time. The heater and the temperature sensor may be connected to the controller circuitry 450 (e.g., for feedback control over heating of the supply of fluid by the heater).

As an example, the temperature sensor may measure a temperature of the cleaning agent contained in the cleaning agent reservoir 420, and communicate a signal corresponding to the measured temperature to the controller circuitry 450. The controller circuitry 450 may control the operation (e.g., heating) of the heater with respect to a predetermined, user-selected temperature based on the signal received from the temperature sensor during an irrigation procedure to heat and maintain the cleaning agent contained in the cleaning agent reservoir 420 with respect to the predetermined, user-selected temperature, so as to enable delivery of the cleaning agent to the user's auditory canal (e.g., ear canal EC) at the user-selected temperature.

The cleaning agent reservoir 420 may be in fluid communication with the cannula coupler interface 405 by way of an inlet path implemented as a first fluid communication path ("flow path" or "fluid communication path" or "fluid fluidly communicative path"), such as cleaning fluid fluidly communicative path 416. As shown in FIG. 4, the cleaning fluid fluidly communicative path 416 may proceed through an opening in the lid 490, through a cleaning agent passage 4817 in the housing 452, to the cannula coupler interface 405. When an irrigation procedure begins, cleaning agent exits the cleaning agent reservoir 420 and proceeds through the cleaning fluid fluidly communicative path 416 to the cannula coupler interface 405 and towards an attached cannula 410. The pump assembly 424 may be coupled to the cleaning agent reservoir 420 to move the cleaning agent from the cleaning agent reservoir 420 and through the fluid fluidly communicative path 416 by applied pressure. In some implementations, the pump assembly 424 may include a pump configured to draw the cleaning agent from the cleaning agent reservoir 420 for discharge through a cannula (e.g., the cannula 105) at a preset pressure and/or flow rate. The cleaning agent may proceed into the cannula for discharge through one or more irrigation outlet apertures, as described in further detail herein. In some implementations, the upper limit of the pressure applicable by the pump assembly 424 may be less than about 100 kPa (approximately 0.986 atmospheres).

The discharge collection reservoir 430 may be in fluid communication with the cannula coupler interface 405 by way of an outlet path implemented as a second fluid communication path such as discharge fluidly communicative path 418. As shown in FIG. 4, the discharge fluid fluidly communicative path 418 may proceed from the cannula coupler interface 405, through a discharge passage 4819 in the housing 452, and through one or more openings in the lid 490, to the discharge collection reservoir 430. In some implementations, the vacuum assembly 426 (e.g., a vacuum pump, a suction pump, etc.) is used to create a vacuum or region of low pressure (e.g., lower than standard ambient environmental pressure, e.g., lower than 1 atmosphere) within the discharge collection reservoir 205 to facilitate removal of used or applied cleaning having dislodged and entrained excessive ear wax from ear canal EC. The vacuum assembly 426 may be coupled to the discharge collection reservoir 430 to move applied cleaning agent from auricle AR and/or ear canal EC, through the discharge fluidly communicative path 418, towards the discharge collection reservoir 430 by applied negative pressure (e.g., a partial vacuum). In some implementations, the vacuum assembly 426 may include a vacuum pump configured to draw applied cleaning agent from auricle AR and/or ear canal EC, towards the discharge collection reservoir 430 by discharge through the cannula 410 at a preset pressure and/or flow rate. The applied cleaning agent may proceed through the cannula 410 for discharge through one or more irrigation inlet apertures, as described in further detail herein. References to vacuum herein refer to a pressure that is lower than ambient environmental pressure (e.g., lower than 1 atmosphere) rather than an absolute vacuum.

In some implementations, the irrigation device 400 may be configured to leave applied cleaning agent in a user's auditory canal for a period of time (e.g., at least one minute following initial application) before removal. In some implementations, the time period may be set by the user via the user interface 460. In some implementations, the controller circuitry 450 may store processor-executable instructions that define one or more pre-set time periods for the cleaning agent to remain in the user's auditory canal. The user may choose one of these pre-set time periods via the user interface 460 such that the associated processor-executable instructions are executed by a processor of or connected to the controller circuitry 450. The time period in which the cleaning agent is introduced into the auditory canal, left to sit, and then removed can enable the cleaning agent to soften buildup in a user's auditory canal to thereby enhance the cleaning capabilities of the irrigation device 400 and improve the user's experience (e.g., the efficacy of removing earwax from the user's auditory canal). When the time period ends, the discharge from the irrigation is removed from the user's auditory canal via a discharge collection inlet port located on the cannula 410, as described in further detail herein.

In some implementations, the irrigation device 400 may be configured to pulse, at a pulsing frequency, cleaning agent into the user's auditory canal for a period of time (e.g., up to 30 seconds, 35 seconds, up to a one minute, or longer). For example, the irrigation device 400 may be configured to pulse cleaning agent into the user's auditory canal for a period of time such as 30 seconds, at a pulsing frequency of 0.5 Hz (or a pulsing period of 2 seconds). In such implementations, the vacuum assembly 426 may be actuated before the cleaning agent is first pulsed into the user's auditory canal for a time period, and subsequently, may remain actuated during the time period. The vacuum assembly 426 may be deactivated after the time period ends.

Figure 5A:
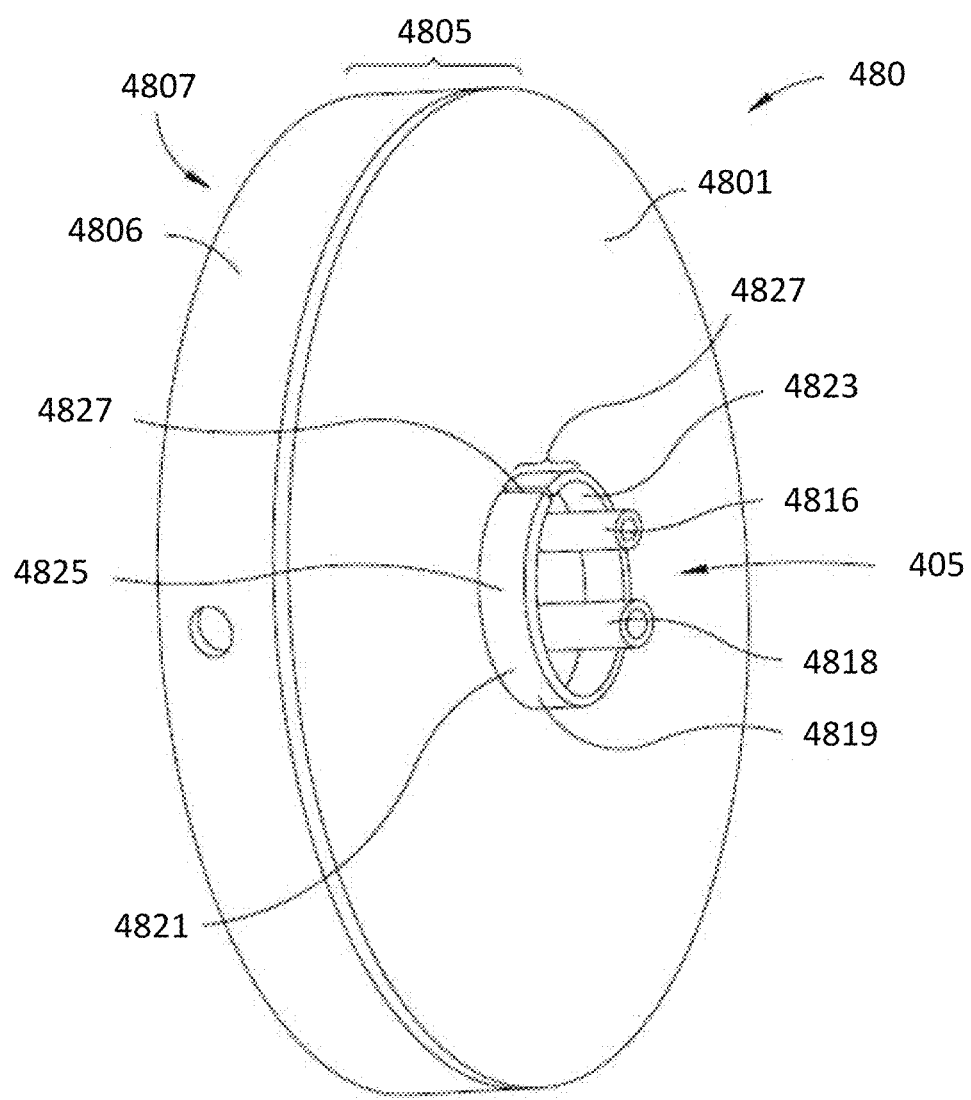
FIGS. 5A-5B are perspective views of a first side and a second side of a pan of an over-ear earpiece, according to an embodiment.
Figure 5B:
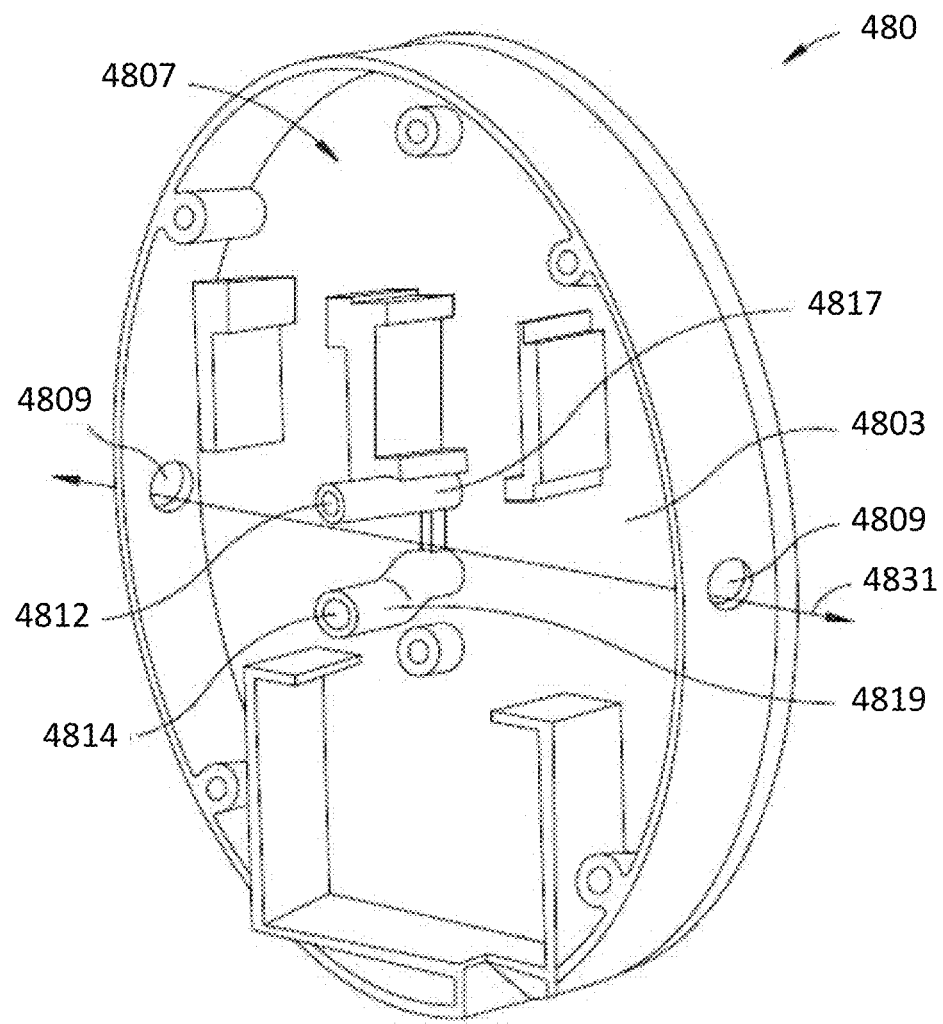

FIGS. 5A-5B are perspective views of a first side 4801 and a second side 4803 of the pan 480 of an over-ear earpiece 401a. The pan 480 can be, for example, a part of the housing 452 of the over-ear earpiece 401a. As shown, the first side 4801 of the pan 480 is oriented to face the cannula coupler interface 405 of the over-ear earpiece 401a. The second side 4803 of the pan 480 is oriented to face the cleaning agent reservoir 420 and the discharge collection reservoir 430. The lid 490 is attachable to the second side 4803 of the pan 480. The lid 490, when attached to the pan 480, is separated from the first side 4801 of the pan 480 by a distance 4805. The distance 4805 defines the depth of the housing 452. A side wall 4806 bridges the distance 4805. The attached lid 490, the first side 4801 of the pan 480, and the side wall 4806 may be configured to define an interior 4807 of the housing 452.

With reference to FIG. 5A, the cannula coupler interface 405 may include a cleaning agent port 4816, a vacuum port 4818, and one or more interfaces 4819. The cleaning agent port 4816 may be part of the cleaning fluid fluidly communicative path 416 for the cleaning agent, and may mate with a corresponding irrigation inlet port located on the cannula 410. For example, the cleaning agent port 4816 may include a male connector or fastener, and the irrigation inlet port located on the cannula 410 may be a corresponding female connector or fastener. Mating the cleaning agent port 4816 with the irrigation inlet port may establish a portion of a fluid path along which the cleaning agent may travel from the cleaning agent reservoir 420 to the cannula 410. The vacuum port 4818 may be part of the discharge fluidly communicative path 418 for the discharge and may mate with a corresponding discharge collection outlet port located on the cannula 410. For example, the vacuum port 4818 may include a male connector or fastener, and the discharge collection outlet port located on the cannula 410 may include a corresponding female connector or fastener. Mating the vacuum port 4818 with the discharge collection outlet port may establish a portion of a fluid path for the discharge to travel from the cannula 410 to the discharge collection reservoir 430.

The cannula coupler interface 405 may include an interface 4819 for physically coupling to one or more corresponding interfaces on the cannula 410. These complementary interfaces may enable the cannula 410 to be selectively detachable from the cannula coupler interface 405. In some implementations, the interface 4819 may be shaped to form and define an annular wall 4821 with an interior diameter 4823, an exterior diameter 4825, and a height 4827. The annular wall 4821 may be arranged to encompass the cleaning agent port 4816 and the vacuum port 4818. The annular wall 4821 may be configured to engage and couple with a corresponding interface on the cannula 410, such as by press-fit. For example, the interface on the cannula 410 may include a slot or opening sized to be only slightly larger than the annular wall 4821 such that frictional forces maintain physical coupling between the cannula 410 and the cannula coupler interface 405. In some implementations, one or more flexible, compressible seals, such as an O-ring, may be used to form a hermetic seal between the coupling interfaces on the cannula coupler interface 405 and the cannula 410.

In some implementations, the interface 4819 may include one or more registration features (e.g., grooves, channels, etc.) to facilitate alignment between the cleaning agent port 4816 and the vacuum port 4818 of the cannula coupler interface 405, with the corresponding irrigation inlet port and discharge collection outlet port located on the cannula 410, respectively, when the interface 4819 is engaged with the corresponding interface on the cannula 410. For example, the annular wall 4821 may include a slot 4827 sized and shaped to receive a corresponding tab of the cannula 410. In some implementations, the interface 4819 may additionally or alternatively include, for example, threads (e.g., screw or bolt threads) for facilitating connection with the cannula 410 by way of complimentary threads on the cannula 410. In some implementations, the interface 4819 may additionally or alternatively include, for example, an L-shaped slot (e.g., of a bayonet mount) for facilitating connection with the cannula 410 by insertion of a radial protrusion (e.g., a pin, etc.) on the cannula 410 into the L-shaped slot. In some implementations, the cannula 410 may be sized and shaped to mate with and couple to the cannula coupler interface 405 by press-fit. The interface 4819 may otherwise include any other suitable fastening or coupling mechanism for releasably connecting to the cannula 410, in accordance with embodiments of the present disclosure.

With reference to FIG. 5B, the second side 4803 of the pan 480 may include a cleaning agent passage 4817 and a discharge passage 4819. The cleaning agent passage 4817 may provide a first passage through the housing 452, from the cleaning agent reservoir 430 to the cannula coupler interface 405, to thereby form a portion of the cleaning fluid fluidly communicative path 416. The opening 4812 of the cleaning agent passage 4817, is directed towards the cleaning agent reservoir 420, and may be sized, shaped, and positioned to mate with a port on the cleaning agent reservoir 420. For example, the opening 4812 may form a male connector or fastener that mates with a female connector or fastener of a port of the cleaning agent reservoir 420.

The discharge passage 4819 may provide a second passage through the housing 452, from the cannula coupler interface 405 to the discharge collection reservoir 430, to thereby form a portion of the discharge fluidly communicative path 418. The opening 4814 of the discharge passage 4819, is directed towards the discharge collection reservoir 430, and may be sized, shaped, and positioned to mate with a port on the discharge collection reservoir 430. For example, the opening 4814 may form a male connector or fastener that mates with a female connector or fastener of a port of the discharge collection reservoir 430.

In some implementations, the cleaning agent passage 4817 or the discharge passage 4819 may instead be part of the cannula 410. In such implementations, each cannula (e.g., such as cannula 410) may provide for itself a cleaning agent passage (e.g., such as the cleaning agent passage 4817) and/or a discharge passage (e.g., such as the discharge passage 4819).

In some implementations, the cleaning agent passage 4817 or the discharge passage 4819 may be sealed to prevent leakage into the interior 4807 of the housing 452. In some implementations, the interior 4807 of the housing 452 may securely contain one or more additional components of the irrigation device 400, such as the pump assembly 424, the vacuum assembly 426, the controller circuitry 450, and/or the one or more power supplies 470.

In some implementations, the pan 480 may include one or more coupling apertures 4809 disposed or located on the side wall 4806 (shown in FIG. 5A) to enable the pan 480 and/or the housing 452 to be coupled to the annular bracket 307. In some implementations, the annular bracket 307 may include a coupling feature (e.g., a tab, a pin, etc.) configured to interface with coupling aperture 4809. Accordingly, the housing 452, and by extension the over-ear earpieces 401a, 401b, may be selectively detachably coupled to an annular bracket (e.g., annular brackets 307a, 307b) via the corresponding coupling features on the pan 480 and the annular bracket. The coupling feature of the annular bracket in conjunction with the corresponding coupling aperture 4809 of the pan 480 and the housing 452 may form pivot couplers (e.g., pivot couplers 332a, 332b).

Figure 6:
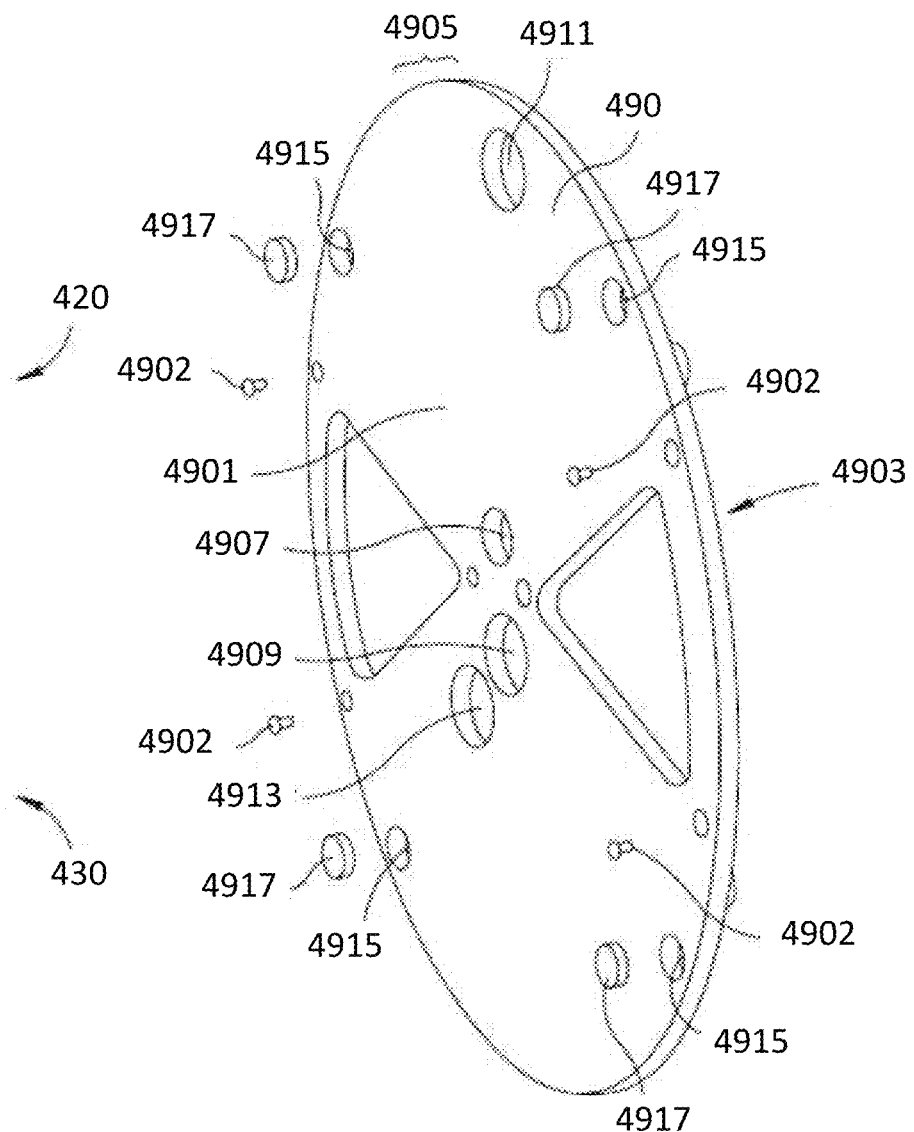
FIG. 6 is a perspective view of a lid of an over-ear earpiece or earset, according to an embodiment.

FIG. 6 is a perspective view of the lid 490 of the over-ear earpiece 401a. The lid 490 can be, for example, a part of the housing 452 of the over-ear earpiece 401a. As shown, the lid 490 of the over-ear earpiece 401a may include a first side 4901 and an opposing second side 4903 separated by a distance 4905, a cleaning agent aperture 4907, a discharge aperture 4909, a pump aperture 4911, a vacuum aperture 4913, and one or more coupling elements or features 4915.

The first side 4901 is oriented to face the cleaning agent reservoir 420 and the discharge collection reservoir 430. The second side 4903 is oriented to face the pan 480 and the cannula coupler interface 405. The cleaning agent aperture 4907 enables the cleaning agent to pass from the cleaning agent reservoir 420 to the cannula 410, as depicted in FIG. 4. The discharge aperture 4909 enables the discharge to pass from the cannula 410 to the discharge collection reservoir 430. The pump aperture 4911 enables the output of the pump assembly 424, located on the second side 4903 of the lid 490, to be physically coupled to the cleaning agent reservoir 420, located on the first side 4901 of the lid 490. The vacuum aperture 4913 enables the vacuum assembly 426, located on the second side 4903 of the lid 490, to be physically mated with the discharge collection reservoir 430, located on the first side 4901 of the lid 490. The coupling features 4915 may be used to secure the cleaning agent reservoir 420 or the discharge collection reservoir 430 to the lid 490. In some implementations, the coupling features 4915 may include, for example, a magnet 4917 for interfacing with a corresponding magnet (e.g., of opposing polarity) attached to the cleaning agent reservoir 420 or the discharge collection reservoir 430. The use of magnets such as the magnet 4917 may enable and facilitate user-friendly coupling and decoupling of the cleaning agent reservoir 420 or the discharge collection reservoir 430 from the over-ear earpiece 401a by the user. In other embodiments, the coupling features 4915 can include, for example, mechanical fastening elements (e.g., a screw, a bolt, a clamp, a latch, a hook and loop fastener, etc.) or an adhesive. In some embodiments, the coupling between the fluid reservoir 420 and/or discharge reservoir 430 can be via a friction fit between mating components of the fluid reservoir 420 and/or discharge reservoir 430 and one or more elements of the housing 452.

Figure 7:
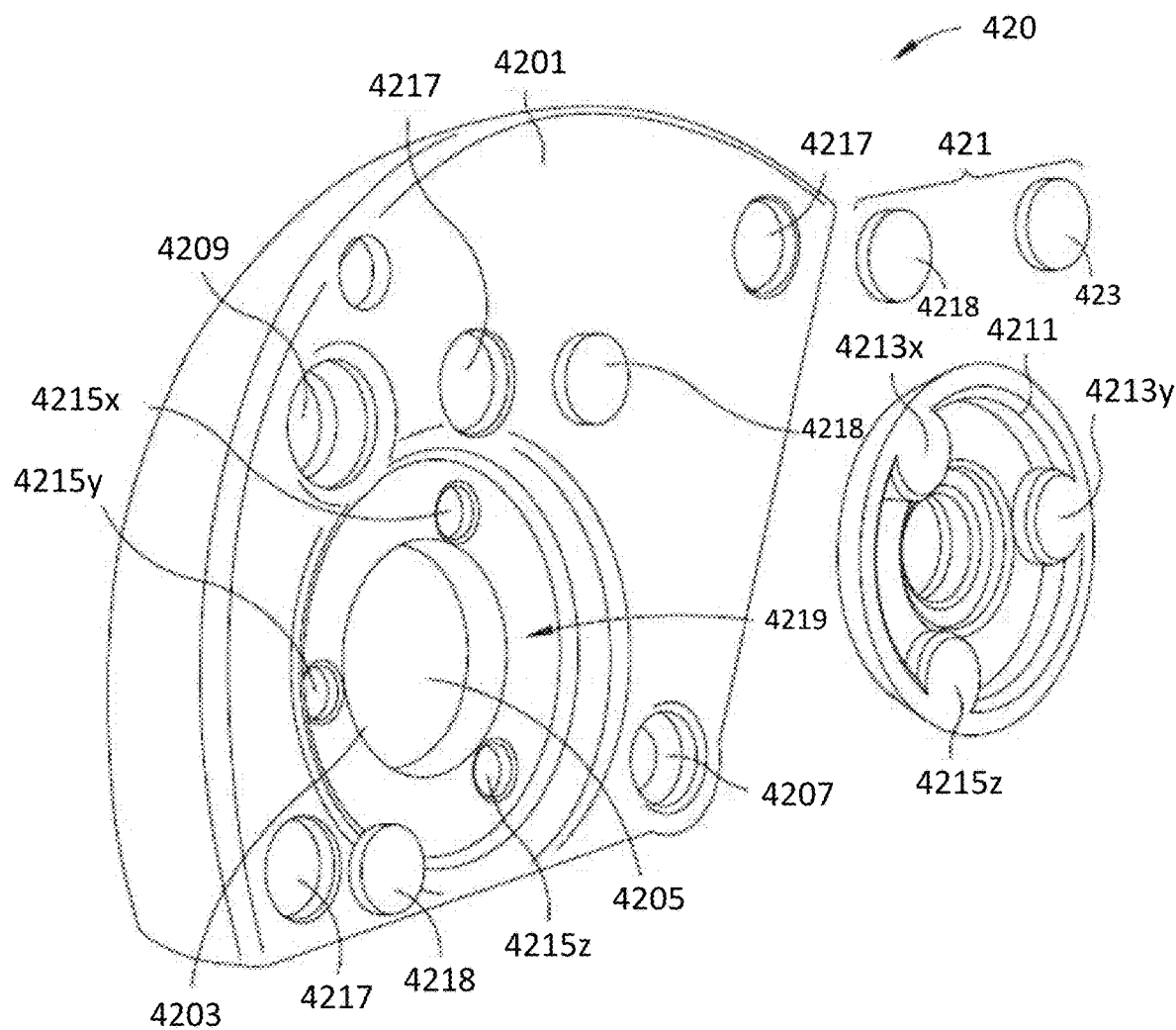
FIG. 7 is a perspective view of a cleaning agent reservoir of an over-ear earpiece or earset, according to an embodiment.

FIG. 7 is a perspective view of the fluid reservoir or cleaning agent reservoir 420 of the over-ear earpiece 401a. As shown, the cleaning agent reservoir 420 of the over-ear earpiece 401a may include a shell 4201 having an enclosed space 4203 for containing a supply of cleaning agent.

The enclosed space 4203 may include a volume sufficient to contain a supply of liquid and/or cleaning agent for performing at least one irrigation procedure (e.g., for one of a user's auditory canals) or at least two irrigation procedures (e.g., one for each of a user's auditory canals). In some implementations, the volume may be, for example, approximately 100 milliliters (e.g., to provide for capacity to contain 100 milliliters of cleaning agent).

The shell 4201 may include one or more coupling features 4217, and further, apertures such as a loading aperture 4205, a cleaning agent port 4207, and a pressure aperture 4209. The coupling features 4217 may be configured to couple with the corresponding coupling features 4915 of the lid 490, as described with reference to FIG. 6. In some implementations, the coupling features 4217 may include magnetic or ferromagnetic couplers 421, formed by magnetic coupling between a magnet 4218 and a magnet 423, as shown in FIG. 7. The magnetic couplers 421 may be used to magnetically couple the shell 4201 to the housing 452. In other embodiments, as described above, the coupling between the fluid reservoir 420 and the housing 452 can be via a different or additional mechanism, such as, for example, a mechanical fastening system, an adhesive, or a friction fit.

The loading aperture 4205 may be used to load the cleaning agent into the enclosed space 4203. In some implementations, the loading aperture 4205 may be mated with and sealed by a cleaning agent cover 4211. In some implementations, the cover 4211 may include one or more magnets 4213x, 4213y, and 4213z that magnetically couple to corresponding magnets 4215x, 4215y, and 4215z of the opposite polarity, thus providing multiple pairs of ferromagnetic couplers spaced proximate the edge of the loading aperture 4205. Alternatively or in addition, in some implementations, the loading aperture 4205 and the cleaning agent cover 4211 may have complementary threads that enable the cleaning agent cover 4211 to be screwed into the loading aperture 4205. In some implementations, the cover 4211 may include a protrusion that is sized and shaped for press fit with a corresponding slot or opening proximate the edge of the loading aperture 4205, as shown in FIG. 7. In some implementations, such a protrusion for the cover 4211 may be sized and shaped for press fit inside the loading aperture 4205 itself. A flexible, elastic sealing material (e.g., an O-ring) may be placed about the portion of the cover 4211 adjacent to the edge of the loading aperture 4205 to form a hermetic seal. As such, in some implementations, the cleaning agent reservoir 420 may be formed by the shell 4201 and the cleaning agent cover 4211. In some implementations, the loading aperture 4205 may be disposed inside a depression or well 4219 of the shell 4201. As shown in FIG. 7, when the cleaning agent cover 4211 is attached to the shell 4201, the cleaning agent cover 4211 may be disposed at or below a plane (not depicted) defined by the face of the shell 4201 to which the cleaning agent cover 4211 attaches, so as to avoid impeding or otherwise interfering with the magnetic coupling of the magnetic couplers 421.

In some implementations, the cleaning agent port 4207 may be sized and shaped to mate with the opening 4812 of the cleaning agent passage 4817 (see FIG. 5B), which may extend through the housing 452, to thereby provide, for the cleaning agent, a point of egress from the enclosed space 4205.

In some implementations, the pressure aperture 4209 may be configured to mate to an output of the pump assembly 424 (see FIG. 4). In such implementations, the pump assembly 424 may be used to apply pressure to the cleaning agent in the enclosed space 4203 to move the cleaning agent through the cleaning agent port 4207. In some implementations, the pump assembly 424 may include pump configured to draw the cleaning agent from the cleaning agent port 4207 and along the cleaning agent passage 4817 at a preset pressure and/or preset flow rate. In such implementations, the cleaning agent reservoir 420 may not include the pressure aperture 4209.

Figure 8:
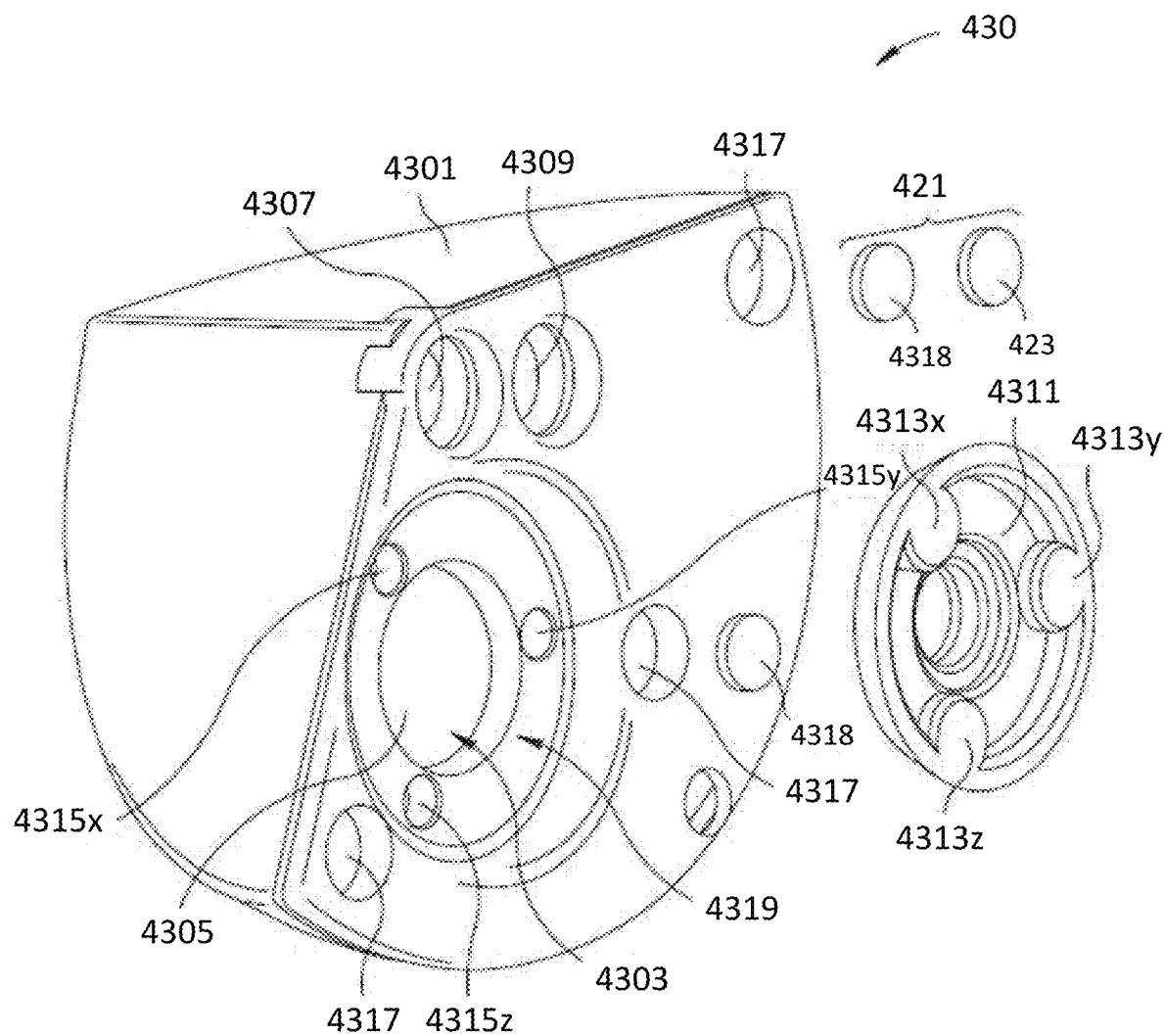
FIG. 8 is a perspective view of a discharge reservoir of an over-ear earpiece or earset, according to an embodiment.

FIG. 8 is a perspective view of the discharge reservoir 430 of the over-ear earpiece 401a. As shown, the discharge reservoir 430 of the over-ear earpiece 401a may include a shell 4301 having an enclosed space 4303 for containing applied and subsequently discharged cleaning agent from irrigation. The enclosed space 4303 may include a volume greater than (e.g., slightly greater than) that of the enclosed space 4203 (of the cleaning agent reservoir 420), e.g. to accommodate ear wax and other substances that may accompany the cleaning agent when discharged from a user's ear canal EC.

The shell 4301 may include one or more coupling features 4317, and further, apertures such as a discharge removal aperture 4305, a discharge port 4307, and a vacuum aperture 4309. The coupling features 4317 may be configured to couple with the corresponding coupling features 4915 of the lid 490, as described with reference to FIG. 6. In some implementations, the coupling features 4317 may include magnetic or ferromagnetic couplers 421, formed by magnetic coupling between a magnet 4318 and a magnet 423, as shown in FIG. 8. The magnetic couplers 421 may be used to magnetically couple the shell 4301 to the housing 452 in a manner similar to that described with reference to FIG. 7. The magnetic couplers 421 may be used to magnetically couple the shell 4301 and the discharge collection reservoir 430 to the housing 452. In other embodiments, as described above, the coupling between the discharge reservoir 430 and the housing 452 can be via a different or additional mechanism, such as, for example, a mechanical fastening system, an adhesive, or a friction fit.

In some implementations, the shell 4301 for the cleaning agent and the shell 4301 of the discharge reservoir 430 may be independently coupled to the housing 452. In such implementations, each of the cleaning agent shell 4201 and the discharge shell 4301 may be independently attached and detached from the housing 452.

The discharge removal aperture 4305 may be used to remove the discharge from the enclosed space 4303. In some implementations, the discharge removal aperture 4305 may be mated with and sealed by a discharge cover 4311. In some implementations, for example, the discharge cover 4311 may include one or more magnets 4313$x$, 4313$y$, and 4313$z$ that magnetically couple to corresponding magnets 4315$x$, 4315$y$, and 4315$z$ of the opposite polarity, thus providing multiple pairs of ferromagnetic couplers spaced proximate the edge of the discharge removal aperture 4305. Alternatively or in addition, the discharge removal aperture 4305 and the discharge cover 4311 may have complementary threads that enable the discharge cover 4311 to be screwed into the discharge removal aperture 4305. In some implementations, the discharge cover 4311 may include a protrusion that is sized and shaped for press fit with a corresponding slot or opening proximate to the edge of the discharge removal aperture 4305. In such implementations, such a protrusion for the discharge cover 4311 may be sized and shaped for press fit inside the discharge removal aperture 4305 itself. A flexible, elastic sealing material (e.g., an O-ring) may be placed about the portion of the cover 4311 adjacent to the edge of the discharge removal aperture 4305 to form a hermetic seal. As such, in some implementations, the discharge collection reservoir 430 may be formed by the shell 4301 and the discharge cover 4311. In some implementations, the discharge removal aperture 4305 may be disposed inside a depression or well 4319 of the shell 4301. Accordingly, when the discharge cover 4311 is secured in the shell 4301, it may be at or below a plane formed by the side of the shell 4301 to which the discharge cover 4311 attaches. As such, the discharge cover 4311 may not impede or interfere with the magnetic coupling of the ferromagnetic couplers. As shown in FIG. 8, when the discharge cover 4311 is attached to the shell 4301, the discharge cover 4311 may be disposed at or below a plane (not depicted) defined by the face of the shell 4301 to which the discharge cover 4311 attaches, so as to avoid impeding or otherwise interfering with the magnetic coupling of the magnetic couplers 421.

In some implementations, the discharge port 4307 may be sized and shaped to mate with the opening 4814 of the discharge passage 4819, which may extend through the housing 452 (see FIG. 4), to thereby provide, for the applied and subsequently discharged cleaning agent, a point of entry into the enclosed space 4303.

In some implementations, a vacuum aperture 4309 may be configured to mate to an output of the vacuum assembly 426 (see FIG. 4). In such implementations, the vacuum assembly 426 may be used to form an area of low pressure inside the enclosed space 4303, to draw the discharge from the discharge port 4307 to the enclosed space 4303. The negative pressure applied by the vacuum assembly 426 may be limited to maintain comfort and/or safety of the user. In some implementations, the upper limit of the negative pressure applicable by the vacuum assembly 426 may be less than about 100 kPa (approximately 0.986 atmospheres).

Figure 9:
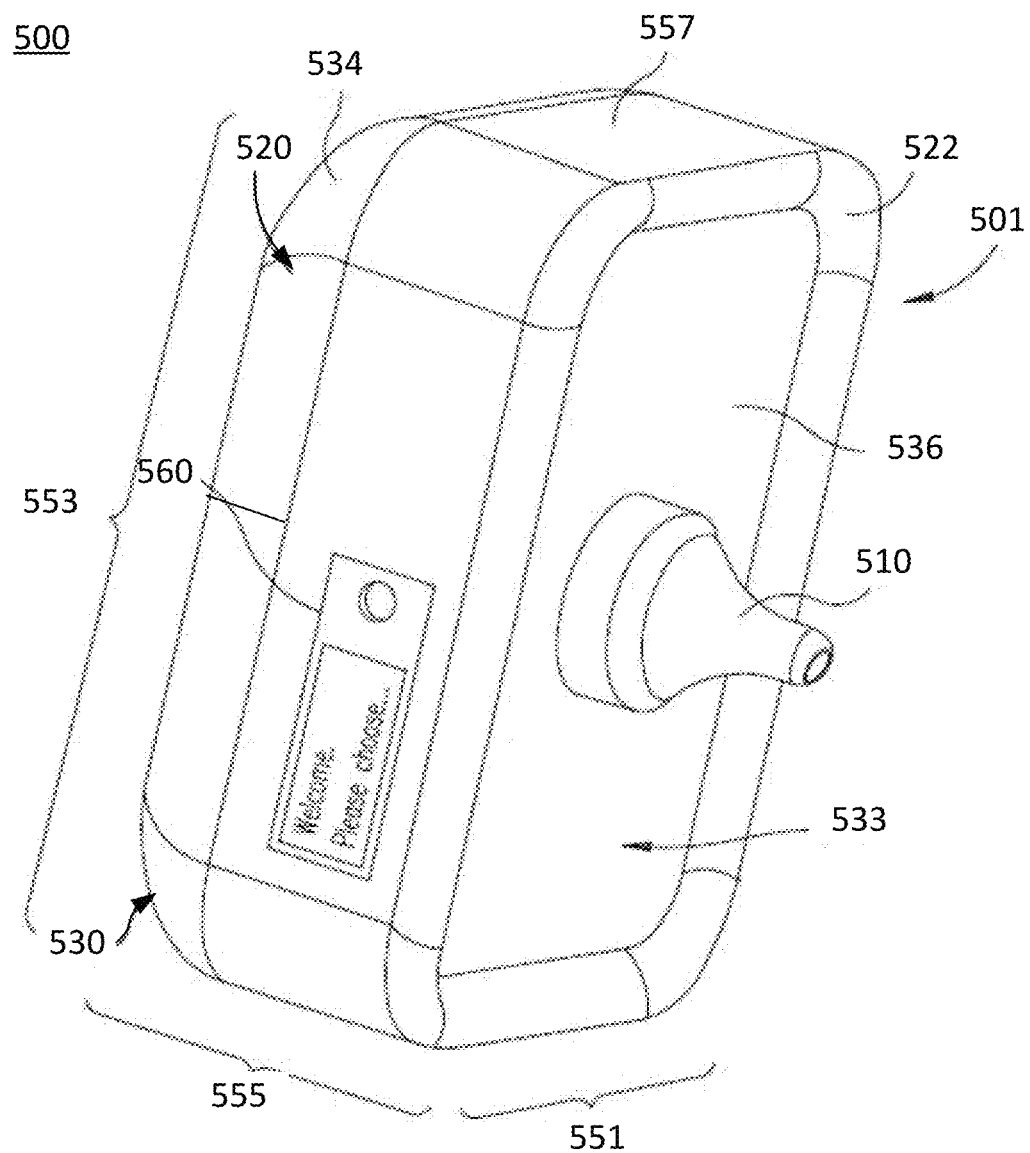
FIG. 9 is a perspective view of an over-ear earpiece or earset of an ear cleaning or irrigation device, according to an embodiment.

FIG. 9 is a perspective view of an earpiece 501 of an ear cleaning or irrigation device 500, according to an embodiment. The irrigation device 500 can include components that are structurally and/or functionally similar to other irrigation devices described herein. In an embodiment, the earpiece 501 can be designed to fit over an auricle of a user. As shown, the irrigation device 500 may be of rectangular shape and form. The earpiece 501 may include a delivery element implemented as a cannula 510, a fluid reservoir or cleaning agent reservoir 520, a discharge reservoir 530, and a user interface 560. Further, the earpiece 501 may include an interior side 536 and an exterior side 534 connected by one or more side walls 557, and having dimensions defined by a width 551, height 553, and depth 555. While shown and described with reference to the irrigation device 500, those having ordinary skill in the art will appreciate that the earpiece 501 may additionally or alternatively be configured for use with any of the irrigation devices as described herein.

In some implementations, the exterior side 534 may include a shell that forms part of a support element. The support element can include a unitary reservoir housing ("reservoir housing" or "unitary housing" or "unitary reservoir housing"). The reservoir housing may be configured to contain the cleaning agent reservoir 520 and the discharge reservoir 530 in spaced apart spatial relation, and further, may be configured for attachment to the earpiece 501 by attachment of the exterior side 534 to the earpiece 501, to enable fluid communication between the cannula 510, the cleaning agent reservoir 520, and the discharge reservoir 530, as described in further detail with reference to FIGS. 10A-10C.

In some implementations, the over-ear earpiece 501 may include a user interface 560. For example, the user interface 560 may be disposed along one of the side walls 557, as shown in FIG. 9. In some implementations, the user interface 560 may include one or more user interface components such as buttons, switches, LEDs, touch screens, or the like. For example, the user interface components may be configured to receive user selections and commands from a user with respect to irrigation procedures and operations, display operation status updates to the user, and the like.

In some implementations, a length of the depth 555 may be less than a length of the width 551, and the length of the width 551 may be less than a length of the height 553. Such dimensions may provide a more streamlined fit and appearance when compared to over-ear earpieces of other shapes. When placed over an ear of a user, the height 553 may be oriented vertically with the interior side 536 adjacent to the side of the face of the user, perpendicular to the ground when the user wearing the irrigation device 500 is in an upright position. The cannula 510 may be disposed substantially in the center of the interior side 536, to facilitate positioning of the cannula 510 within the auditory canal of the user when the user is wearing the irrigation device 500 with the earpiece 501. The earpiece 501 may include an annular membrane 522 that extends about the perimeter of the interior side 536. The annular membrane 522 may form a cavity 533 that may be sized and dimensioned to receive ears (e.g., auricles) of various sizes.

Figure 10A:
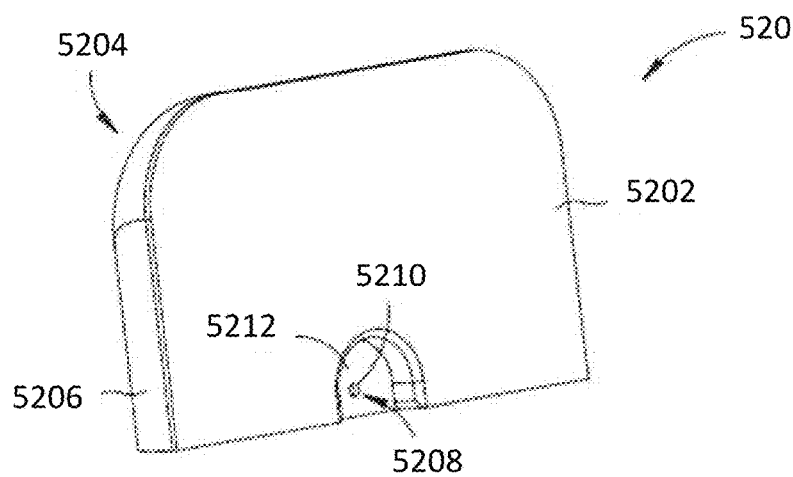
FIG. 10A is a perspective view of a fluid reservoir of the over-ear earpiece depicted in FIG. 9, according to an embodiment.

FIG. 10A is a perspective view of the fluid reservoir or cleaning agent reservoir 520 of the irrigation device 500, according to an embodiment. As shown, the cleaning agent reservoir 520 may include a front face 5202 and a back face 5204 separated by one or more side walls 5206. In some implementations, the front face 5202 and the back face 5204 may be oriented substantially parallel to each other and perpendicular to the one or more side walls 5206, each of which may span separation or distance between the front face 5202 and the back face 5204. In some implementations, the front face 5202 and the back face 5204 may meet at an edge such that the back face 5204 curves outward from the front face 5202 and/or the front face 5202 curves outward from the back face 5204. In such implementations, a cross-sectional area of the cleaning agent reservoir 520 may include or be defined by an arc along one or both of the sides associated with the back face 5204 and the front face 5202.

The front face 5202, the back face 5204, and the side walls 5206 (when present) may define a hollow space 5208 for the cleaning agent reservoir 520, with each of the front face 5202, the back face 5204, and the side walls 5206 delineating a boundary for the hollow space. In some implementations, the hollow space 5208 may be accessible via a cleaning agent reservoir port 5210 located within a depression 5212 located on the front face 5202 of the cleaning agent reservoir 520. The cleaning agent reservoir port 5210 may be sized and dimensioned to selectively, detachably, physically mate with other components of the irrigation device such that the port 5210 is in fluid communication with a cleaning fluid fluidly communicative path that connects to the cannula 510, e.g., via an opening 5348a defined by a tubular element or collar 5348. When the cleaning agent reservoir port 5210 is in fluid communication with the cleaning fluid fluidly communicative path, the cleaning agent reservoir 520 may provide cleaning agent for one or more irrigation procedures. In some implementations, the cleaning agent reservoir port 5210 may be fluidly coupled to a pump assembly (e.g., a pump assembly 124). In some implementations, the cleaning agent reservoir port 5210 may be sealed with a flexible, elastic membrane during a manufacturing and/or assembly process after cleaning agent has been placed into the hollow space 5208 of the cleaning agent reservoir 520. In such implementations, the irrigation device 500 can include a puncturing edge or element (e.g., a sharp edge disposed at a tip of the tubular element or collar 5438 facing the fluid reservoir 520) that can puncture the membrane to thereby access the cleaning fluid when the disposable cleaning agent reservoir 520 is mounted onto the earpiece 501. The hollow space 5208 of the fluid reservoir 520 can be pre-pressurized such that when the membrane is punctured, the fluid (e.g., including cleaning agent) within the hollow space 5208 can exit the hollow space 5208 in response to a release of the pressure. In some embodiments, the puncturing edge or element can be movable, e.g., in response to an input received via the user interface 560, to puncture the membrane.

The fluid reservoir or cleaning agent reservoir 520 may be made of any suitable plastic materials, such as, for example, plastic material that is approved for use in medical procedures. Alternatively or additionally, portions of the cleaning agent reservoir 520 can be made from one or more of a textile, paper, metal, or any other material accepted for use in a medical environment. In some embodiments, the cleaning agent reservoir 520 can be disposable, e.g., for one-time use. For example, in some implementations, the cleaning agent reservoir 520 may hold sufficient cleaning agent to perform one (1) irrigation cycle of an irrigation routine. Such an irrigation cycle may be sufficient for cleaning one ear of a human user, for example. Accordingly, such a cleaning agent reservoir 520 may be changed out after every use, thereby reducing the number of components of the irrigation device 500 exposed to multiple users and/or requiring cleaning or sanitization between uses. Alternatively, the cleaning agent reservoir 520 can be designed for multiple uses. In some implementations, as discussed below with reference to FIG. 10D, the cleaning agent reservoir 520 may be mounted directly onto the earpiece 501 using one or more fasteners or physical couplers. In some implementations, as discussed below with reference to FIG. 10C, the cleaning agent reservoir 520 may be loaded into a shell and mounted on the over-ear earpiece 501 when the shell is attached to the earpiece 501.

Figure 10B:
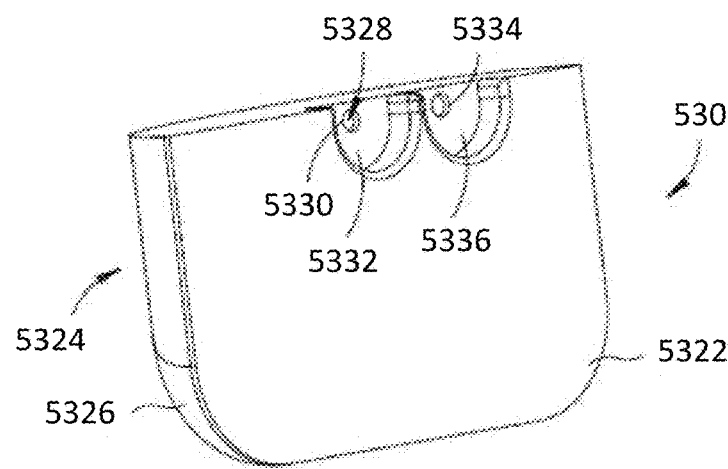
FIG. 10B is a perspective view of a discharge collection reservoir of the over-ear earpiece depicted in FIG. 9, according to an embodiment.

FIG. 10B is a perspective view of the discharge reservoir or discharge collection reservoir 530 of the irrigation device 500, according to an embodiment. As shown, the discharge collection reservoir 530 may include a front face 5322 and a back face 5324. In some implementations, the front face 5322 and the back face 5324 may be substantially parallel to each other. In such implementations, the discharge collection reservoir 530 may include the one or more side walls 5326 that bridge the distance between the front face 5322 and the back face 5324. In some implementations, the front face 5322 and the back face 5324 may meet at an edge such that the back face 5324 curves outward from the front face 5322 and/or the front face 5322 curves outward from the back face 5322. In such an implementation, a cross-sectional area of the discharge collection reservoir 530 may include an arc along one or both of the sides associated with the back face 5324 and the front face 5322.

The front face 5322, the back face 5324, and the side walls 5326 (when present) may define a hollow space 5328 for the discharge collection reservoir 530, with each of the front face 5322, the back face 5324, and the side walls 5326 delineating a boundary for the hollow space 5328. In some implementations, the hollow space 5328 may be accessible via a discharge collection reservoir port 5330 located within a first depression 5332 located on the front face 5322 of the discharge collection reservoir 530. The discharge collection reservoir port 5330 may be sized and dimensioned to selectively, detachably, physically mate with other components of the irrigation device 500 such that the port 5330 is in fluid communication with a discharge fluidly communicative path that connects to the cannula 510, e.g., via an opening 5340a defined by a tubular element or collar 5340. When the discharge collection reservoir port 5330 is in fluid communication with the discharge fluidly communicative path, the discharge collection reservoir 530 may be used to collect discharge during one or more irrigation procedures. In some implementations, the discharge collection reservoir port 5330 may be sealed with a flexible membrane during a manufacturing and/or assembly process. In some implementations, the irrigation device 500 can include a puncturing edge or element (e.g., a sharp edge disposed at a tip of the tubular element or collar 5340) that can puncture the membrane to thereby providing access to the hollow space 5328 of the discharge collection reservoir 530 when the disposable discharge collection reservoir 530 is mounted onto the over-ear earpiece 501. In some embodiments, the hollow space 5328 of the discharge reservoir 530 can be preset to have a lower pressure than an atmospheric pressure or environmental pressure such that when the membrane is punctured, the lower pressure within the discharge reservoir 530 can act to draw fluid (e.g., including cleaning agent and/or substances from within a user's ear canal EC) into the discharge reservoir 530.

Alternatively or additionally, the front face 5322 of the disposable discharge collection reservoir 530 may include a vacuum assembly port 5334 that may provide access to the hollow space 5328 of the disposable discharge collection reservoir 530. The vacuum assembly port 5334 may be located within a second depression 5336 on the front face 5322 of the disposable discharge collection reservoir 530.

The vacuum assembly port 5334 may be sized and dimensioned to physically, fluidly couple with a vacuum assembly (e.g., a vacuum assembly 126) when the disposable discharge collection reservoir 530 is mounted onto the earpiece 501. The vacuum assembly may be used to create a vacuum or area of low pressure within the disposable discharge collection reservoir 530 to facilitate the removal of the discharge from the auditory canal during and/or after an irrigation procedure.

The discharge collection reservoir 530 may be made of any suitable plastic materials, such as, for example, plastic material that is approved for use in medical procedures. Alternatively or additionally, portions of the discharge reservoir 530 can be made from one or more of a textile, paper, metal, or any other material accepted for use in a medical environment. In some embodiments, the discharge reservoir 530 can be disposable, e.g., for one-time use. For example, in some implementations, the hollow space 5328 of the disposable discharge collection reservoir 530 may hold sufficient volume to contain discharge from at least one (1) irrigation cycle of an irrigation routine. Such an irrigation cycle may be sufficient for cleaning one ear of a human user, for example. Accordingly, such a discharge collection reservoir 530 may be changed out after every use, thereby reducing the number of components of the irrigation device 500 exposed to multiple users and/or requiring cleaning or sanitization between uses. Alternatively, the discharge reservoir 530 can be designed for multiple uses and can be designed to be cleaned between uses and/or capable of containing discharge for multiple cleaning routines. In some implementations, the discharge collection reservoir 530 may be mounted directly onto the earpiece 501 using one or more fasteners or physical couplers. In some implementations, as discussed below, the discharge collection reservoir 530 may be loaded into a shell and mounted on the over-ear earpiece 501 when the shell is attached to the earpiece 501.

Figure 10C:
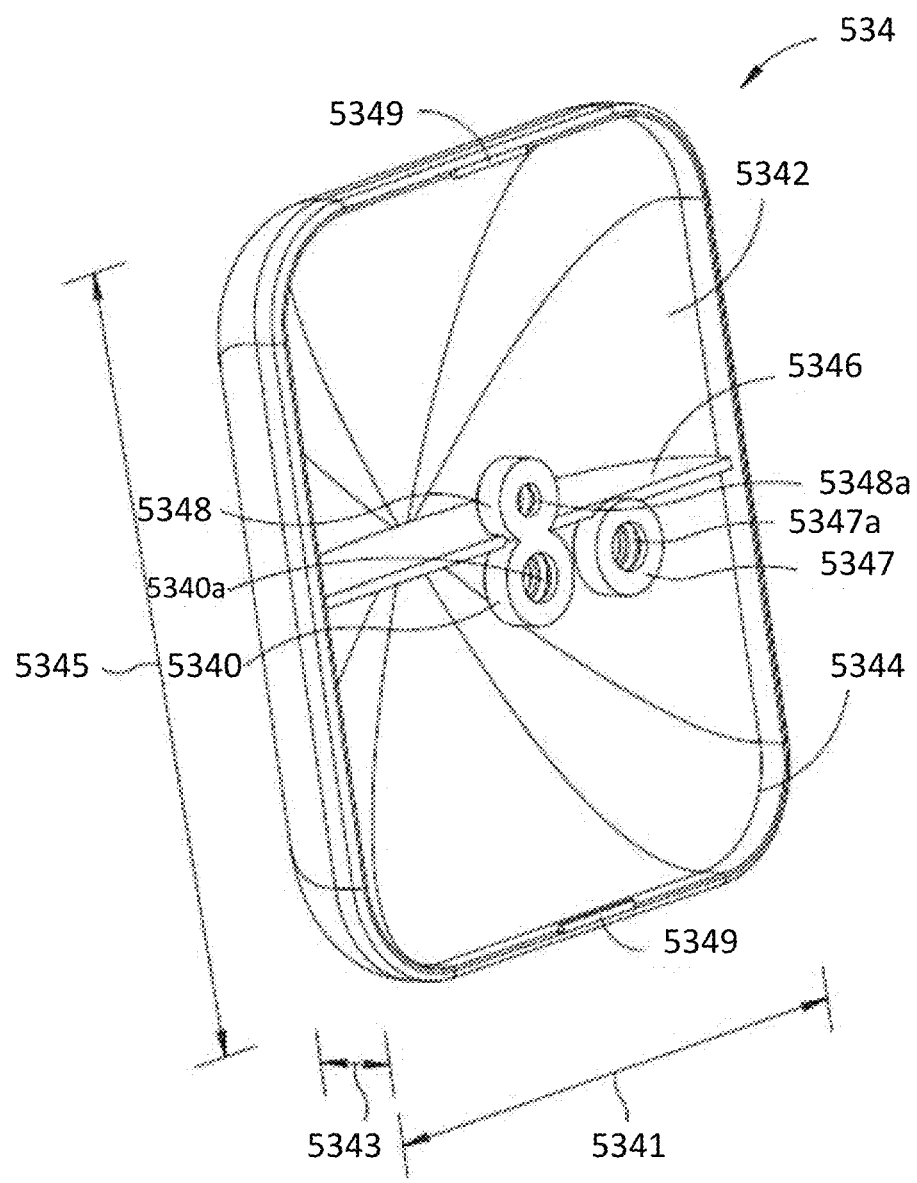
FIG. 10C is a perspective view of an interior of a reservoir housing defined by a shell of an exterior side of the over-ear earpiece depicted in FIG. 9, according to an embodiment.

FIG. 10C is a perspective view of an interior of the reservoir housing defined by the shell of the exterior side 534 of the irrigation device 500, according to an embodiment. As shown, the reservoir housing may be defined by a shell of the exterior side 534, which may be dimensioned in terms of a length 5341, width 5343, and height 5345. The shell of the exterior side 534 may be dimensioned in terms of a length 5341, a width 5343, and a height 5345, and may be sized for interfacing, attachment, and fit with a corresponding interface portion of the earpiece 501. The reservoir housing may include one or more interior walls or partitions 5346 spanning the width 5343, by which first and second cavities 5342 and 5344 may be defined, separated, and configured to contain the cleaning agent reservoir 520 and the discharge reservoir 530. In some implementations, the first and second cavities 5342 and 5344 may be sized and dimensioned to individually hold and enclose the cleaning agent reservoir 520 and the discharge collection reservoir 530, respectively, in a spaced apart spatial relation defined based on a thickness of the one or more interior walls or partitions 5346 of the reservoir housing.

In some implementations, the cleaning agent reservoir 520 and the discharge collection reservoir 530 may be disposable or recyclable. For example, the cleaning agent reservoir 520 or the discharge collection reservoir 530 may be made of any suitable disposable and/or recyclable materials (e.g., polymer, textile, paper, metal), and may be configured for removable insertion and mounting in the first and second cavities 5342 and 5344, respectively.

The reservoir housing 534 may include an interior wall or partition 5346 that spans the length 5341 and separates the first cavity 5342 from the second cavity 5344. A first collar 5348 may be attached to the interior wall 5346 and extend perpendicularly from the interior wall 5346 towards the first cavity 5342. The first collar 5348 may have an annular shape with an interior opening 5348*a*. In some implementations, the interior opening 5348*a* may align with the cleaning agent reservoir port 5210 when the cleaning agent reservoir 520 is loaded into the first cavity 5342. Such alignment may facilitate the mating of the cleaning agent reservoir port 5210 with the cleaning fluid fluidly communicative path.

In some implementations, the disposable cleaning agent reservoir 520 may be loaded into the first cavity 5342 by sliding the end of the cleaning agent reservoir 520 that has the cleaning agent reservoir port 5210 into the first cavity 5342 towards the interior wall 5346 and behind the first collar 5348. In some implementations, the reservoir housing 534 may optionally have a latch 5349 or other similar securing feature located along the edge of the first cavity 5342 opposite the interior wall 5346. The corresponding end of the cleaning agent reservoir 520 may be pressed into first cavity 5342 behind the latch 5349 to thereby secure the cleaning agent reservoir 520 in the first cavity 5342.

A second collar 5340 and a third collar 5347 may be attached to the interior wall 5346 and extend perpendicularly from the interior wall 5346 towards the second cavity 5344. The second collar 5340 may have an annular shape with an interior opening 5340*a*. In some implementations, the interior opening 5340*a* may align with the disposable discharge collection reservoir port 5330 when the discharge collection reservoir 530 is loaded into the second cavity 5344. Such alignment may facilitate the mating of the disposable discharge collection reservoir port 5330 with the discharge fluidly communicative path. The third collar 5347 may have an annular shape with an interior opening 5347*a*. In some implementations, the interior opening 5347*a* may align with an output from a vacuum assembly (e.g., vacuum element 126) when the discharge collection reservoir 530 is loaded into the second cavity 5344. Such alignment may facilitate the mating of the vacuum assembly port 5334 with the vacuum assembly.

In some implementations, the discharge collection reservoir 530 may be loaded into the second cavity 5344 by sliding the end of the discharge collection reservoir 530 that has the discharge collection reservoir port 5334 into the second cavity 5344 towards the interior wall 5346 and behind the second collar 5340 and/or third collar 5347. In some implementations, the reservoir housing 534 may optionally have a latch 5349 or other similar securing feature located along the edge of the second cavity 5344 opposite the interior wall 5346. The corresponding end of the discharge collection reservoir 530 may be pressed into second cavity 5344 behind the latch 5349 to thereby secure the discharge collection reservoir 530 in the second cavity 5344.

Figure 10D:
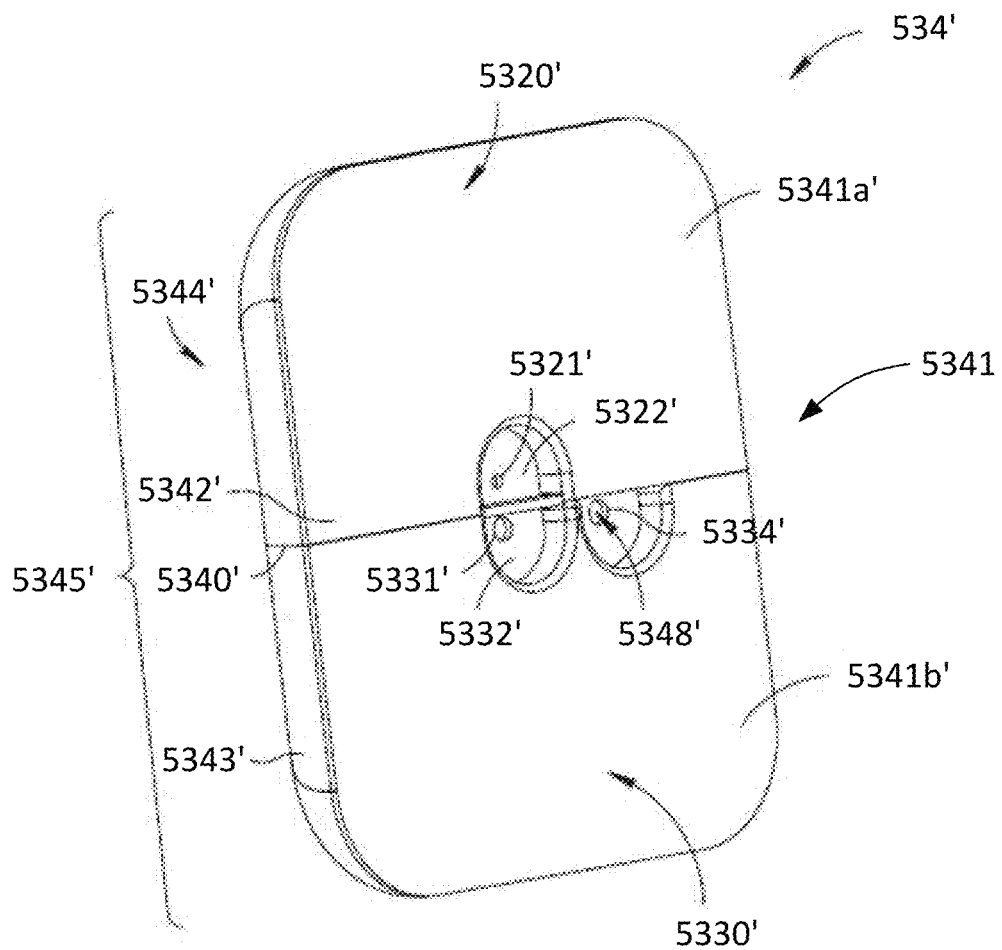
FIG. 10D is a perspective view of a unitary reservoir housing defined by a shell of an exterior side of the over-ear earpiece depicted in FIG. 9, according to an alternative embodiment.

FIG. 10D depicts an alternative implementation of a fluid reservoir 5320' and a discharge reservoir 5330', in which the fluid reservoir 5320' and the discharge reservoir 5330' are implemented as a single component or unit. For example, FIG. 10D depicts a unitary reservoir housing 534' defined by a shell of an exterior side of an irrigation device, such as the irrigation device 500. As shown, the unitary reservoir housing 534' defined by the shell of the exterior side may include a unitary body 5345', formed by a front face 5342', a back face 5344', and one or more side walls 5344'. In some implementations, the unitary reservoir housing 534' may be disposable and/or recyclable. For example, the unitary reservoir housing 534' may be partially or completely made of disposable and/or recyclable materials (e.g., polymer, textile, paper, metal, etc.). While described with reference to the irrigation device 500, it will be apparent to those of ordinary skill in the art that any of the aforementioned, as such may relate to the unitary reservoir housing, may be applied to any of the ear cleaning or irrigation devices as described herein.

In some implementations, the front face 5342' and the back face 5344' may be oriented substantially parallel to each other and substantially perpendicular to one or more of the side walls 5343', each of which may be disposed within the unitary housing 534' to span the distance between the front face 5342' and the back face 5344'. In some implementations, the front face 5342' and the back face 5344' may meet at an edge, such that the back face 5344' curves outward from the front face 5342' and/or the front face 5342' curves outward from the back face 5344'. In such implementations, a cross-sectional area of the unitary reservoir housing 534' may include an arc along one or both of the sides associated with the back face 5344' and the front face 5342'.

The front face 5342', the back face 5344', and the side walls 5344' (when present) may define a hollow space 5341' for the unitary reservoir housing 534', with each of the front face 5342', the back space 5344', and the side walls 5344' delineating a boundary for the hollow space 5341'. In some implementations, a partition 5340' may divide the hollow space 5341' into multiple sections 5341a', 5341b'. In such implementations, the different sections may be fluidly separated from each other such that the fluid contents of one section would not be able to travel directly within the unitary reservoir housing 534' to another section. For example, in some implementations, the hollow space 5341' may be divided into a cleaning agent reservoir section 5320' and a discharge collection reservoir section 5330', with such sections fluidly separated from the other within the unitary reservoir housing 534'.

In some implementations, the cleaning agent reservoir section 5320' may be accessible via a cleaning agent port 5321' located within a first depression 5322' on the front face 5342' of the unitary reservoir housing 534'. The cleaning agent port 5321' may be sized and dimensioned to selectively, detachably, physically mate with other components of the irrigation device (e.g., irrigation device 500) such that the cleaning agent port 5321' is in fluid communication with a cleaning fluid fluidly communicative path that connects to a cannula (e.g., cannula 510). When the unitary reservoir housing 534' is in fluid communication with the cleaning fluid fluidly communicative path, the cleaning agent reservoir section 5320' may provide cleaning agent for one or more irrigation procedures. In some implementations, the cleaning agent port 5321' may be sealed with a flexible membrane during a manufacturing and/or assembly process after cleaning agent has been placed into the cleaning agent reservoir section 5320' of the unitary reservoir housing 534'. In some implementations, the irrigation device can include a puncturing edge or element (e.g., a proximal end of the cannula 510, or a surface of an intermediate component facing the unitary housing 534') may be configured to puncture the membrane to thereby access the cleaning fluid when the unitary reservoir housing 534' is mounted onto other components of the irrigation device (e.g., the earpiece 501).

In some implementations, the discharge collection reservoir section 5330' may be accessible via a discharge collection reservoir port 5331' located within a second depression 5332' on the front face 5342' of the disposable container 534'. The discharge collection reservoir port 5331' may be sized and dimensioned to selectively, detachably, physically mate with other components of an irrigation device (e.g., irrigation device 500) such that the discharge collection reservoir port 5331' is in fluid communication with a discharge fluidly communicative path connected to a cannula (e.g., cannula 510). When the discharge collection reservoir port 5331' is in fluid communication with the discharge fluidly communicative path, the discharge collection reservoir section 5330' may be used to collect discharge during one or more irrigation procedures. In some implementations, the discharge collection reservoir section 5330' may be sealed with a flexible membrane during a manufacturing and/or assembly process. In some implementations, the irrigation device can include a puncturing edge or element (e.g., a proximal end of the cannula 510, or a surface of an intermediate component facing the unitary reservoir housing 534') may be configured to puncture the membrane to thereby access the discharge collection reservoir section 5330' when the unitary reservoir housing 534' is mounted onto other components of the irrigation device (e.g., the earpiece 501).

The front face 5342' of the unitary reservoir housing 534' may include a vacuum assembly port 5334' that may provide access to the discharge collection reservoir section 5330'. The vacuum assembly port 5334' may be located within a third depression 5348' on the front face 5342' of the disposable container 534'. The vacuum assembly port 5334' may be sized and dimensioned to physically, fluidly couple with a vacuum assembly (e.g., vacuum assembly 126) when the unitary reservoir housing 534' is mounted onto other components of the irrigation device (e.g., the earpiece 501). The vacuum assembly may be used to create a vacuum or area of low pressure within the discharge collection reservoir section 5330' to facilitate the removal of the discharge from the auditory canal during and/or after an irrigation procedure.

The unitary reservoir housing 534' may be made of any suitable plastic material such as plastic material approved for use in medical procedures (e.g., a medical plastic), or other types of materials (e.g., a polymer, a paper, a textile, a metal, or any composite material). In some implementations, the cleaning agent reservoir section 5330' of the unitary reservoir housing 534' may hold sufficient volume to contain discharge from at least one (1) irrigation cycle of an irrigation routine. In some implementations, the discharge collection reservoir section 5330' may hold sufficient volume to contain discharge from at least one (1) irrigation cycle of an irrigation routine. Such an irrigation cycle may be sufficient for cleaning one ear of a human user, for example. Accordingly, such a unitary reservoir housing 534' may be changed out after every use, thereby reducing the number of components of the irrigation device 500 exposed to multiple users. In some implementations, the unitary reservoir housing 534' may be mounted directly onto other components of the irrigation device (e.g., the earpiece 501) using one or more fasteners or physical couplers. In some implementations, the unitary reservoir housing 534' may be loaded into a shell (e.g., a reservoir housing 534 without interior wall 5346) and mounted on the other components when the shell is attached to those other components.

Figure 11:
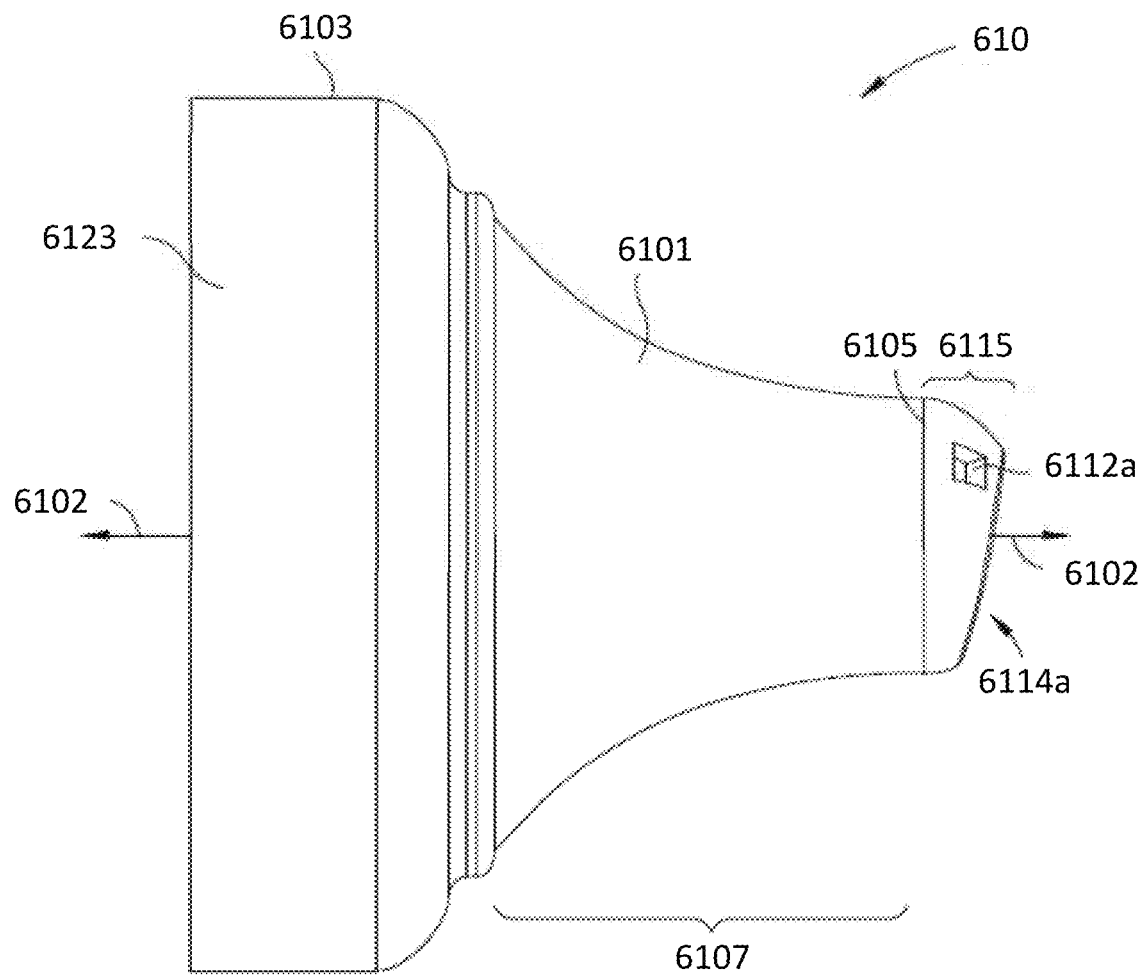
FIG. 11 is a side view of a cannula which may be used with or as part of an irrigation device, according to an embodiment.
Figure 12:
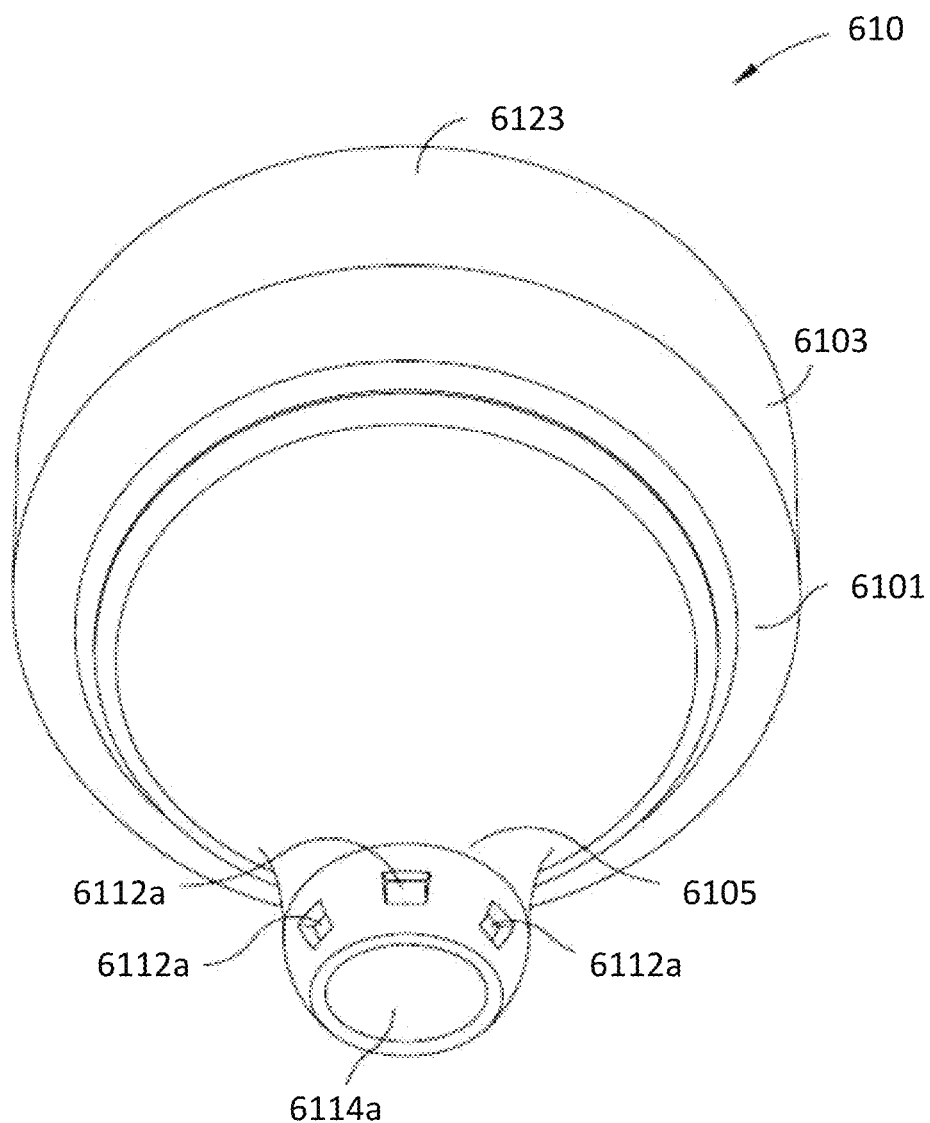
FIG. 12 is a perspective view of the cannula of FIG. 11, showing the tip from which cleaning agent exits and discharge enters the cannula, according to an embodiment.
Figure 13:
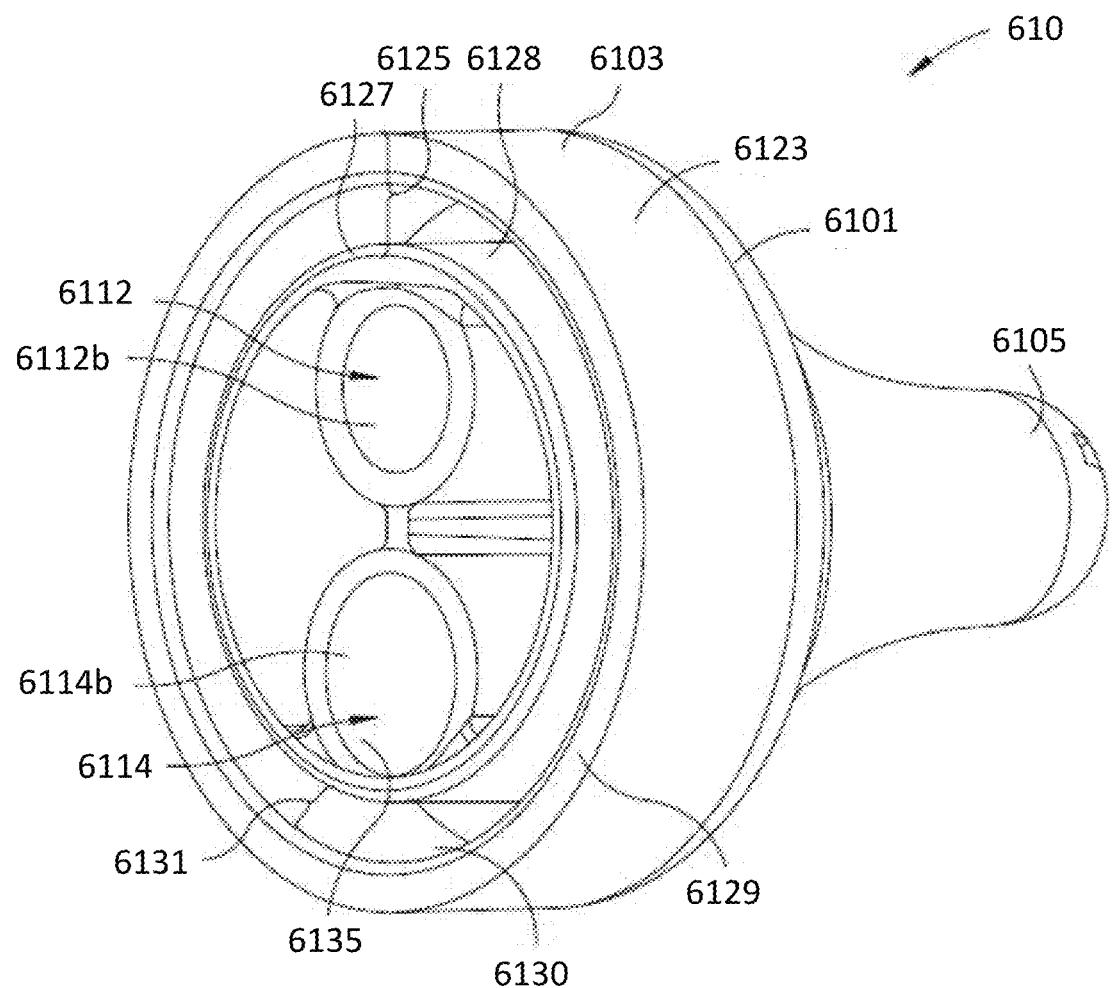
FIG. 13 is a rear, side view of the cannula of FIG. 11, according to an embodiment.
Figure 14:
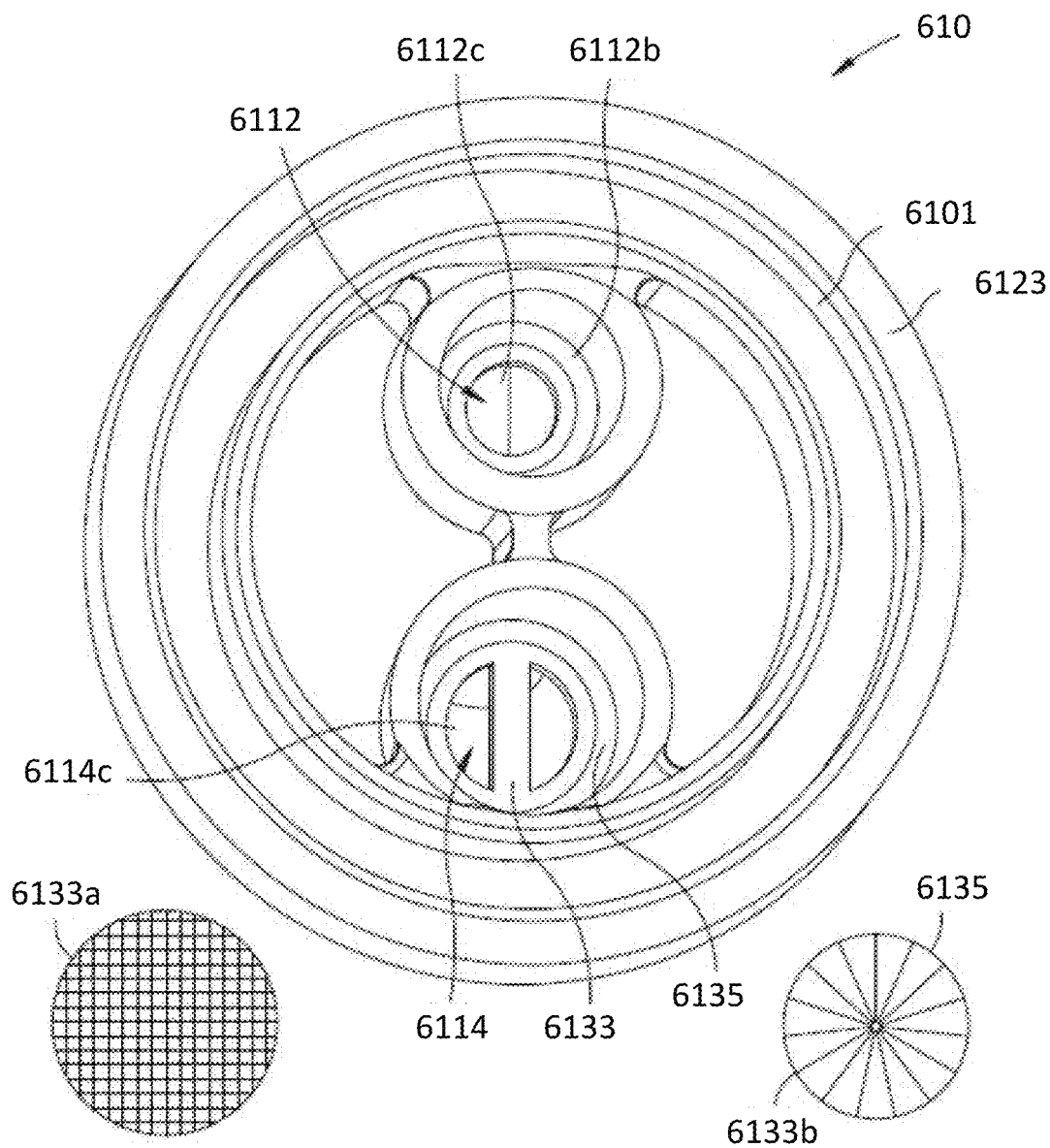
FIG. 14 is a rear view of the cannula of FIG. 11, which includes an interface that is used to couple the cannula to a cannula coupler interface on the over-ear earpieces, according to an embodiment.

FIG. 11 is a side view of a delivery element implemented as a cannula 610, which may be used with or as part of an irrigation device (e.g., any of the irrigation devices 100, 200, 300, 400, 500, etc.), according to an embodiment. FIG. 12 is a front, side isometric view of the cannula 610, showing the tip from which cleaning agent exits and discharge enters the cannula 610. FIG. 13 is a rear, side isometric view of the cannula 610. FIG. 14 is a rear plan view of the cannula 610, which includes an interface that is used to couple the cannula to a cannula coupler interface on the over-ear earpieces. As shown, the cannula 610 includes a body 6101 having a proximal end 6103 and a distal end 6105 separated by and opposing each other across a length 6107.

In some implementations, the body 6101 may taper from the proximal end 6103 towards the distal end 6105, such that a cross-sectional area of the proximal end 6103 is greater than a cross-sectional area of the distal end 6105, which is inserted into the user's auditory canal. In such implementations, the tapering of the cannula 610 may protect a user's ear drum by having a relatively larger portion of the body 6101 impact a side wall of the user's auditory canal and/or auricle before the distal end 6105 of the cannula 610 impacts the user's ear drum. In some embodiments, the tapering of the cannula 610 can be designed so as to position the distal end 6105 of the cannula 610 at a predetermined depth within the auditory canal. In some implementations, the body 6101 may have a partially conical shape, such as a frustro-conical shape in which the tapered end of the cone has been truncated, as shown in FIG. 11. In some implementations, the tapering of the body 6101 may be linear and/or include sections with different tapering profiles (e.g., a first section with a more progressive taper than a second section). In some implementations, the tapering of the body 6101 may be non-linear, with a curve and/or steps in the profile as traversed from base to tip. In some implementations, the tapering may be linear over some portion of the body 6101 and non-linear over other portions of the body 6101. In some implementations, the body 6101 may be formed of a unitary single-piece of plastic. In other implementations, the body 6101 may be formed of a plurality of pieces that have been joined together. In some implementations, the body 6101 may have a form that is a body of rotation about a central axis 6102. In some implementations, the body 6101 may not be in the form of a body of rotation.

One or more irrigation outlet apertures 6112a may be located at the distal end 6105. In some implementations, one or more of the irrigation outlet apertures 6112a may be set back a short distance (e.g., up to 5 mm) from a distal edge of the distal end 6105. The irrigation outlet apertures 6112a may be used to direct an outward flow of cleaning agent that is exiting from the cannula 610. In some implementations, multiple irrigation outlet apertures 6112a may be radially spaced around the distal end 6105. In some embodiments, one or more irrigation outlet apertures 6112a can be located at different distances from a distal end of the distal end 6105. For example, one or more irrigation outlet apertures 6112a can be located on the body 6101 instead of the distal end, while other irrigation outlet apertures 6112a can be located at the distal end 6105. By varying the distance of the apertures 6112a from the distal end 6105, different fluid inflow profiles into the auditory canal that target different regions of the auditory canal can be achieved. For example, irrigation outlet apertures 6112a further from the distal edge of the distal end 6105 can be disposed a greater radial distance from a central axis 6102 of the cannula 610 and therefore target areas of auditory canal closer to the opening of the ear.

The irrigation outlet aperture 6112a may be located at the end of an irrigation passage 6112c that provides an irrigation flow path 6112 between an irrigation inlet port 6112b located at the proximal end 6103 of the cannula 610 and the irrigation outlet aperture 6112a located relatively towards the distal end 6105 with respect to the irrigation inlet port 6112b. The irrigation outlet apertures 6112a can have one or more shape and/or size profiles, including rectangular, cylindrical, etc. The irrigation inlet port 6112b may be substantially cylindrical in shape, or may have other shapes, for instance oval or elliptical.

A discharge collection inlet port 6114a may be located at, or at least proximate to, the distal end 6105 of the cannula 610. The discharge collection inlet port 6114a may be used to collect the discharge from the user's auditory canal during an irrigation procedure. In some implementations, a suction force may be created at the discharge collection inlet port 6114a via a vacuum or area of relatively low or negative air pressure created by a vacuum assembly (e.g., vacuum assembly 126), e.g., within and/or via a discharge collection reservoir (e.g., discharge reservoir 130). The suction force may assist in collecting the discharge. The discharge collection inlet port 6114a may be located at the end of a discharge flow path 6114 that provides a flow path for the discharge between the discharge collection inlet port 6114a located relatively towards the distal end 6105 of the cannula 610 and the discharge collection outlet port 6114b located at the proximal end 6103 of the cannula 610.

In some implementations, the irrigation inlet port 6112b is radially offset from the discharge collection outlet port 6114b, and one or both may be radially offset from the central axis 6102 of the cannula 610. In some implementations, the irrigation outlet apertures 6112a may be radially offset outwardly from the central axis 6102; such placement may result in the irrigation outlet apertures 6112a forming an arc. In some implementations, the discharge collection inlet port 6114a may be disposed about the central axis 6102.

In some embodiments, one or more traps 6133a, 6133b may be located along the discharge flow path 6114. The traps 6133a, 6133b may be or include a filter such as a sieve or sifter that extends at least partially across the discharge collection passage. The discharge collection passage may have an inside perimeter 6135, and in an embodiment, the trap (e.g., trap 6133b) may include a plurality of projections that extend radially inward from the inside perimeter of the discharge collection passage towards a central axis of the discharge collection passage 6114. The traps 6133a, 6133b may be sized and dimensioned to trap physical debris of less than a predefined dimension while passing at least one of a quantity of a liquid and air. For example, the trap 6133a may be sized and dimensioned to trap ear wax being carried in the discharge.

In some implementations, for example, the traps 6133a, 6133b may be located proximate the proximal end 6105 of the cannula 610. In some implementations, the traps 6133a, 6133b may include, for example, a filter or sieve, such as a mesh filter, woven filter, or non-woven filter, that extends across discharge flow path 6114 and is oriented perpendicular to the direction of flow of the discharge in the discharge flow path 6114. In some implementations, the traps 6133a, 6133b may include a plurality of fingers or projections 6133b that extend radially inward from an inside perimeter 6135 of the discharge collection passage 6114. While a plurality of fingers or projections are illustrated with reference to trap 6133b, the trap 6133b can include any suitable number of fingers or projections, in accordance with embodiments of the present disclosure. For example, the projections may include only a single bar or rod or elongated member that extends completely or partially across the discharge collection passage 6114.

In some implementations, the distal end 6105 of the cannula 610 may include a beveled portion 6115 that overhangs at least a portion of the discharge collection inlet port 6114a. In such implementations, the beveled portion 6115 may position the discharge collection inlet port 6114a such that they are directed at an angle with respect to the central axis 6102, lying in a plane that is neither perpendicular to nor parallel with the central axis 6102. In some implementations, the beveled portion 6115 may be shaped to orient the discharge collection inlet port 6114a at a downward angle with respect to the horizontal axis 344 when a user in an upright position wears the irrigation device 300. Such an orientation may improve the effectiveness and efficiency of the suction introduced at the discharge collection inlet port 6114a to collect the discharge of the irrigation procedure. In some implementations, the beveled portion 6115 may include one or more instances of the irrigation outlet apertures 6112a. For example, one or more irrigation outlet apertures 6112a can be located at a first position along a circumference of the beveled portion 6115 and one or more additional outlet apertures 6112a can be located at a second position along a circumference of the beveled portion 6115.

The proximal end 6103 may include a flanged portion 6123. In some implementations, the flanged portion 6123 may include one or more interfaces to securely engage the cannula 610 to complementary interfaces on a cannula coupler interface (e.g., coupling 105), to thereby secure the cannula 610 to other components of an irrigation device (e.g., a support element 103, e.g., the over-ear earpieces 301, 401, or 501). In some implementations, the flanged portion 6123 may include an interface 6125 formed by an interior wall 6127 that has an exterior diameter 6128, an exterior wall 6129 that has an interior diameter 6130, and an open space 6131 between the exterior diameter 6128 and the interior diameter 6130. In such an implementation, the cannula coupler interface may include a corresponding, complementary interface, such as an annular wall (e.g., the annular wall 4821 depicted with reference to irrigation device 400), that is designed and shaped to fit tightly into the open space 6131 and make contact with the exterior wall 6129 and the interior wall 6127. The cannula coupler interface may securely hold the cannula 610 in place via frictional forces that will oppose movement of the cannula 610, e.g., when the annular wall on the cannula coupler interface is engaged between the interior wall 6127 and the exterior wall 6129. Such frictional forces, though, may not be so great as to prevent a user from removing the cannula 610 from the cannula coupler interface when desired. Accordingly, such an interface 6125 removably, securely engages the cannula 610 with the complementary interface on the cannula coupler interface.

The flanged portion 6123 may include other types of interfaces (e.g., a threaded screw, a bayonet connector (e.g., lugs and complementary recesses) to that enable the cannula 610 to be removably, securely engaged with corresponding structure on a cannula coupler interface. For example, the flanged portion 6123 may include one or more flexible, conformable materials (e.g., rubber O-rings) that provide for a water tight and/or airtight seal between the cannula 610 and the cannula coupler interface.

The interface 6125 may align the irrigation inlet port 6112b located on the proximal end 6103 of the cannula 610 with a port of an inlet path (e.g., the port 4207 depicted with reference to irrigation device 400) located on the cannula coupler interface (e.g., cannula coupler interface 405). The interface 6125 may align the discharge collection outlet port 6114 located on the proximal end 6103 of the cannula 610 with a port of a discharge path (e.g., the vacuum port 4818 depicted with reference to irrigation device 400) located on the cannula coupler interface. In such an implementation, when the cannula 610 is secured to the cannula coupler interface, the interface may provide that the irrigation inlet port 6112b securely mates with and is in fluid communication with the inlet path (e.g., inlet path 116), and that the discharge collection outlet port 6114 securely mates with and is in fluid communication with the discharge path (e.g., discharge path 118). One or more flexible, conformable seals may further be used to provide an air-tight and/or water-tight seal between the irrigation inlet port 6112b and the inlet path, and/or the discharge collection outlet port 6114 and the outlet path.

Figure 15:
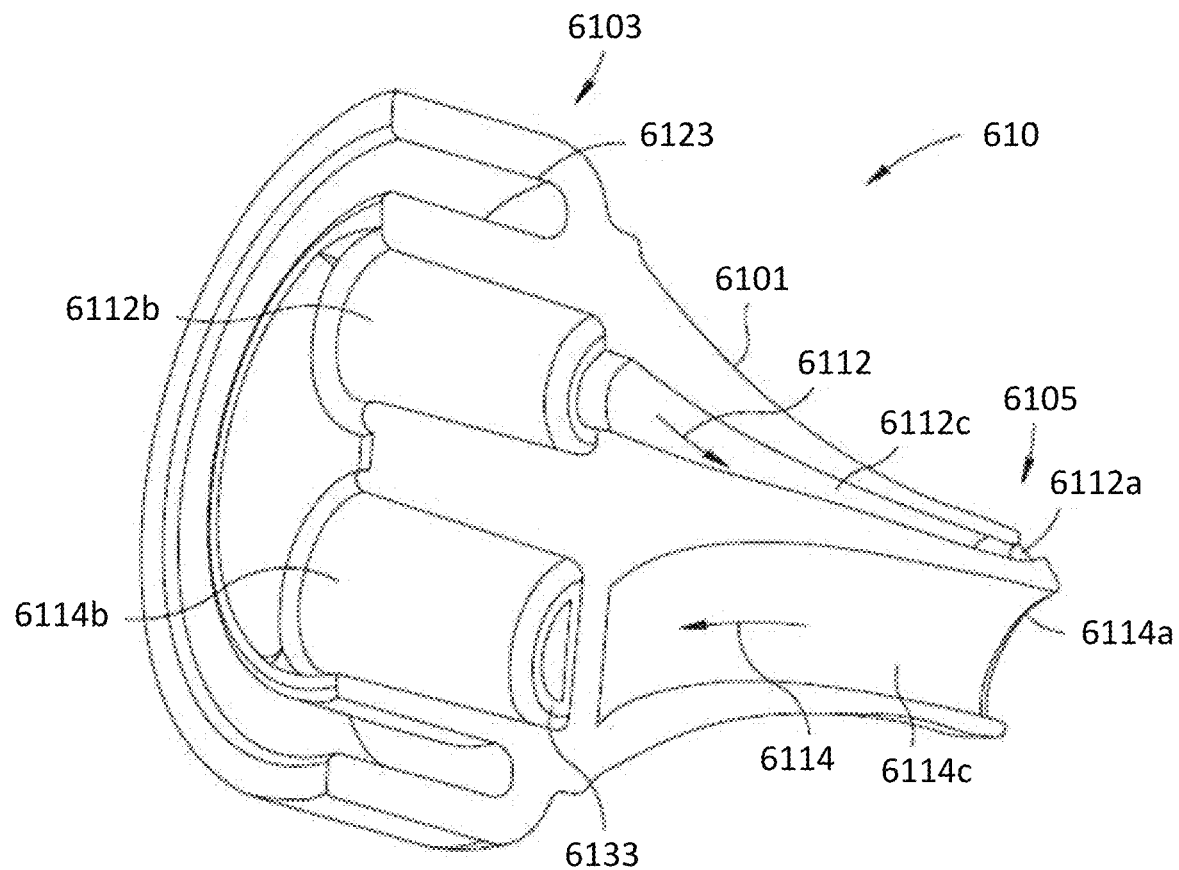
FIG. 15 is a cross-sectional view of the cannula of FIG. 11, which shows the paths of an irrigation passage and a discharge collection passage within the interior of the cannula, according to an embodiment.

FIG. 15 is a cross-sectional view of the cannula 610, which shows the paths of an irrigation passage 6112c of the irrigation flow path 6112 and a discharge collection passage 6114c of the discharge flow path 6114 within the interior of the cannula 610, according to an embodiment.

As shown, the irrigation passage 6112c connects the irrigation inlet port 6112b with one or more irrigation outlet apertures 6112a. The irrigation inlet port 6112b may be substantially cylindrical, and sized and shaped to mate with a corresponding port of an irrigation device that is connected to an inlet path (e.g., inlet path 116). For example, the irrigation inlet port 6112b may be a female connector or fastener, and the corresponding port, e.g., on a coupling (e.g., coupling 105, which with reference to irrigation device 400, can be implemented as a cannula coupler interface 405) may be a complementary male connector or fastener. The irrigation passage 6112c may flatten as it progresses past the flanged portion 6123, towards the distal end 6105. Such flattening may cause the irrigation passage 6112c to form an arc shape that runs proximate the distal end 6105 and extends between the various irrigation outlet apertures 6112a.

The discharge collection passage 6114c provides a discharge flow path 6114 between the discharge collection inlet port 6114a and the discharge collection outlet port 6114b, and may be sized and shaped to mate with a corresponding port of an irrigation device that is connected to a discharge path (e.g., discharge path 118) when the cannula 610 is physically coupled with other components of the irrigation device. For example, the discharge collection outlet port 6114b may be a female connector or fastener, and the corresponding port, e.g., on a coupling (e.g., coupling 105, which with reference to irrigation device 400, can be implemented as a cannula coupler interface 405) may be a complementary male connector or fastener. The discharge collection passage 6114c may have a smaller diameter at the distal end 6105 compared to that at the proximal end 6103. Such narrowing may be gradual, such that the discharge collection passage 6114c gradually tapers along the length of the cannula 610. Alternatively, such narrowing may be abrupt and occur, for example, at a point where the discharge collection passage 6114c moves out of the flanged portion 6123. The trap 6133a may be located within the discharge collection passage 6114c, and sized, shaped, and oriented to capture particles greater than a specified size being carried within the discharge.

Figure 16:
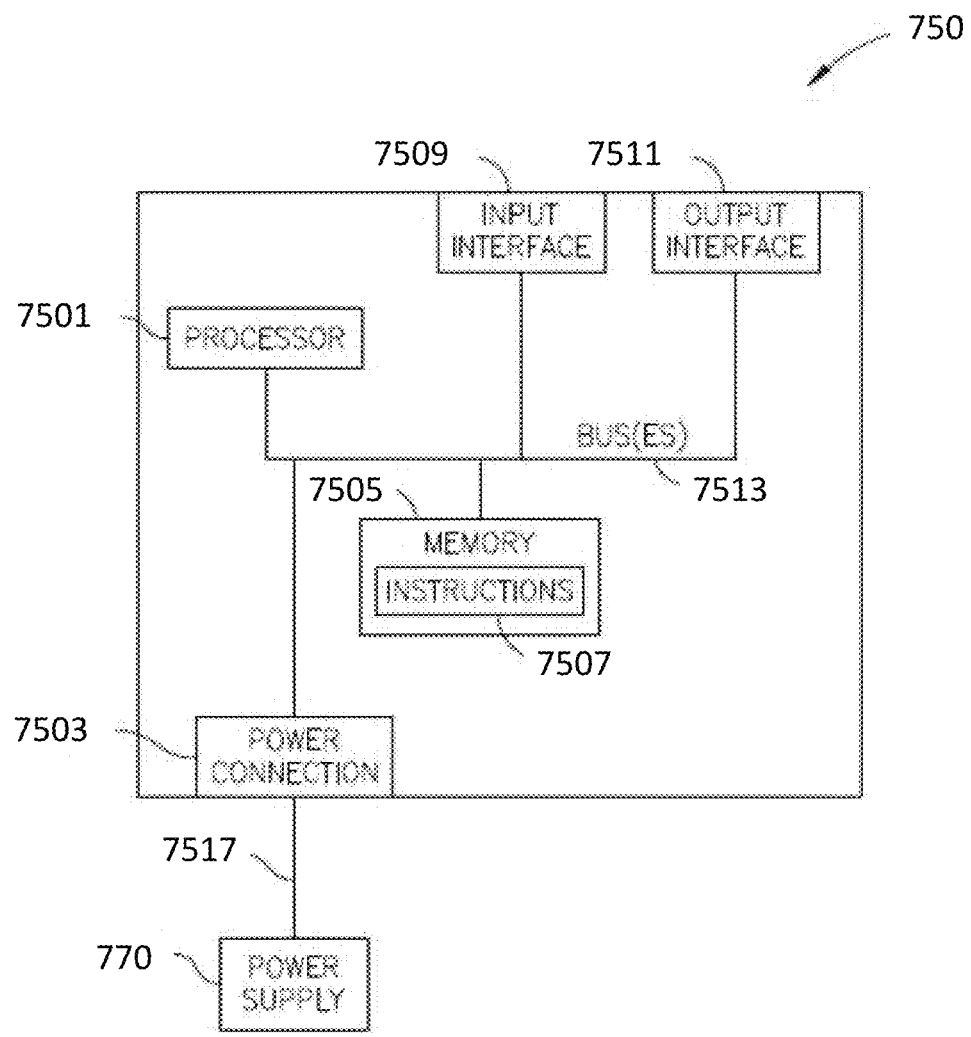
FIG. 16 is a block diagram depicting a controller and a power supply, which may be used with or as part of an irrigation device, according to an embodiment.

FIG. 16 is a block diagram of a controller 750 and a power supply 770, which may be used with or as part of an irrigation device, according to an embodiment. As shown, the controller 750 includes at least one processor 7501, a connection 7503 to the power supply 770 (e.g., a battery), one or more memories 7505 that store one or more sets of processor-executable instructions 7507, an input interface 7509, and an output interface 7511. Each of these components may be communicatively connected by bus(es) 7513, which can provide bidirectional communication between the various components of the controller 750. Bus(es) 7513 may take, for example, the form of a plurality of buses (e.g., data buses, instruction buses, power buses) included in at least one body.

The input interface 7509 may be electrically and communicatively coupled to the user interface 460 and be used to receive user inputs in the form of electrical signals. Such user inputs may include, for example, selecting between a plurality of irrigation programs stored as sets of processor-executable instructions 7507 by the one or more memories 7505. The output interface 7511 may be electrically and communicatively coupled to one or both of a pump assembly (e.g., pump assembly 124, 424, etc.) and the vacuum assembly (e.g., vacuum assembly 126, 426, etc.). The output interface 7511 may be used to transmit electrical signals generated by the processor 7501 and that result in activating or deactivating the pump assembly and/or the vacuum assembly.

The processor 7501 may be any logic processing unit, such as one or more central processing units (CPUs), digital signal processors (DSPs), application-specific integrated circuits (ASICs), field programmable gate arrays (FPGAs), etc. The power supply 770 may include one or more power supplies 770 to provide electrical power to the various components of the irrigation device 100 via power connections 7517. The power supplies 770 may be an internal power supply, such as a battery, energy source, fuel cell, or the like. In some embodiment, the power supply can be charged and/or recharged using an external power source. In some embodiments, the power supply 770 can be used with an external power supply to power the irrigation device (e.g., irrigation device 100, 200, 300, 400, etc.).

The one or more memories 7505 may include read-only memory ("ROM") and random access memory ("RAM"). The one or more memories 7505 may comprise a flash drive to store data and/or processor-executable instructions. In some implementations, the one or more memories 7505 may include a hard disk drive for reading from and writing to a hard disk, an optical disk drive for reading from and writing to removable optical disks, and/or a magnetic disk drive for reading from and writing to magnetic disks. The one or more memories 7505 may communicate with the processor 7501 via the system bus 7513. Those skilled in the relevant art will appreciate that other types of computer-readable media that can store data accessible by a computer may be employed, such as WORM drives, RAID drives, magnetic cassettes, flash memory cards, digital video disks ("DVD"), Bernoulli cartridges, RAMs, ROMs, smart cards, etc.

The one or more sets of processor-executable instructions 7507, when executed, cause the irrigation device 100 to perform one or more irrigation routines. As an example, such irrigation routines, when executed, may cause the processor 7501 to transmit a first signal to the vacuum assembly (e.g. vacuum assembly 126, 426, etc.) via the output interface 7511 at a specified time that results in the vacuum assembly being turned on, thereby creating a vacuum force to cause discharge to move into the delivery element (e.g., discharge port 114 of delivery element 100, discharge collection inlet port 6114a of the cannula 610, etc.) through a discharge fluidly communicative path (e.g., discharge path 118, discharge fluidly communicative path 418, etc.) and into a discharge reservoir (e.g., discharge reservoir 130, 430, etc.). Such irrigation routines, when executed, may cause the processor 7501 to transmit a second signal to the pump assembly (e.g., pump assembly 124, 424, etc.) via the output interface 7511 at a specified time that results in the pump assembly being turned on, thereby forcing cleaning agent to move from or exit the cleaning agent reservoir (e.g., fluid reservoir 120, 420, etc.) through the cleaning fluid fluidly communicative path (e.g., inlet path 116, 416, etc.) to the cannula (e.g., delivery element 110, cannula 610, etc.), where it exits through the irrigation outlet apertures (e.g., inlet port 112, irrigation outlet apertures 6112a, etc.) at pressure. The processor 7501 may activate the pump assembly using a plurality of pulses in which the pump assembly is activated and de-activated for short time durations (e.g., about two seconds) during the irrigation routine before the pump assembly is turned off. The set of processor-executable instructions 7507 may provide for irrigation procedures of different time periods (e.g., up to 30 seconds, 30 seconds, one minute, or more than one minute).

Figure 17:
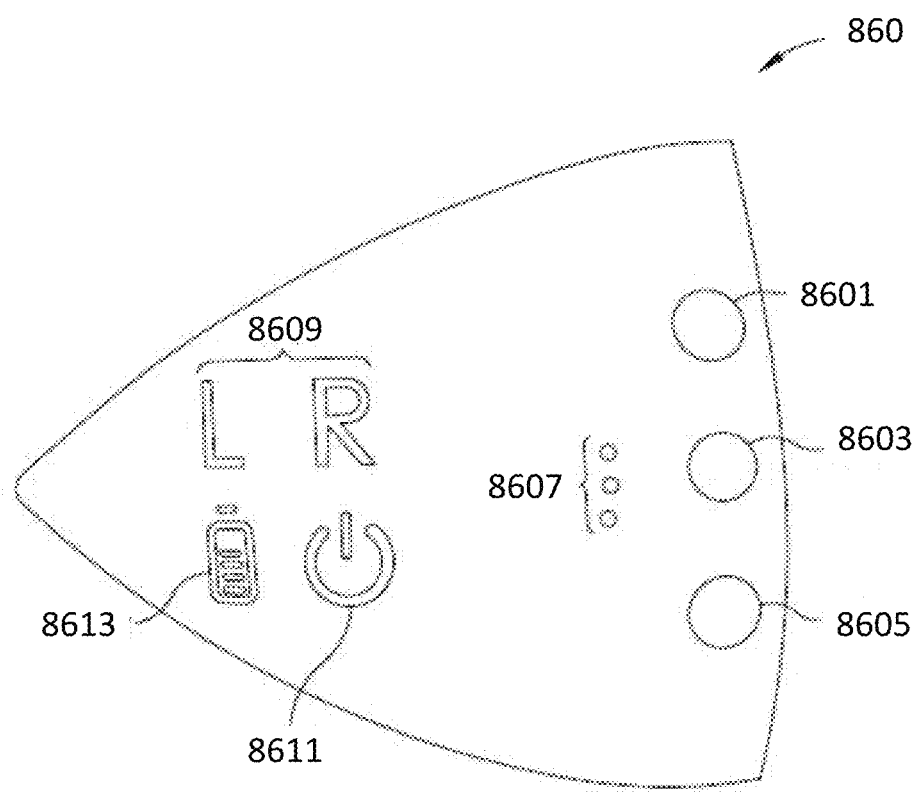
FIG. 17 is a schematic diagram depicting a user interface or user-actable selectable controls of an irrigation device, according to an embodiment.

FIG. 17 shows an example of a user interface or user-actable selectable controls 860 ("user interface 860" or "user-actable selectable controls 860") of an irrigation device, such as of any of the irrigation devices described herein, according to an embodiment. As shown, the user interface 860 may include one or more input elements (e.g., an ear selection button 8601, a program selection button 8603, a start button 8605) and one or more indicators or feedback elements (e.g., a set of LEDs 8607, an ear activation indicator 8609, a power indicator 8611, a charging indicator 8613).

The ear selection button 8601 may be used to turn on the irrigation device (e.g., irrigation device 100) and select the ear to be cleaned. In some implementations, the ear selection may be performed by touching a touch-sensitive or touch-responsive (e.g., resistance, inductive or capacitance touch sensors) area (not depicted) of the irrigation device 100, e.g., located on the user interface 860 or proximate to or at the earset of a respective ear. The program selection button 8603 may be used to select between a plurality of irrigation routines that may correspond to a plurality of sets of processor-executable instructions (e.g., processor-executable instructions 7507) stored within the one or more memories (e.g., a memory 7505). For example, the program selection button 8603 may be used to toggle or cycle through the plurality of irrigation routines. The set of LEDs 8607 may be used to show which routine is currently selected by the user. Thus, in some implementations, each LED may correspond to a location within the memory that stores instructions for a specific irrigation routine. The LED corresponding to the currently selected irrigation routine may be lit up. The start button 8605 may be used to start the currently selected irrigation routine. While specific implementations of input and feedback elements are described with reference to user interface 860, other implementations of such elements, e.g., visual, auditory, haptic, etc., can be used.

In some implementations, the ear activation indicator 8609 may indicate, for example, which earpiece is currently in operation, with the "R" corresponding to an earpiece designed to fit over the user's right ear (e.g., earpiece 301a, 401a) and the "L" corresponding to the earpiece designed to fit over the user's left ear (e.g., earpiece 301b, 401b). The power indicator 8611 indicates, for example, whether the irrigation device is currently powered on and running a cleaning cycle. The charging indicator 8613 indicates, for example, whether the irrigation device is currently electrically coupled to a power source such that the onboard power supply (e.g., power supply 170, battery 770) is being charged. The amount of charge that the power supply currently holds may be directly related to the amount of the charging indicator 8613 that is lit up. In addition or alternatively, a fully charged power supply may cause the charging indicator 8613 to switch from one color (e.g., red) that corresponds to the power source charging to a second color (e.g., green) that indicates that the power source is fully charged. Some implementations may include other signal and indicators. For example, one or more indicators may be used to signify that the pump assembly is providing cleaning agent at too high of a pressure, that the vacuum assembly is providing too strong of a vacuum, that the discharge passage (e.g., discharge path 117) is blocked, etc. In some instances, the irrigation device may automatically shutdown to prevent injury to the user or damage to the irrigation device (e.g., in cases of detected abnormal activity, e.g., electrical malfunction). In some implementations, at least one of the user interface 860 elements may be used as a "kill" switch or emergency shut-off switch to automatically shut down the irrigation device, e.g., in response to user input.

The user interface 860 may be configured to receive user inputs and commands from a user, such as of the irrigation device. In some implementations, the user interface 860 may include, for example, a button, switch, touch screen, and/or any other suitable actuation mechanism to receive the user inputs and commands. The user interface 860 may additionally or alternatively include, for example, a display (not depicted) for displaying feedback such as device or operational status to the user, such as with respect to irrigation operation to be performed, and the like. For example, the user interface 860 may be electrically and communicatively coupled to a controller (e.g., controller 150) for data communications. The data communications may be configured to enable the controller to receive user input from the user interface 860 for execution in performing an ear cleaning operation. The user input may include, for example, a selection of one or more of a plurality of irrigation programs, which may be respectively stored as sets of processor-executable instructions on one or more memories of the irrigation device.

In some implementations, the user interface 860 may include a touchscreen device. The touchscreen device may be configured to, for example, receive user inputs from and provide feedback to the user such as by way of an electronic visual display or screen to facilitate user selection, adjustment, and configuration of irrigation operations to be performed, for example, by the ear cleaning device. In some implementations, the touchscreen device may be configured to render and display a graphical user interface symbol or element, such as one resembling a button, scale, bar, panel, switch, or any other user interface element corresponding to a user-selectable input, command, or control element (e.g., the ear selection button 8601, the program selection button 8603, the start button 8605, the set of LEDs 8607, the ear activation indicator 8609, the power indicator 8611, the charging indicator 8613, etc.). In some implementations, for example, the irrigation device may be configured to implement wireless communications such as Bluetooth®, WiFi®, near field communications, and the like, such that touch screen controls may be displayed via a wireless device such as the user's smartphone/tablet or any other suitable device. In such implementations, the user interface 860 may be configured to receive input from the user by way of single- or multitouch gestures, and the like.

Figure 18:
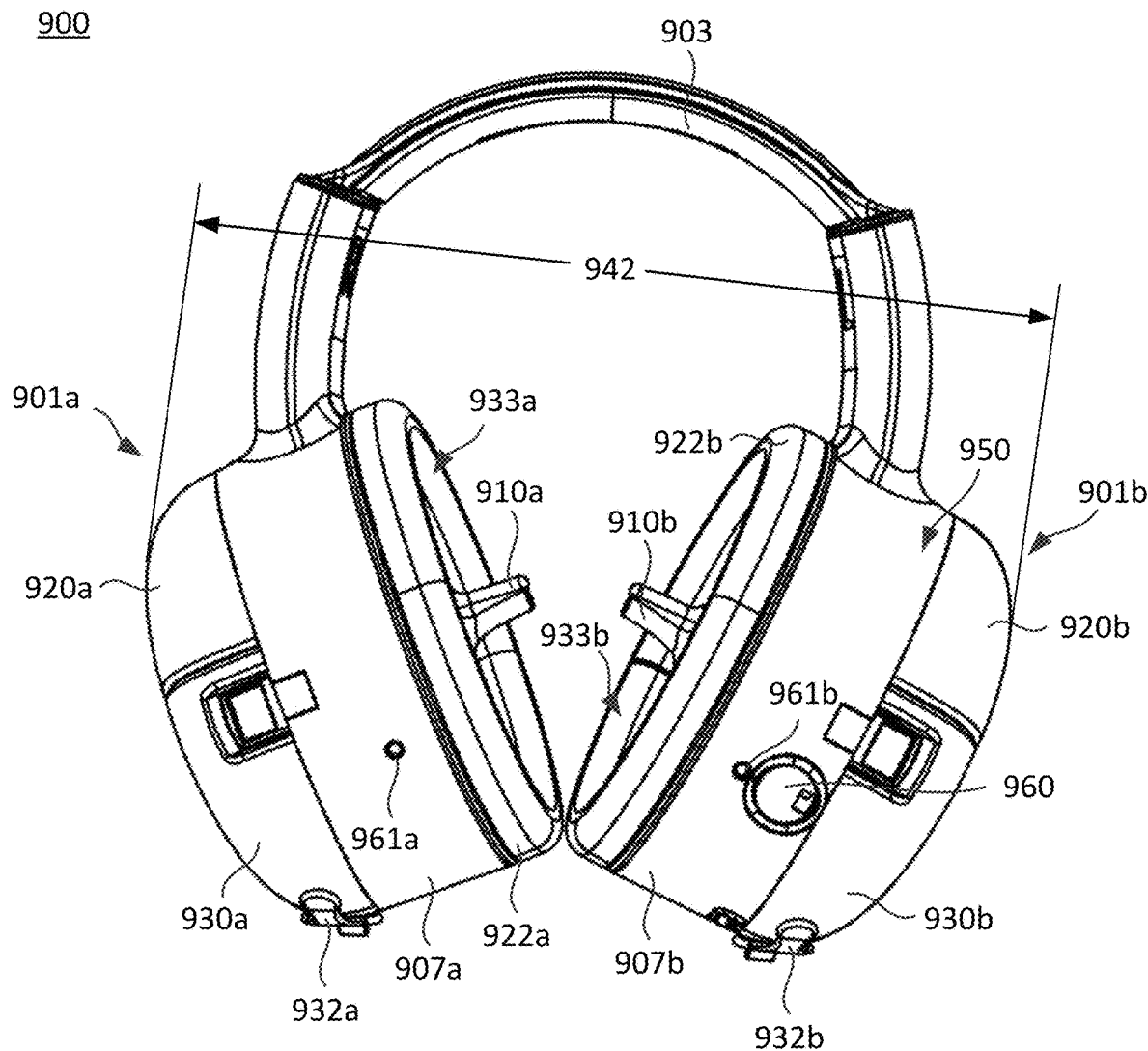
FIG. 18 is a perspective view of an ear cleaning or irrigation device, according to an embodiment.
Figure 19B:
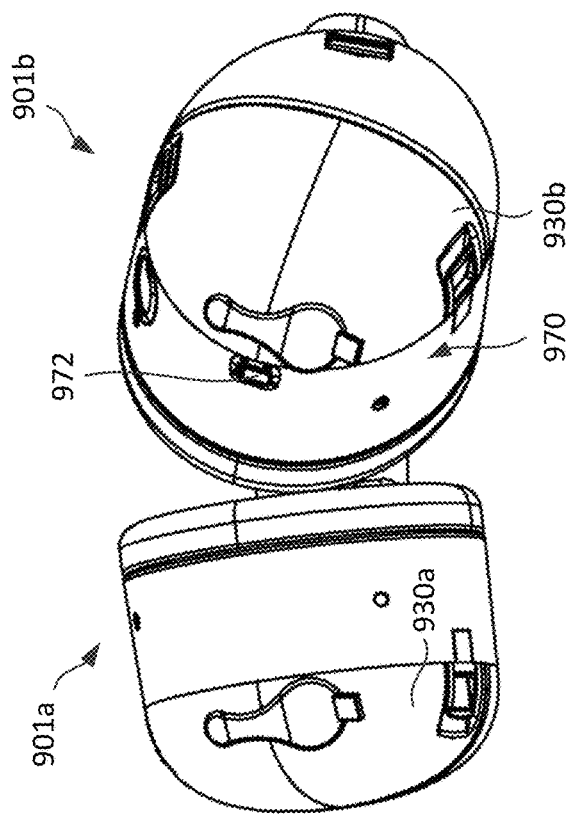
FIGS. 19A-19B are various views of a first configuration of the ear cleaning or irrigation device depicted in FIG. 18, according to an embodiment.
Figure 19A:
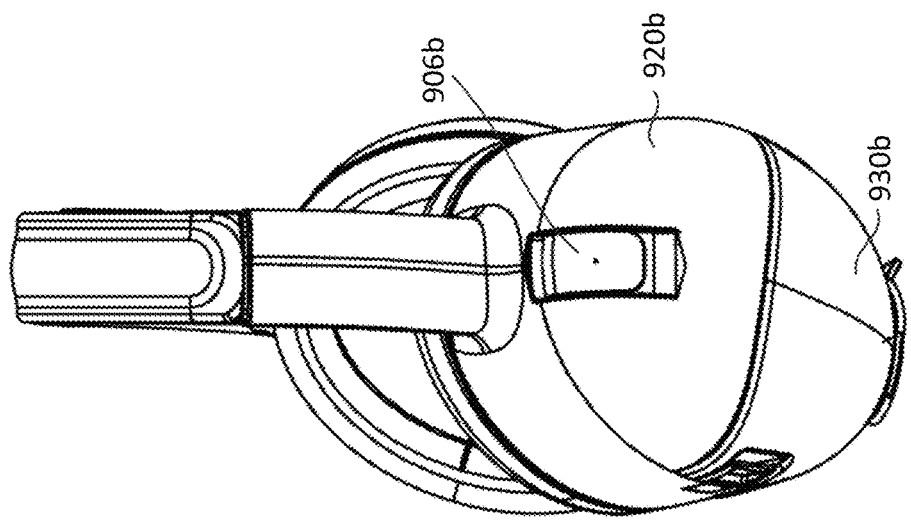
Figure 20B:
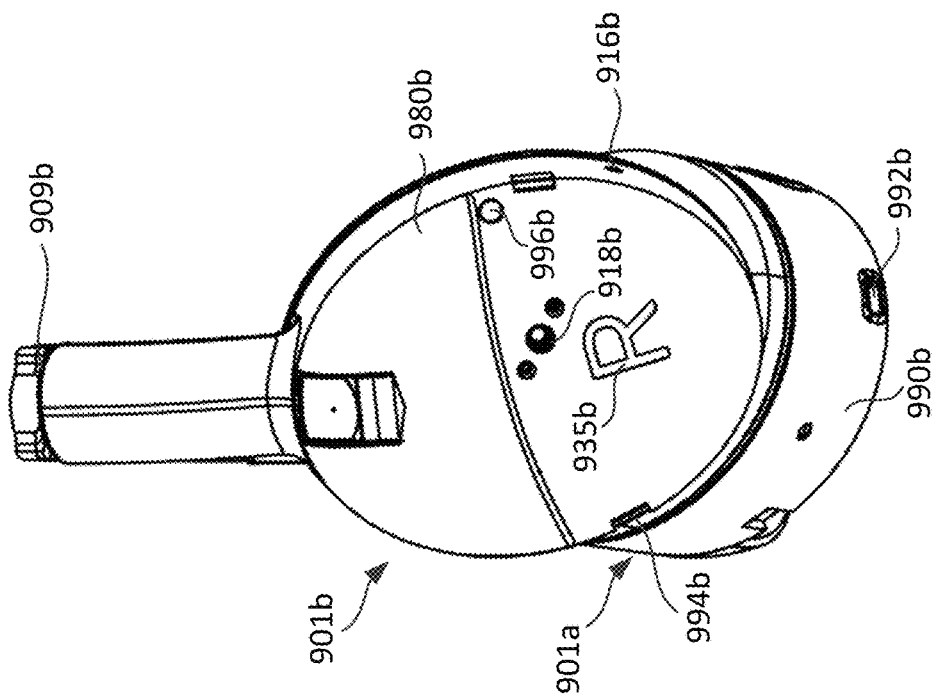
FIGS. 20A-20B are various views of a second configuration of the ear cleaning or irrigation device depicted in FIG. 18, according to an embodiment.
Figure 20A:
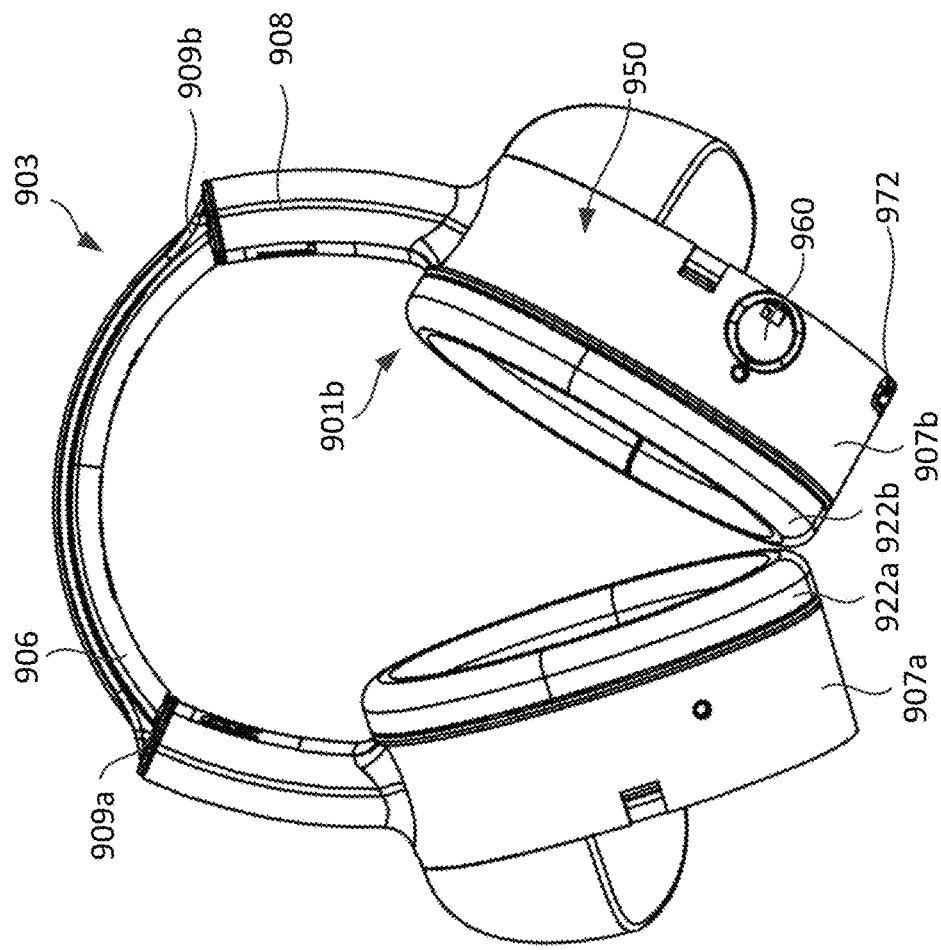

FIG. 18 is a perspective view of an ear cleaning or irrigation device 900, according to an embodiment. FIGS. 19A-19B are various views of the ear cleaning or irrigation device 900 in a first configuration, according to an embodiment. FIGS. 20A-20B are various views of the ear cleaning or irrigation device 900 in a second configuration, e.g., with one or more disposable components removed, according to an embodiment. The irrigation device 900 can include components that are functionally and/or structurally similar to other irrigation devices described herein (e.g., irrigation device 100, 200, 300, 400, etc.). As shown, the irrigation device 900 may include a support element implemented as first and second earpieces or earsets 901a and 901b (collectively, "earpiece(s) 901" or "earset(s) 901") connected via a head strap 903, first and second delivery elements implemented as cannulas 910a and 910b (collectively, "delivery element(s) 910" or "cannula(s) 910") connected to respective cannula coupler interfaces or couplings (not depicted), first and second fluid reservoirs 920a and 920b (collectively, "fluid reservoir(s) 920" or "cleaning agent reservoir(s) 920"), and first and second discharge reservoirs 930a and 930b (collectively, "discharge reservoir(s) 930").

In some implementations, the earpieces 901 may be sized and shaped for interchangeable fit over a user's right or left ears, such that the first earpiece 901a fits over one of the user's right or left ears, and the second over-ear earpiece 901b fits over the other of the user's right or left ears.

In some implementations, each earpiece 901 may include an interior side and an opposing exterior side, similar to those described with reference to FIG. 3B. For example, the interior side of each earpiece 901 may be configured to be positioned adjacent to and directed towards a region about an ear of a user's head when the user wears the irrigation device 900. Each earpiece 901 may include a perimeter, extending between its interior and exterior sides, and arranged, sized, and shaped to enable the earpieces 901 to enclose a wide range of various ear shapes and the associated regions thereabouts. For example, in some implementations, the perimeter may be substantially circular, oval, or elliptical in shape, and may define an area sufficient to encompass the various ear shapes and the associated regions thereabouts.

In some implementations, the earpieces 901 may respectively include annular membranes 922a and 922b (collectively, "annular membrane(s) 922"). In some embodiments, annular members 922a, 922b can function as sealing elements configured to seal fluid discharge or any other substances that may exit or leak from around a user's ear during an irrigation procedure. In some implementations, the annular membranes 922a and 922b may be positioned on the interior sides of respective earpieces 901a and 901b, and arranged around delivery elements 910a and 910b, respectively such as shown in FIG. 18. In some implementations, the annular membranes 922a and 922b may include respective interior and exterior walls (e.g., similar to the interior and exterior walls 335a and 337a, as described with reference to FIGS. 3A-3B). In some implementations, the interior walls of each annular membrane 922a, 922b may be arranged about a respective one of the delivery elements 910a and 910b. In such implementations, the exterior walls may be arranged concentrically about the interior walls to entirely or otherwise encompass the interior walls. In some implementations, commonly-facing surfaces of each of the interior and exterior walls of each annular membrane 922 may be connected by a rim configured to span or traverse a distance between the commonly-facing surfaces. In such implementations, the rim may include outwardly-curving facets or surfaces, collectively arranged to curve in an outward direction, away from each respective delivery element 910. In such implementations, the annular membrane 922 may be sized and shaped to resemble a portion of a blunt, solid torus (e.g., the top half of a doughnut), such as depicted in FIG. 18.

In some implementations, each annular membrane 922 may be made of a cushioning, compressible, or otherwise deformable material. In some implementations, each annular membrane 922 may additionally be partially comprised of a resilient material, such as to increase durability, and the like. For example, the cushioning material may include an elastomeric or elastomer-based core material, such as a closed-cell foam (e.g., polyurethane), open cell foam, gel in a pouch, silicone, and/or rubber material, enclosed by an outer cover material, such as plastic, leather, leatherette, fabric, polymer, or the like. Together or otherwise, the cushioned and resilient materials of each annular membrane 922 may be configured to provide a comfortable fit for a user when wearing the irrigation device 900. Further, the cushioned and resilient materials may be configured to enable the annular membrane 922 to conform to the shape of the user's head (or other surface upon which it rests) when using the irrigation device 900, e.g., when the irrigation device 900 is positioned on a user. Accordingly, each annular membrane 922 may be configured to form a seal against the user's head to thereby trap cleaning agent that would otherwise escape, for example, from either of the cannulas 910 and/or the user's auditory canals (e.g., ear canal EC) during an irrigation procedure. In some implementations, each sealing element 922 may be formed of an inner core, composed at least in part of elastomer-based materials, and an outer protective cover encompassing the inner core, composed of resistant material such as a water-resistant plastic, polymer, fabric, or some other material that does not wear or degrade when wet. Accordingly, the outer protective cover may be configured to protect the inner core from various elements in the environment. In some implementations, the annular membranes 922 may be individually detachably removable from each respective earpiece 901 to thereby enable periodic replacement, such as after each use of the irrigation device 900, and/or enable cleaning, disinfecting, etc. between uses.

The interior walls of the annular membranes 922a and 922b may respectively form cavities 933a and 933b (collectively, "cavities 933"), each sized and shaped to receive and enclose individual, variously sized and shaped ears of users. The size and shape of the annular membranes 922 and the cavities 933 may further be configured to position the cannulas 910 within a user's auditory canal when the user is wearing the irrigation device 900. In some implementations, each cavity 933 may be cylindrical in shape to thereby create a cylindrical space in which the cannulas 910 may be individually and respectively disposed and oriented, such as along respective central axes of each cavity 933. In some implementations, the cavities 933 may be elongated such that the perimeter of the interior walls of the annular membranes 922a and 922b form a substantially elliptical or oval shape. In such implementations, the cavities 933 may be relatively longer along the vertical axes of each earpiece 901, and relatively shorter along the horizontal axes of each earpiece 901. Elongating the cavities 933 as such may improve or provide for a better, more comfortable fit for the user.

Each cavity 933 may include a depth formed by a height of the interior walls of the annular membranes 922a and 922b. In some implementations, the depth of the cavities 933a and 933b may be less than a height of the cannulas 910a and 910b, respectively, enabling the cannulas 910a and 910b to extend past the rims of the annular membranes 922a and 922b of each respective earpiece 901 to thereby enter the user's auditory canal when a user wears the irrigation device 900. In some implementations, as further described below, each cannula 910 may be tapered such that tips of each cannula 910 gradually narrow towards a base of each cannula 910, respectively, to assist in insertion and positioning of the tips of the cannulas 910 into the user's auditory canal. The tapering of each cannula 910 can be configured such that a portion of each cannula 910 between the tip and the base makes contact with the outside opening of the user's auditory canal, so as to prevent each tip of each cannula 910 from making contact with and potentially injuring the ear drums of the user.

In some embodiments, portions of the irrigation device 900 (e.g., headsets 901a, 901b, annular membranes 922a, 922b, etc.) can be made of a transparent material to enable visualization of an area surrounding a user's ear, e.g., to facilitate placement of the delivery elements 910a, 910b into the ear. In some embodiments, a visualization device or sensor (e.g., camera, light sensor, electric sensor) can be place on an inner surface of each earset 910a, 910b to provide feedback to a user when positioning the irrigation device 900 on a user's head, e.g., to confirm placement of the delivery elements 910a, 910b in the user's ear canal.

In some implementations, such as shown in FIG. 18, the irrigation device 900 may include an adjustable head strap 903, configured to adjustably connect the first earpiece 901a and the second earpiece 901b in spaced apart spatial relation and position across a lateral span 942 of the irrigation device 900. The adjustable head strap 903 may be sized and shaped to fit over a user's head to thereby position the first earpiece 901a over the user's first ear, and the second earpiece 901b over the user's second ear. For example, in some implementations, the adjustable head strap 903 may be configured to be flexible such that the first earpiece 901a and the second earpiece 901b can be individually moved or flexed laterally, such as to adjust a length of the lateral span 942 of the irrigation device 900.

In some embodiments, the earpieces 901a and 901b may include respective vertical adjustors (not depicted). Each vertical adjustor may be configured to couple to one of the earpieces 901 to thereby enable each respectively coupled earpiece 901 to independently or otherwise move or rotate about a vertical axis of each earpiece 901, with respect to and along the adjustable head strap 903, when a user is wearing the irrigation device 900. Accordingly, the vertical adjustors may be implemented in adjusting a fit of the irrigation device 900, such as to accommodate different user head sizes and/or shapes with respect to the various circumferential distances between different users' ears (e.g., from one ear of a user, over the top of the user's head, and to the other ear of the user).

In some implementations, the adjustable head strap 903 may include, for example, pivot couplers (not depicted) configured to connect to a respective one of the earpieces 901a and 901b, to thereby enable respective rotational and pivotal motion of the earpieces 901. Accordingly, the pivot couplers may be implemented in conjunction with the earpieces 901 to enable the irrigation device 900 to more comfortably fit on a user's head with respect to the contours of the user's head when the user dons the irrigation device 900.

The earpieces 901a and 901b can include respective housings 907a and 907b that can serve as support structures for one or more other components of the irrigation device 900. For example, housings 907a, 907b can include structures for mounting one or more of head strap 903, cannulas 910a and 910b, first and second fluid reservoirs 920a and 920b, and first and second discharge reservoirs 930a and 930b. At least one of the housings 907a, 907b can also support and/or house one or more of a controller 950, an I/O interface 960, a power support, a pump assembly, a vacuum assembly, etc.

In some implementations, each fluid reservoir 920 may be configured to contain a fluid, e.g., including a cleaning agent (e.g. a supply of a fluid cleaning agent) for irrigation and cleaning of a user's ear (e.g., auricle AR and/or ear canal EC). In some implementations, the fluid may include, for example, saline, hydrogen peroxide, water, an anti-bacterial agent, an antibiotic agent, and the like. Similar to that described with reference to any of the irrigation devices herein, each fluid reservoir 920 may connect to an inlet path by way of a first fluid coupling (not depicted), which may in turn may connect to one or more inlet ports of a delivery element 910a, 910b by way of a second fluid coupling (not depicted) to establish fluid communication therebetween. In some implementations, the inlet path may include a manifold such that the fluid can be directed into one or more inlet ports and therefore exit the delivery elements 910a, 910b from multiple openings. Each fluid reservoir 920 may be or include, for example, a reservoir, container, or the like. In some implementations, the fluid reservoirs 920 may be disposable and/or recyclable. For example, in some implementations, the fluid reservoirs 920 may be partially or completely made of disposable and/or recyclable materials, such as a plastic, paper, metal, or other materials described herein.

In some implementations, the irrigation device 900 may include a heating element that is configured to heat a contained supply of fluid cleaning agent to, for example, a preset temperature, e.g., within a range having limits or bounds above, below, or substantially equal to body temperature (e.g., of a user), to support a comfort level of the user during use of the irrigation device 900. The heating element can be, for example, disposed within the fluid reservoir 920 and/or along the inlet path. In some implementations, the heating element can be, for example, a heater or resistive element configured to heat and maintain the contained supply of fluid to and at a predefined (e.g., user-selected) temperature. In some implementations, one or both of the fluid reservoirs 920 may be insulated. In some implementations, the irrigation device may include a temperature sensor such as a thermometer for measuring the temperature of the contained supply of fluid. The temperature sensor can be disposed, for example, within the fluid reservoir 920 and/or along the inlet path. In some implementations, the fluid reservoirs 920 may be pre-filled (e.g., come pre-packaged with a supply of a fluid cleaning agent). In other implementations, a user or someone (e.g., a physician or other medical practitioner) administering the fluid cleaning agent can prepare and/or fill the fluid reservoirs 920 with a supply of fluid cleaning agent by way of one or more inflow ports, as described with reference to FIGS. 19A-19B.

In some implementations, each fluid reservoir 920 may be configured for fluid communication with a respective cannula 910 by way of a cannula coupler interface (not depicted), e.g., similar to the coupling 105 described with reference to FIG. 1. Moreover, respective fluid communication paths, e.g., similar to the inlet path 116 or cleaning fluid fluidly communicative path 416, may be configured to connect each fluid reservoir 920 to its respective cannula 910 so as to establish and enable fluid communication therebetween. For example, when an irrigation procedure begins, fluid such as a fluid cleaning agent contained in one or both of the fluid reservoirs 920 may be communicated to the cannulas 910 for discharge and delivery to an ear canal EC of a user through a nozzle outlet of the cannulas 910, as further described in reference to FIGS. 22A-22G. In some embodiments, a single fluid reservoir 920 (e.g., either fluid reservoir 920a or 920b) can be configured to supply fluid to both delivery elements 910a, 910b, e.g., via a fluid path through head strap 903 or another fluid path (not depicted). The single fluid reservoir 920 can be mounted on one of the earsets (e.g., earset 901a, 901b) or separately from both earsets (e.g., at a point along head strap 903), and separate fluid paths can couple the fluid reservoir 920 to each of the delivery elements 910a, 910b. Such embodiments can reduce components that may need to be cleaned and/or disinfected between uses by a physician or other administrating user, e.g., by having one fluid reservoir 920 that requires cleaning and/or disinfecting. The single fluid reservoir 920 can be configured to hold sufficient liquid and/or cleaning agent for supplying fluid to clean two ears.

One or more pump assemblies (e.g., similar to pump assemblies 124 or 424) may be coupled to the fluid reservoirs 920 to move the cleaning agent contained in one or both of the fluid reservoirs 920 through and along respective fluid communication paths by applied pressure. The pressure may be applied, for example, to the volumes of the fluid reservoirs 920 in which the cleaning agents are contained. In some implementations, for example, the one or more pump assemblies may include a pump configured to draw cleaning agent from one or both of the fluid reservoirs 920 at a preset pressure and/or flow rate. In some implementations, the upper limit or bound of the pressure applied by the one or more pump assemblies may be less than about 100 kPa (approximately 0.986 atmospheres).

With reference to FIGS. 20A-20B, in some implementations, one or both of the earpieces 901 may include an electrical port or interface 972 ("electrical port 972"). The electrical port 972 may include, for example, any suitable type of electrical port, interface, connector, socket, or receptacle, configured to enable the irrigation device 900 to receive power and/or communications from an external source. For example, the electrical port 972 may include a universal serial bus (USB) connector configured to electrically couple to an external power supply (e.g., such as the power supply 170) or power source (e.g., for charging an internal power supply and/or supplying power directly to the irrigation device 900). For example, a power supply disposed within the irrigation device 900 (e.g., disposed within housing 907b) may be powered or charged by connection of the electrical port 972 to an external power source. In some implementations, the electrical port 972 may additionally or alternatively include, for example, an inductive, wireless, or cordless coupling or charging interface for charging the internal battery by way of electromagnetic induction. In some implementations, the irrigation device 900 may include only one such electrical port 972, such as shown in FIG. 20A. In such implementations, the over-ear earpieces 901a, 901b may be electrically coupled to one another by connection to an electrical circuit to which the port 972 may also be connected, where the electrical circuit may be routed, e.g., through the adjustable head strap 903.

With reference to FIG. 20B, in some implementations, each earpiece 901a, 901b may include respective indicia 935a, 935b, configured to indicate to a user which ear that earpiece 901a, 901b is configured to be used with and/or which removable components (e.g., delivery elements 910a, 910b and/or discharge reservoirs 930a, 930b) should be attached to that earpiece 901a, 901. For example, as shown in FIG. 20B, the indicia 935b of the earpiece 901b may be configured to indicate to a user that the earpiece 901b is configured to interface with the discharge reservoir 930b.

Generally, the indicia 935 of each earpiece 901 may include any indicia or markings suitable to enable or facilitate user-friendly confirmation of correct installation of components of the irrigation device 900 by visual, haptic, and/or other perception of the indicia by a user, in accordance with the present disclosure.

Figure 21A:
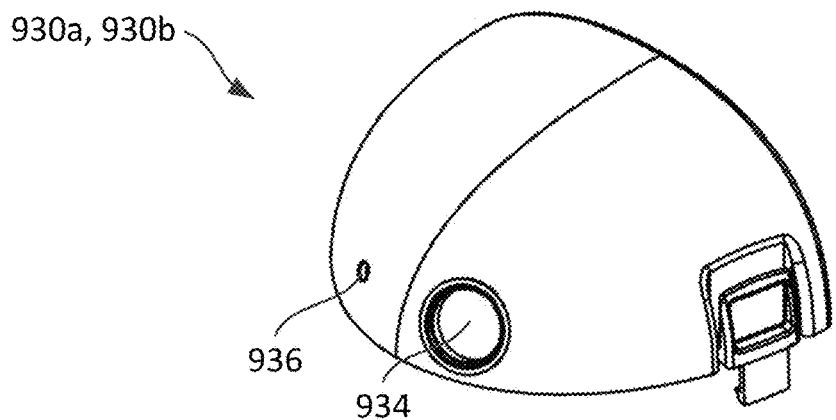
FIGS. 21A-21C are various views of discharge reservoirs of the ear cleaning or irrigation device depicted in FIG. 18, according to an embodiment.
Figure 21B:
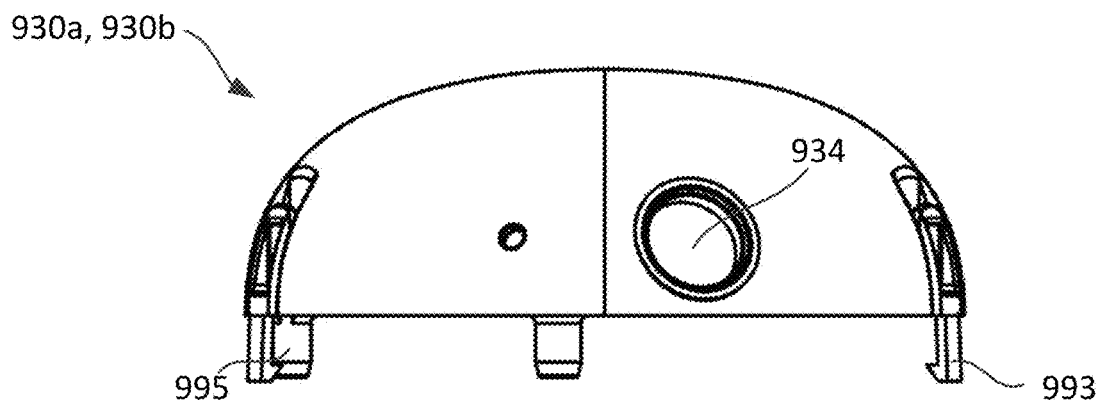
Figure 21C:
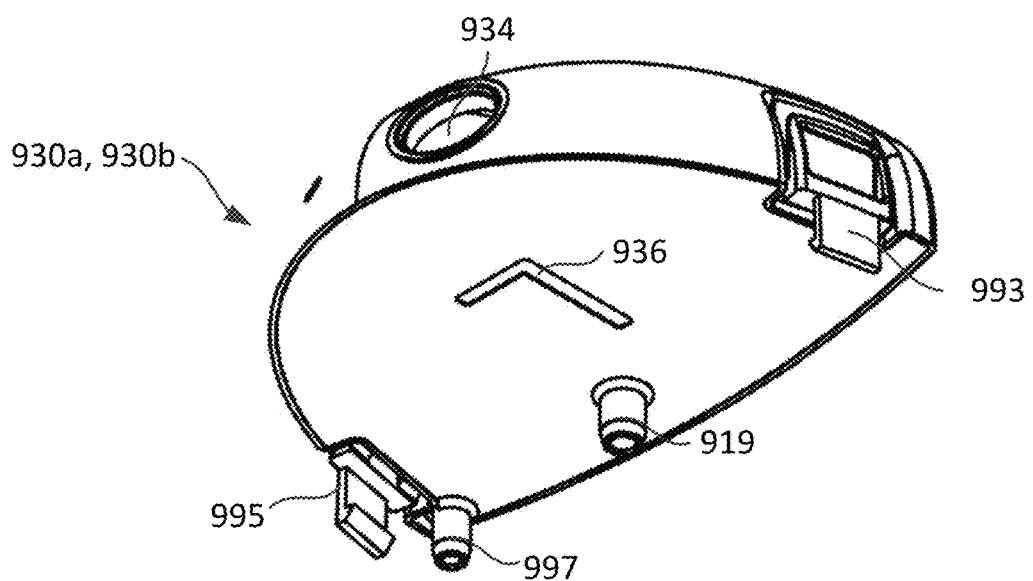

FIGS. 21A-21C are various views of the first and second discharge reservoirs 930a and 930b of the ear cleaning or irrigation device 900, according to an embodiment. As shown, the discharge reservoirs 930 may each include, for example, a discharge release port 934, first and second coupling elements implemented as release tabs 993, 995, a discharge inlet port 919, a pressure relief port 997, and earpiece correspondence indicia 935.

In some implementations, each discharge reservoir 930a, 930b may be configured to receive and contain fluid or cleaning agent, such as the applied fluid or cleaning agent from an irrigation and cleaning operation applied to the user's ear (e.g., auricle AR and/or ear canal EC) by the irrigation device 900 in use. Each discharge reservoir 930a, 930b may include, for example, a container, reservoir, holding tank, or the like, for receiving, such as by way of the discharge inlet port 919, fluid and/or any substances entrained in the fluid for containment from one or both of the user's auditory canals during an irrigation operation. For example, the discharge inlet port 919 may be configured to interface with one of the first and second earpieces 901a, 901b by way of a corresponding port, such as port 918b of the second over-ear earpiece 901b, as shown in FIG. 20B.

In some implementations, for example, the discharge inlet port 919 may include any suitable type of valve such as a check-valve, non-return valve, or the like, to receive, from one or both of the user's auditory canals, the applied fluid from one or more irrigation operations. The valve can be a one-way valve that allows fluid and/or substances to flow into the discharge reservoirs 930a, 930b, but prevents fluid and/or substances from flowing back out of the discharge reservoirs 930a, 930b. The received fluid may include, for example, a mixture or slurry composed of applied fluid and solids such as applied fluid having entrained excess ear wax dislodged from ear canal EC. Each discharge reservoir 930 may include a capacity sufficient to hold and contain the applied fluid from one or more irrigation operations along with any entrained substances. In some implementations, each discharge reservoir 930 may include the pressure relief port 997. The pressure relief port 997 may be configured to equalize or reduce pressure within each discharge reservoir 930, such as during receipt by each discharge reservoir 930 of the applied fluid during an irrigation operation. The pressure relief port 997 may include, for example, any suitable relief valve, pressure relief valve, or the like, that allows air within the discharge reservoirs 930a, 930b to exit to avoid pressure buildup within the discharge reservoirs 930a, 930 when fluid is flowing into the discharge reservoirs 930a, 930b but prevents fluid and/or substances received within the discharge reservoirs 930a, 930b from flowing out of the discharge reservoirs 930a, 930b. In some embodiments similar to those described above, the irrigation device 900 can include a vacuum assembly (e.g., a vacuum assembly 126), and the vacuum assembly can be in fluid communication with the pressure relief port 997 such that it can generate a negative pressure within the discharge reservoirs 930a, 930b to draw fluid and/or substances into the discharge reservoirs 930a, 930b (e.g., from the user's ear via the delivery elements 910a, 910b).

In some implementations, each discharge reservoir 930 may be reusable. For example, in some implementations, each discharge reservoir 930 may be configured to contain the received fluid from the user's auditory canals for later disposal by release of the contained fluid from the discharge release port 934, e.g., after completion of an irrigation or cleaning operation. Alternatively, in some implementations, each discharge reservoir 930 can be disposable. For example, in some implementations, the discharge reservoirs 930 may be made partially or entirely of disposable and/or recyclable materials. Accordingly, in such implementations, each discharge reservoir 930 may be disposed of along with contained fluid from one or more irrigation operations. In some embodiments, each discharge reservoir 930a, 930b can be designed for single-use and disposal. For example, each discharge reservoir 930a, 930b can include valves that seal off access to an interior of the discharge reservoir 930a, 930b such that once the discharge reservoir 930a, 930b is filled with fluid and/or entrained substances, the discharge reservoir 930a, 930b should be replaced with a new discharge reservoir 930a, 930b.

In some implementations, the discharge reservoirs 930a and 930b may be configured to couple to a corresponding one of the earpieces 901a and 901b. For example, in some implementations, the discharge reservoirs 930 may be configured for removable attachment and detachment to and from a corresponding one of the earpieces 901, such as by way of the first and second coupling elements 993, 995, as shown in FIGS. 21A-21C. In some implementations, the first and second coupling elements 993, 995 may include, for example, mating features such as lateral or cantilevered projections, configured to removably mate and attach to corresponding mating structures of the earpieces 901, such as by interference or friction-fit, and the like. The mating structures of the earpieces 901 may include, for example, recesses or depressions configured to receive the mating structures of the first and second coupling elements 993, 995. The discharge reservoirs 930a, 930b can be attached to the earpieces 901a, 901b by pushing or pressing the discharge reservoirs 930a, 930b such that the coupling elements 993, 995 lock into the corresponding recesses in the earpieces 901a, 901b. The discharge reservoirs 930a, 930b can be removed from the earpieces 901a, 901b by moving the coupling elements 993, 995 (e.g., by pushing on the release tabs).

In some implementations, each discharge reservoir 930 may include respective earpiece correspondence indicia 936, such as earpiece correspondence indicia 936, as shown in FIG. 21C. Similar to that described with reference to FIG. 20B, the earpiece correspondence indicia 936 may be configured to indicate to a user with which earpiece 901 each discharge reservoir 930 may be respectively configured to interface. For example, as shown in FIG. 21C, the earpiece correspondence indicia 936 can include the text "L" to indicate that the particular discharge reservoir 930a, 930b corresponds the earpiece 901a, 901b including a similar indicia (e.g., the text "L"). Generally, the earpiece correspondence indicia 936 of each discharge reservoir 930a, 930b may include any indicia or markings suitable to enable or facilitate user confirmation of correct installation of components of the irrigation device 900, such as by visual, haptic, and/or other perception of the indicia by a user, in accordance with the present disclosure.

In some implementations, each discharge reservoir 930 may be configured for fluid communication with a respective cannula 910 by way of a respective cannula coupler interface (e.g., a coupling 105). Moreover, respective fluid communication paths (e.g., a discharge path 118) may be configured to connect each discharge reservoir 930 to a respective cannula 910 to establish and maintain fluid communication therebetween. For example, when an irrigation procedure begins, applied cleaning agent may be discharged from one or both ear canals EC through a nozzle inlet of a respective cannula 910 to proceed through and along the fluid communication path towards one or both of the discharge reservoirs 930 for containment and later disposal.

As an example, one or more vacuum assemblies (e.g., vacuum assembly 126) may be coupled to the discharge reservoirs 930 to move the applied cleaning agent from the ear canal EC of the user through and along respective fluid communication paths to the discharge reservoirs 930 by application of negative pressure, vacuum, suction, or the like. The negative pressure may be applied, for example, to the volumes of one or both of the discharge reservoirs 930 in which the applied cleaning agents are to be contained (e.g., for later disposal). In some implementations, for example, the one or more vacuum assemblies may include a vacuum or suction pump configured to draw applied cleaning agent from the ear canal EC at a preset pressure and/or flow rate.

In some embodiments, additional openings or ports (not depicted) may be provided along an inner surface of the earsets 901a, 901b that can capture and/or draw fluid that leaks out of the user's ear and/or delivery elements 910a, 910b into the cavities 933a, 933b. These additional openings can be disposed along a bottom portion of the cavities 933a, 933b and can be fluidically coupled to respective discharge reservoirs 930a, 930b (e.g., via a discharge path, such as discharge path 118), such that fluid captured in the openings can be received within the discharge reservoirs 930a, 930b to later disposal. In some embodiments, a vacuum assembly (e.g., vacuum assembly 126) can be used to generate a negative pressure that draws fluid into the openings and into the discharge reservoirs 930a, 930b.

In some embodiments, instead of two discharge reservoirs 930a, 930b, a single discharge reservoir can be provided for receiving fluid from one or two earsets 901a, 901b. The single discharge reservoir can be attached to one of the two earsets 901a, 901b, and/or attached to another portion of the irrigation device 900 (e.g., along a length of head band 903), and fluidically coupled to the delivery elements 910a, 910b and/or other openings along the cavities 933a, 933b (as described above) to receive fluid from the user's ear (e.g., auricle AR and/or ear canal EC). In such embodiments, the discharge reservoir can be sufficiently size to contain fluid applied to two ears of a user.

Figure 21D:
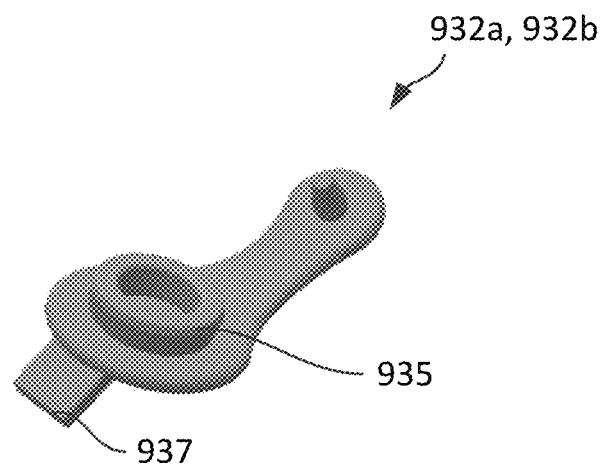
FIGS. 21D and 21E are various views of a cap for a discharge reservoir of the ear cleaning or irrigation device depicted in FIG. 18, according to an embodiment.
Figure 21E:
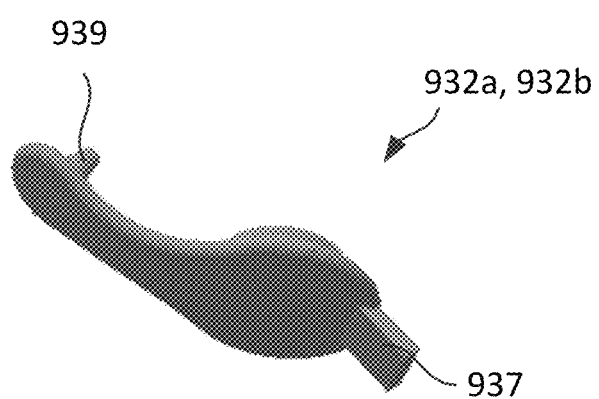

As depicted in FIG. 18, caps 932a, 932b can be used to cover port 934 of each discharge reservoir 930a, 930b. FIGS. 21D and 21E provide a detailed view of caps 932a, 932b. Each cap can include an annular protrusion 935 that can mate with port 934 of each discharge reservoir 930a, 930b to form a seal that prevents fluid and/or substances within discharge reservoir 930a, 930b from exiting discharge reservoir 930a, 930b via port 934. Caps 932a, 932b can include a tab 937 that can be pulled to decouple protrusion 935 from port 934, thereby releasing the seal and allowing fluid and/or substances within discharge reservoirs 930a, 930b to drain out of discharge reservoirs 930a, 930b. In some embodiments, when caps 932a, 932b are moved aside to expose port 934, a fluid channel (not depicted) can be coupled to the port 934 to drain fluid from within the discharge reservoir 930a, 930b. An external vacuum source (not depicted) optionally can be coupled via port 934 to discharge reservoir 930a, 930b to suction out fluid and/or substances within discharge reservoir 930a, 930b. Caps 932a, 932b can also include a protrusion 939 that further secures the caps 932a, 932b to the discharge reservoirs 930a, 930b, e.g., via a friction fit between protrusion 939 with a correspondingly shaped recess 936 formed in discharge reservoir 930a, 930b.

Figure 23A:
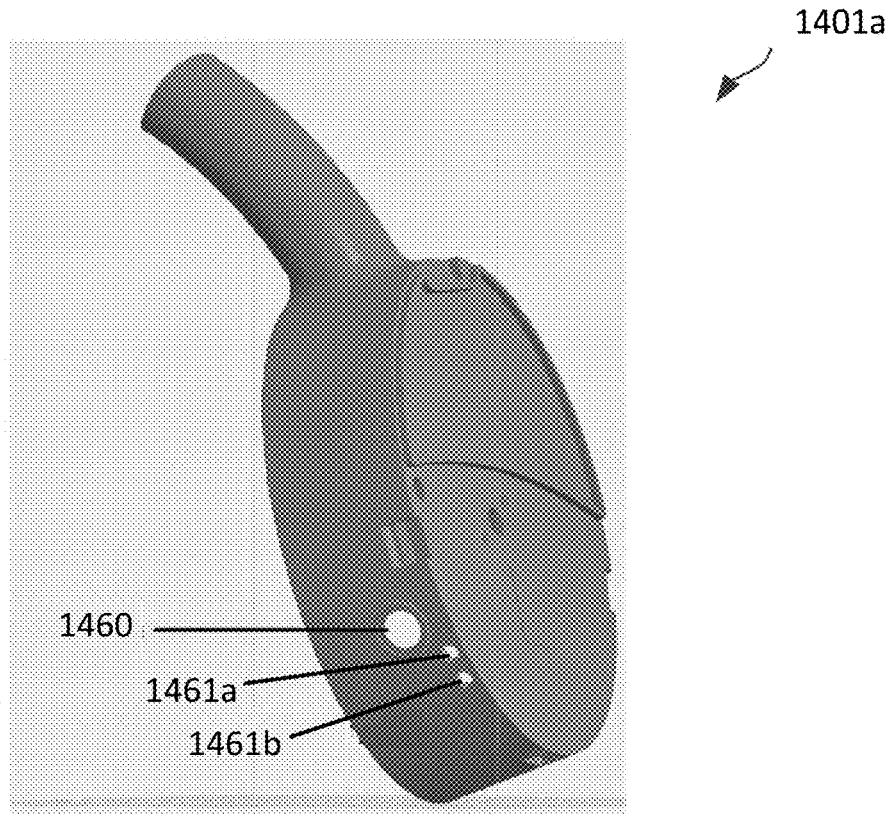
FIGS. 23A and 23B are perspective views of a first and second earset of an ear cleaning or irrigation device, according to an embodiment.
Figure 23B:
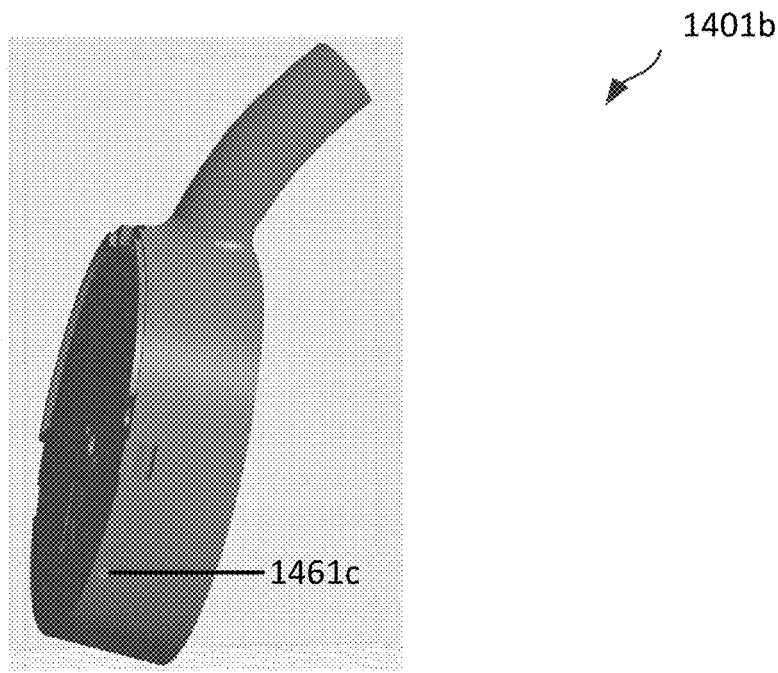

The user interface 960 can be used to operate the irrigation device 900. In an embodiment, the user interface 960 can include a button that can be pressed one or more times to operate the irrigation device 900. For example, the button can be pressed a first time to power on the irrigation device 900. When the irrigation device 900 powers on, one of the earsets 901a, 901b can be automatically selected for the cleaning procedure. A visual indicator 961a, 961b (e.g., light) (depicted in FIG. 18) can illuminate and/or an audio indicator can sound a noise indicating which earset 901a, 901b has been selected for the cleaning procedure. If the user desires to select a different earset 901a, 901b and/or both earsets 901a, 901b, then the user can press the button one or more additional times until the appropriate visual indicators 961a, 961b corresponding to the desired earsets 901a, 901b are selected. The user can then press the button, e.g., for an extended period of time, to initiate the cleaning procedure in the selected earsets 901a, 901b. In some embodiments, an irrigation device (e.g., irrigation device 100, 200, etc.) can include one or more indicators, such as visual, audio, or other types of indicators, to indicate an operational status of the irrigation device, such as whether the irrigation device is powered on, whether a particular earset of the irrigation device is selected for operation, or another status of the irrigation device (e.g., whether components have been properly attached, whether fluid is present in the fluid reservoir and/or discharge reservoir, etc.). For example, FIGS. 23A and 23B depict perspective views of first and second earsets 1401a and 1401b of an irrigation device, including various user interface components. In some implementations, the user interface components may include, for example, an I/O element 1460 and indicators 1461a, 1461b, and 1461c. As an example, indicator 1461a may be a visual indicator that is configured to be illuminated to indicate to a user a power status (e.g., an on/off status) of the irrigation device, indicator 1461b may be a visual indicator configured to indicate to the user that the first earset 1401a is selected (e.g., to perform a cleaning procedure or irrigation operation, etc.), and visual indicator 1461c may be configured to indicate to the user that the second earset 1401b is selected (e.g., to perform a cleaning procedure or irrigation operation, etc.). In some embodiments, indicators 1461a, 1461b, 1461c can be visual indicators that illuminate in response to other detected or sensed information, e.g., whether a fluid reservoir or discharge reservoir has been installed, whether fluid is present in a fluid reservoir or discharge reservoir, whether the fluid in an installed fluid reservoir is of an appropriate temperature, etc. Such information can be detected, for example, via one or more sensors (e.g., light sensors, pressure sensors, temperature sensors).

FIGS. 22A-22F are various views of the first and second delivery elements 910a and 910b of the ear cleaning or irrigation device 900, according to an embodiment. As shown, each delivery element 910 may include an inlet port implemented as an irrigation flow path 912 in fluid communication with one or more irrigation outlet apertures 912a, a discharge port implemented as a discharge flow path 914 in fluid communication with a discharge collection inlet port 914a, one or more coupling elements 916, and earpiece correspondence indicia 918.

In some implementations, each delivery element 910 may include a body disposed about a central axis 902. The body may be defined by a distal end and a proximal end, separated by a length of the body. As shown, the body may taper (e.g., linearly or non-linearly) from the proximal end towards the distal end, such that a cross-sectional area of the proximal end is greater than a cross-sectional area of the distal end, to facilitate safe and/or controlled insertion into the user's auditory canal. The body of each delivery element 910 may include portions that have different tapering profiles, e.g., to form curves, steps, etc. along a length of the delivery element 910. In some implementations, the body of each delivery element 910 may be formed of a unitary or monolithic material, e.g., have a single-piece construction. In some implementations, the body of each delivery element 910 may otherwise be formed of a plurality of pieces, such as may be joined by welding, adhesive, or the like. In some implementations, the central axis 902 may correspond to an axis of revolution about which the body of each delivery element 910 may be defined.

The coupling elements 916 are configured to facilitate coupling between the delivery elements 910a, 910b and the respective earsets 901a, 901b. The coupling elements 916, for example, can latch into a rib, projection, or other corresponding structure of the earsets 901a, 901b, to couple the delivery elements 910a, 910b to the respective earsets 901a, 901b. When coupled to the earsets 901a, 901b, the irrigation flow path 912 can be fluidically coupled, e.g., via an inlet path, to a fluid reservoir 920a, 920b and the discharge flow path 914 can be fluidically coupled, e.g., via a discharge path, to a discharge reservoir 930a, 930b.

As depicted, the irrigation flow path 912 can extend a greater length than the discharge flow path 914. At a proximal end of the delivery elements 910a, 910b, the discharge flow path 914 can be disposed around the irrigation flow path 912. At a distal end of the delivery elements 910a, 910b, the irrigation flow path 912 and the discharge flow path 914 can be radially offset from one another and radially offset from the central axis 902 of the delivery element 910a, 910b. For example, the irrigation flow path 912 can be disposed above the central axis 902 of the delivery element 910a, 910b, while the discharge flow path 914 can be disposed below the central axis 902 of the delivery element 910a, 910b. Such relative positioning of the irrigation flow path 912 and the discharge flow path 914 can be beneficial for delivering fluid into a user's ear canal and receiving fluid from the user's ear canal when the user is in an upright position, e.g., since fluid entering the ear from the irrigation outlet apertures 912a can flow from an upper portion of the ear canal to a lower portion of the ear canal via gravity and then travel out of the ear canal via the discharge collection inlet port 914a.

Figure 22A:
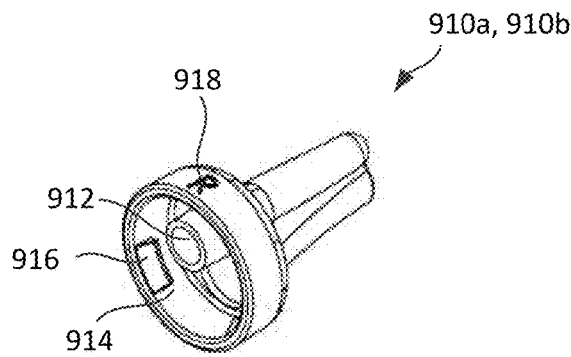
FIGS. 22A-22F are various views of delivery elements of the ear cleaning or irrigation device depicted in FIG. 18, according to an embodiment.
Figure 22B:
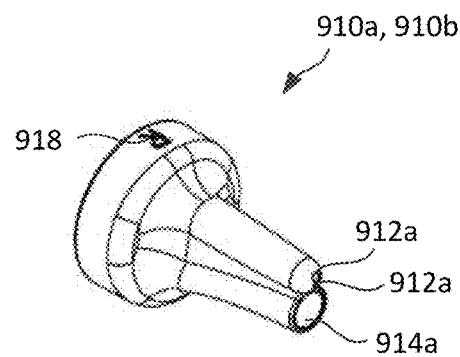
Figure 22C:
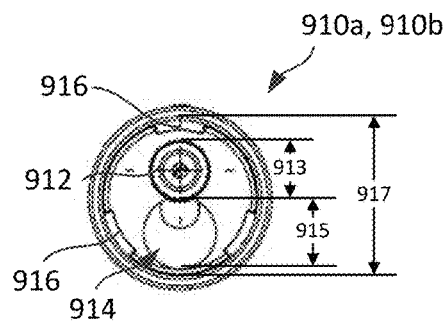
Figure 22D:
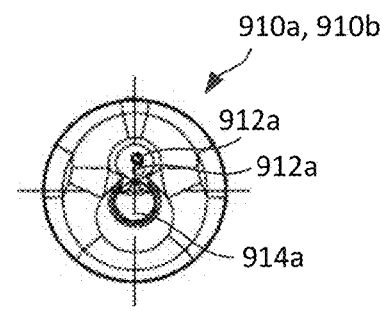
Figure 22E:
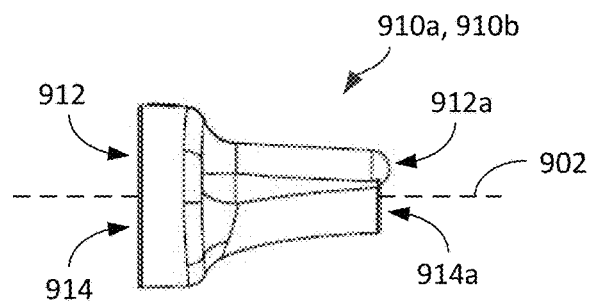
Figure 22F:
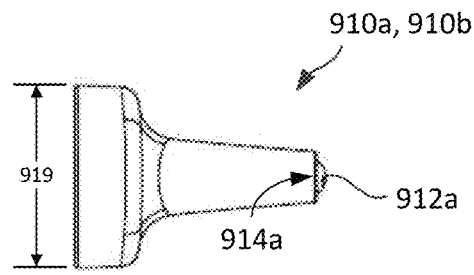

FIGS. 22E and 22F depict the relative arrangements of the irrigation outlet apertures 912a and the discharge collection inlet port 914a along a longitudinal length of the delivery elements 910a, 910b. As depicted, the one or more irrigation outlet apertures 912a are disposed distal to the discharge collection inlet port 914a. By being disposed distal to the discharge collection inlet port 914a, the one or more irrigation outlet apertures 912a can be better positioned to direct fluid into the ear canal without having that fluid be drawn into the discharge collection inlet port 914a before making contact with portions of the ear canal and/or substances within the ear canal (e.g., ear wax) to dislodge and remove those substances from the ear canal. Accordingly, the more distal positioning of the irrigation outlet apertures 912a can enable more efficient and effective cleaning of the ear canal, e.g., with less fluid being drawn into the discharge collection inlet port 914a without first being applied to the ear canal.

In the embodiment as shown, each delivery element 910a, 910b includes a plurality of irrigation outlet apertures 912a. The plurality of irrigation outlet apertures 912a can be directed at different angles with respect to the central axis 902 of the delivery elements 910a, 910b such that fluid and/or cleaning agent can exit the irrigation outlet apertures 912a at different directions into the ear canal, e.g., to contact and/or clean different regions of the ear canal. In some embodiments, the plurality of irrigation outlet apertures 912a can have similar size and/or shape. In other embodiments, each outlet aperture 912a can have a different size and/or shape, e.g., to generate different fluid steams have different shape and/or profiles.

The irrigation flow path 912 and/or the discharge flow path 914 can change in diameter along a length of the delivery element 910a, 910b. For example, the discharge flow path 914 can include a first portion have a larger diameter 917 and a second portion having a smaller diameter 915. The smaller diameter portion can taper (e.g., further decrease in diameter) in a direction toward the distal end of the delivery element 910a, 910b. The irrigation flow path 912 can have a diameter 913 that tapers (e.g., decreases in diameter) from the proximal end to the distal end of the delivery element 910a, 910b.

To facilitate coupling of the delivery elements 910a, 910b to their respective earsets 901a, 901b, each delivery element 910a, 910b can be marked with an indicia 918. The indicia 918 can be disposed along a top surface of each delivery element 910a, 910b such that a user can know which orientation to position the delivery element 910a, 910b when coupling the delivery element 910a, 910b to the respective earsets 901a, 901b. The indicia 918 can also inform a user of which earset 901a, 901b the delivery element 910a, 910b is configured for coupling thereto. For example, as depicted in FIG. 22B, the indicia 918 can include the text "R" to indicate that the delivery element is to couple to the earset 901a, 901b with the corresponding text "R" or another indicia suggesting that the two are for the same ear of a user. Each delivery element 910a, 910b can be specifically designed for a right or a left ear, and he indicia 918 can used to indicate to a user which ear the delivery element 910a, 910b is designed for.

The delivery elements 910a, 910b can be sized and/or otherwise configured for different users, e.g., children, adults, etc. In a kit or assembly set, as further described below with reference to FIG. 23, multiple sizes of delivery elements 910a, 910b can be provided, and a physician can determine the appropriate size of delivery element 910a, 910b to use with a particular patient. Each delivery element 910a, 910b can have coupling elements 916 that are configured to couple to corresponding structure on the earsets 901a, 901b, regardless of its size. For example, different sized delivery elements 910a, 910b can have proximal ends that are substantially similar for coupling to earsets 901a, 901b but distal ends that are sized for insertion into different sized ear canals. In some embodiments, other components of the irrigation device 900 can also be sized for different patients. For example, annular membranes 922a, 922b can be sized to define cavities with different depths and/or diameters, e.g., to accommodate different sized ears and/or provide a more secure fit around an ear (e.g., having thicker annular membranes to provide a closer fit around a smaller ear).

Figure 22G:
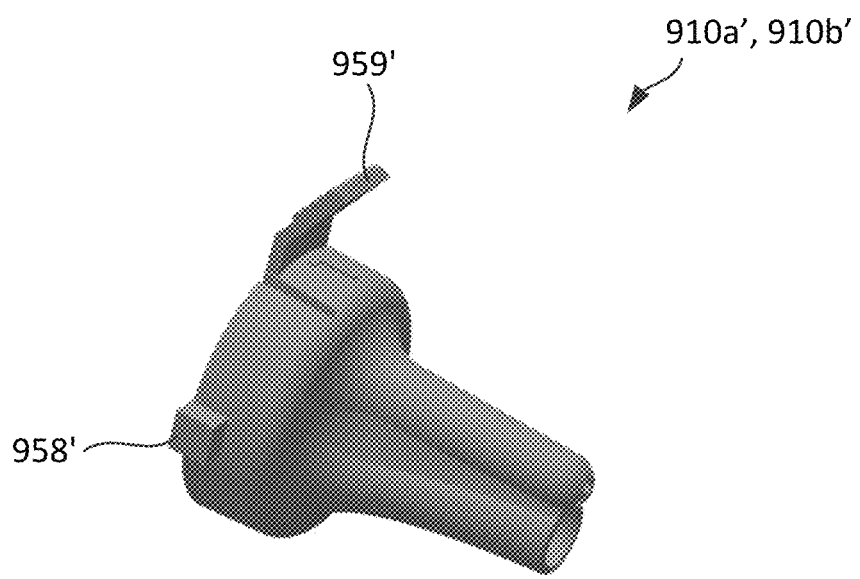
FIG. 22G is a perspective view of alternative delivery elements of an ear cleaning or irrigation device, according to an embodiment.

In some embodiments, a delivery element (e.g., delivery element 910a or 910b) can include an attachment or removal element. For example, as depicted in FIG. 22G, a delivery element 910a', 910b' can include a tab 959' that can be used to ensure proper attachment and/or to remove the delivery element 910a', 910b' from an earset (e.g., earset 901a, 901b) after use.

For example, the tab 959' may be configured to facilitate removal of each delivery element 910a', 910b' such as for replacement, maintenance, cleaning, and the like. In some embodiments, the delivery element 910a', 910b' may be disposable and/or recyclable. Accordingly, the tab 959' can be used to remove the delivery element 910a', 910b' after use. In some embodiments, the tab 959' can be designed to deform a proximal end of the delivery element 910a', 910b' such that the delivery element 910a', 910b' cannot be a used a second time, e.g., to prevent multiple uses of a disposable delivery element 910a', 910b'.

Additionally or alternatively, the tab 959' and/or other structure can ensure proper attachment of the delivery elements 910a', 910b' to their respective earsets (e.g., earsets 901a, 901b). For example, the tab 959' can indicate to a user the proper orientation of a delivery element 910a', 910b' relative to the earset when a user is attaching the delivery element 910a', 910b' to the earset. Additionally or alternatively, the delivery element 910a', 910b' can include structure (e.g., a protrusion 958' and/or tab 959') that can prevent the delivery element 910a', 910b' from being attached to the wrong earset (e.g., prevent a left delivery element from being attached to a right earset, or prevent a right delivery element from being attached to a left earset). For example, a protrusion 958' and/or tab 959' can be configured to fit into a slot or like structure on its corresponding earset, thereby ensuring proper attachment of the delivery elements 910a', 910b' to the earsets, e.g., ensuring that delivery elements 910a' 910b' configured for a right or left ear are attached to the corresponding earset for the right or left ear while preventing their attachment to the earset for the opposite ear.

Figure 24A:
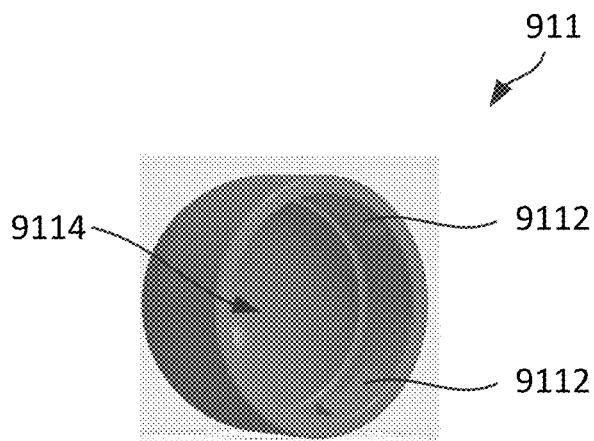
FIGS. 24A and 24B provide different perspective views of a component for cleaning an ear cleaning or irrigation device, according to an embodiment.
Figure 24B:
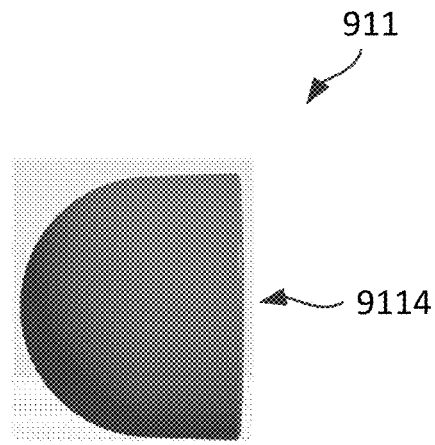

FIGS. 24A and 24B illustrate a component 911 for cleaning an ear cleaning or irrigation device (e.g., irrigation device 900, or any other irrigation devices described herein). The cleaning component 911 can be configured to cover a delivery element (e.g., delivery element 910a, 910b, or any other delivery elements described herein), such that it can direct fluid flow from an inflow channel (e.g., inlet path 116) out through an outflow channel (e.g., discharge path 118). A cleaning fluid (e.g., a liquid including a cleaning agent) can be cycled through the irrigation device, e.g., via the inflow channel and outflow channel, to clean the inflow channel and the outflow channel. The cleaning component 911 can be implemented in the form of a cap that defines a recess 9114. During a cleaning procedure, the irrigation device can be set deliver fluid into the recess 9114, e.g., via an inlet port of the delivery element, and receive fluid from the recess 9114, e.g., via an outlet port of the delivery element, to clean the inflow and outflow channels. The cleaning component 911 can include one or more coupling elements 9112 for facilitating coupling between the cleaning component 911 and the delivery element and/or another part of the irrigation device. The coupling elements 9112 can be, for example, ribs, flanges, projections, or similar structure for latching onto a complementary structure of the delivery element (or other component of the irrigation device, e.g., when the delivery element is not attached) or for forming a friction fit with a surface of the delivery element (or other component of the irrigation device). The cleaning components 911 can have any general shape and/or structure, including, for example, a dome-like or rounded shape, as shown in FIG. 24B.

Figure 25:
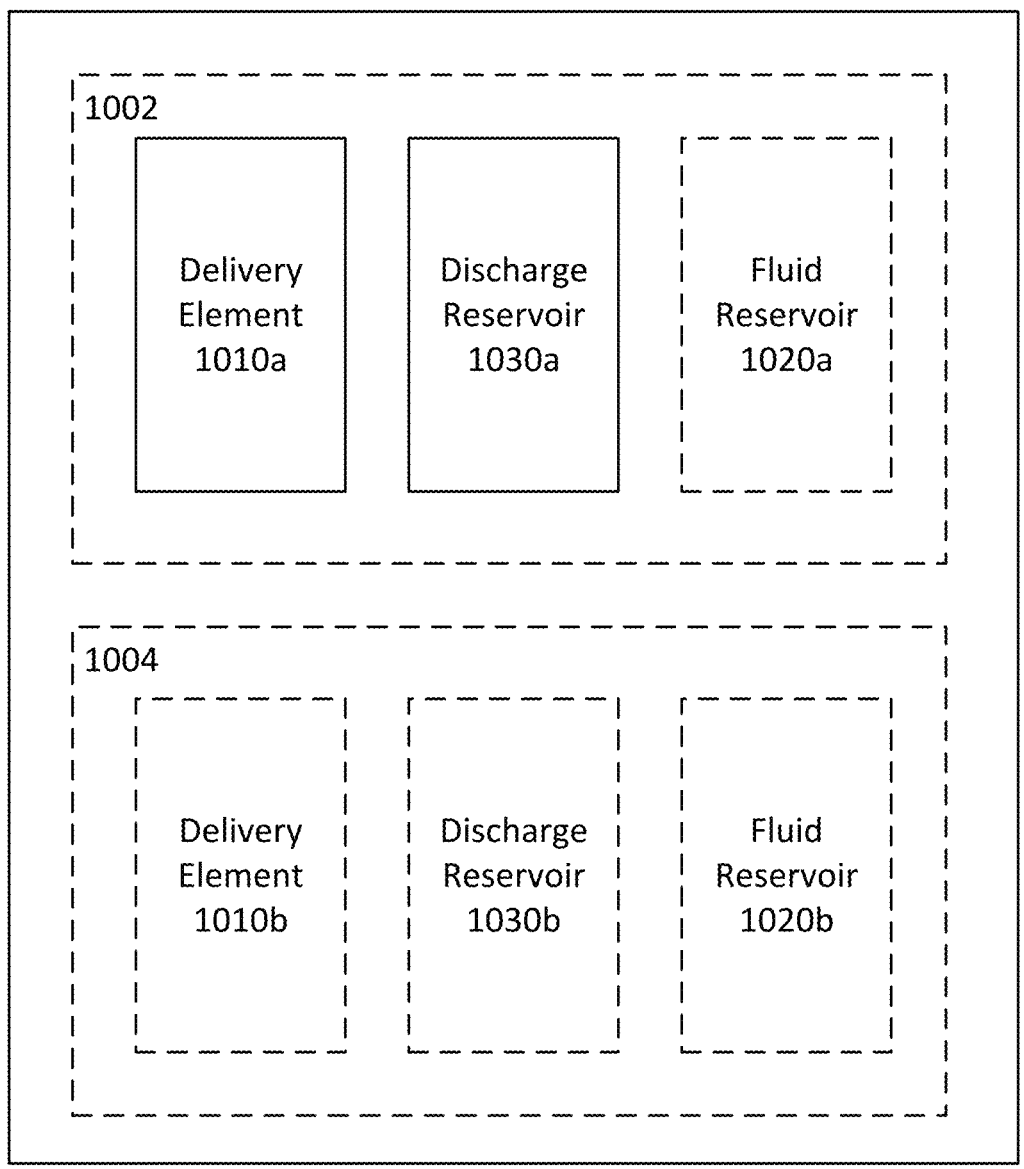
FIG. 25 is a schematic diagram depicting a packaging of disposable components of an ear irrigation device, according to an embodiment.

FIG. 25 is a schematic diagram depicting an ear cleaning kit 1000 for an irrigation or cleaning device, according to an embodiment. Ear cleaning kit 1000 may include replacement and/or disposable components of an ear cleaning device, such as a delivery element 1010a and a discharge reservoir 1030a. Optionally, ear cleaning kit 1000 may further include replacement and/or disposable components such as a fluid reservoir 1020a, and/or a second set of components, e.g., a delivery element 1010b, a discharge reservoir 1030b, and/or a fluid reservoir 1020b. In some implementations, one or more components of ear cleaning kit 1000 can be packaged within packaging elements 1002 and/or 1004 (e.g., sterile rigid or flexible bags, containers, or other suitable structure). For example, a first set of components including delivery element 1010a, discharge reservoir 1030a, and/or fluid reservoir 1020a can be packaged within a first packaging element 1002, and optionally a second set of components including delivery element 1010b, discharge reservoir 1030b, and/or fluid reservoir 1020b can be package within a second packaging element 1004. Ear cleaning kit 1000 may otherwise include any other replacement and/or disposable part or component suitable for use with an ear cleaning or irrigation device and system (e.g., ear cleaning device 100, 200, or other ear cleaning devices described herein), in accordance with embodiments of the present disclosure.

Kit 1000 may include one or more replacement delivery elements 1010a, 1010b (e.g., to replace delivery elements 110, 210, or other delivery elements (e.g., cannulas) described herein), one or more replacement discharge reservoirs 1030a, 1030b (e.g., to replace discharge reservoirs 130, 230 or other discharge reservoirs described herein), and one or more replacement fluid reservoirs 1020a, 1020b (e.g., to replace fluid reservoirs 120, 220 or other fluid reservoirs described herein), respectively. For example, delivery element 1010a, discharge reservoir 1030a, and fluid reservoir 1020a may include replacement parts or components for replacing delivery element 110, discharge reservoir 130, and fluid reservoir 120, respectively, as shown in FIG. 1, after use of such components. In particular, one or more of delivery element 110, discharge reservoir 130, and fluid reservoir 120 can be a disposable component (e.g., for use with a single user), and after use disposed and replaced with one or more of delivery element 1010a, discharge reservoir 1030a, and fluid reservoir 1020a, respectively, for a second use of the ear cleaning device 100 (e.g., with a different user).

Packaging elements 1002 and 1004 may each respectively include an indication associated with a component of ear cleaning kit 1000 (e.g., one or more of delivery element 1010a, 1010b, discharge reservoir 1030a, 1030b, fluid reservoir 1020a, 1020b), corresponding to a designation of use of the associated component (e.g., with respect to a corresponding type of earset and/or in replacing a corresponding component of ear cleaning device 100 and/or 200, or other ear cleaning devices described herein). For example, in some implementations, packaging element 1002 may include information indicating the particular component within the packaging and/or specifications of those components (e.g., for right or left ear use, sizing information, type of material, etc.).

As another example, in some implementations, when a kit includes additional components such as a second delivery element 1010b, discharge reservoir 1030b, and/or fluid reservoir 1020b, packaging element 1004 may include use-designating indicia associated therewith, to indicate to a user that delivery element 1010b, discharge reservoir 1030b, and fluid reservoir 1020b may be designated or specified for use with a corresponding type of earset (e.g., ear cleaning device 100, or earset 201b of ear cleaning device 200 such as a right earset). Generally, packaging elements 1002 or 1004 may include any type of indication by which a designation of use of a component of ear cleaning kit 1000 may be made, such as in terms of general use and/or suitability to replace a corresponding component (e.g., of ear cleaning device 100, 200, etc.), in accordance with embodiments of the present disclosure.

In some embodiments, kit 1000 can include multiple delivery elements 1010a, 1010b that are sized and/or configured differently. For example, kit 1000 can include a first delivery element 1010a for use with a right ear and a second delivery element for use with a left ear. In such case, use-designating indicia provided, e.g., on a label, can indicate to a user whether the delivery element is for the right ear or the left ear. As another example, kit 1000 can include first and second delivery element 1010a, 1010b that are sized for different patient populations, e.g., children, adult, etc., and use-designating indicia can appropriately indicate such information to a user. In some embodiments, kit 1000 can include multiple delivery elements 1010a, 1010b made of different materials, e.g., to accommodate users with sensitivities to different materials, or to provide a reusable delivery element made of more durable material and a disposable delivery element made of less durable material.

Figure 26:
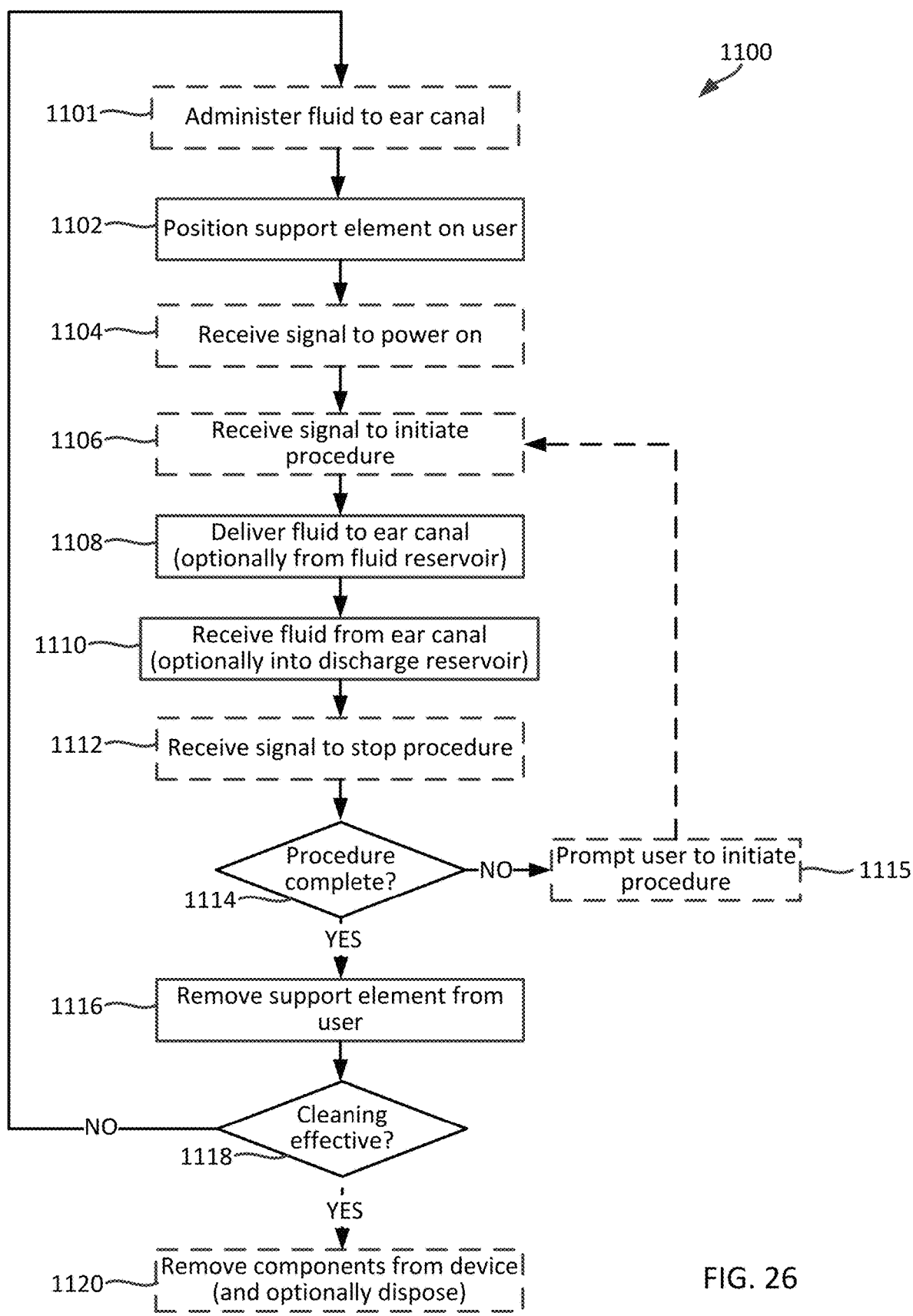
FIG. 26 is a flowchart depicting operational steps of a method of using an ear irrigation device, according to an embodiment.

FIG. 26 is a flowchart depicting operational steps of a method 1100 of using an ear cleaning device, according to an embodiment. The ear cleaning device may include any ear cleaning device (e.g., ear cleaning device 100 and/or 200) such as described herein.

At 1101, prior to positioning an irrigation device on a user, the user or another user (e.g., a physician) can optionally administer a fluid (e.g., cerumen softener) into the ear to soften and/or break down ear wax within the ear.

At 1102, a support element (e.g., support element 103) of the ear cleaning device (e.g., ear cleaning device 100) may be positioned on the user. For example, support element 103 may be positioned on the user near (e.g., adjacent to) auricle AR to mount delivery element 110 in ear canal EC.

At 1104, the method 1100 may optionally include receiving a signal to power on the ear cleaning device (e.g., ear cleaning device 100). For example, a processor (e.g., controller 150) may receive a signal (e.g., via I/O interface 160) corresponding to a request to power on the ear cleaning device.

At 1106, the method 1100 may optionally include receiving a signal to initiate an ear cleaning operation or procedure. For example, a processor (e.g., controller 150) may receive a signal (e.g., via I/O interface 160) corresponding to a request to initiate one or more ear cleaning operations (e.g., an irrigation operation, a discharge operation, etc.).

At 1108, a fluid (e.g., saline solution, cleaning fluid, cleaning agent, etc.) may be delivered to ear canal EC. For example, the fluid may be delivered under pressure to ear canal EC during an irrigation operation. Optionally, in some implementations, the fluid may be delivered to ear canal EC from a fluid reservoir (e.g., fluid reservoir 120) via a first fluid communication path (e.g., inlet path 116).

At 1110, a fluid composed of a mixture of dislodged and entrained excess ear wax may be received from ear canal EC. For example, the fluid may be removed and received from ear canal EC by discharge from ear canal EC through a discharge port (e.g., discharge port 114) during a discharge operation. Optionally, in some implementations, the second fluid may be received from ear canal EC for disposal in a discharge reservoir (e.g., discharge reservoir 130) via a second fluid communication path (e.g., discharge path 118).

At 1112, the method 1100 may optionally include receiving a signal to stop an ear cleaning operation or procedure. For example, the processor (e.g., controller 150) may receive a signal (e.g., via I/O interface 160) corresponding to a request to stop one or more ear cleaning operations (e.g., a previously initiated irrigation operation, a previously initiated discharge operation, etc.).

At 1114, the method 1100 may include determining whether an ear cleaning procedure is complete. For example, determining whether the ear cleaning procedure is complete may include determining, such as by a processor (e.g., of controller 150), that a current status of the ear cleaning procedure is set to complete, or the like. As another example, determining whether the ear cleaning procedure is complete may include determining, such as by a processor (e.g., of controller 150), that a current activity status (e.g., a pulsing cycle) of a fluid conveyance element (e.g., pump assembly 124 and/or vacuum assembly 126) is set to complete, or the like. As another example, determining whether the ear cleaning procedure is complete may include determining, such as by a processor (e.g., of controller 150), that a current pressurization status (e.g., of ear canal EC) is set to not pressurized, or the like. In some implementations, the ear cleaning device may be connected to and/or include one or more sensors (e.g., a pressure sensor, a temperature sensor, an image sensor, etc.), and determining whether the ear cleaning procedure is complete may include determining, such as by a processor (e.g., of controller 150), that a current status of the ear cleaning procedure is complete based on data from one or more of the sensors. As another example, determining whether the car cleaning procedure is complete may include determining, such as by a processor (e.g., of controller 150), that a current status of the ear cleaning procedure is complete based on user input (e.g., received via I/O interface 160). The user input may be received from a user based on a manual check or determination by the user of the current status of the ear cleaning procedure. In response to determining the ear cleaning procedure is complete, the method 1100 may proceed to 1115. In response to determining the ear cleaning procedure is not complete, the method 1100 may proceed to 1116.

At 1115, the method 1100 may optionally include prompting a user to initiate an ear cleaning operation or procedure. For example, the user may be prompted by way of a user interface (e.g., I/O interface 160) to receive a signal corresponding to a request to initiate the ear cleaning operation or procedure, such as described with reference to 1106. Accordingly, upon prompting the user, the method 1100 may proceed to 1106 and a cleaning procedure may initiate again.

At 1116, the support element (e.g., support element 103) of the ear cleaning device (e.g., the ear cleaning device 100) may be removed from the user. For example, support element 103 may be positioned off the user away from auricle AR after unmounting delivery element 110 from ear canal EC.

At 1118, the method 1100 may include determining whether the ear cleaning procedure was effective. For example, determining whether the ear cleaning procedure was effective may include determining, such as by a processor (e.g. of controller 150), whether an efficacy of the ear cleaning procedure meets or exceeds a predetermined threshold. The efficacy of the ear cleaning procedure may be determined, for example, based on user input corresponding to an efficacy result of a manual check by the user. The efficacy result may include, for example, low efficacy (e.g., cleaning not effective), moderate efficacy (e.g., cleaning potentially not effective), high efficacy (e.g., cleaning effective), and the like. In response to determining the ear cleaning procedure was not effective, the method 1100 may proceed back to Step 1102, where the ear cleaning device can be positioned back on a user. In response to determining the ear cleaning procedure was effective, the method 1100 may optionally proceed to 1120.

At 1120, the method 1100 may include removing one or more components from the ear cleaning device. The one or more components may include, for example, a fluid reservoir (e.g., fluid reservoir 120), a discharge reservoir (e.g., discharge reservoir 130), and/or a delivery element (e.g., delivery element 110). In some implementations, the method 1100 may also optionally include disposing of the one or more removed components (e.g., by the user). For example, each of the one or more components may be removed by detachment from the ear cleaning device, for replacement by a corresponding component.

Figure 27:
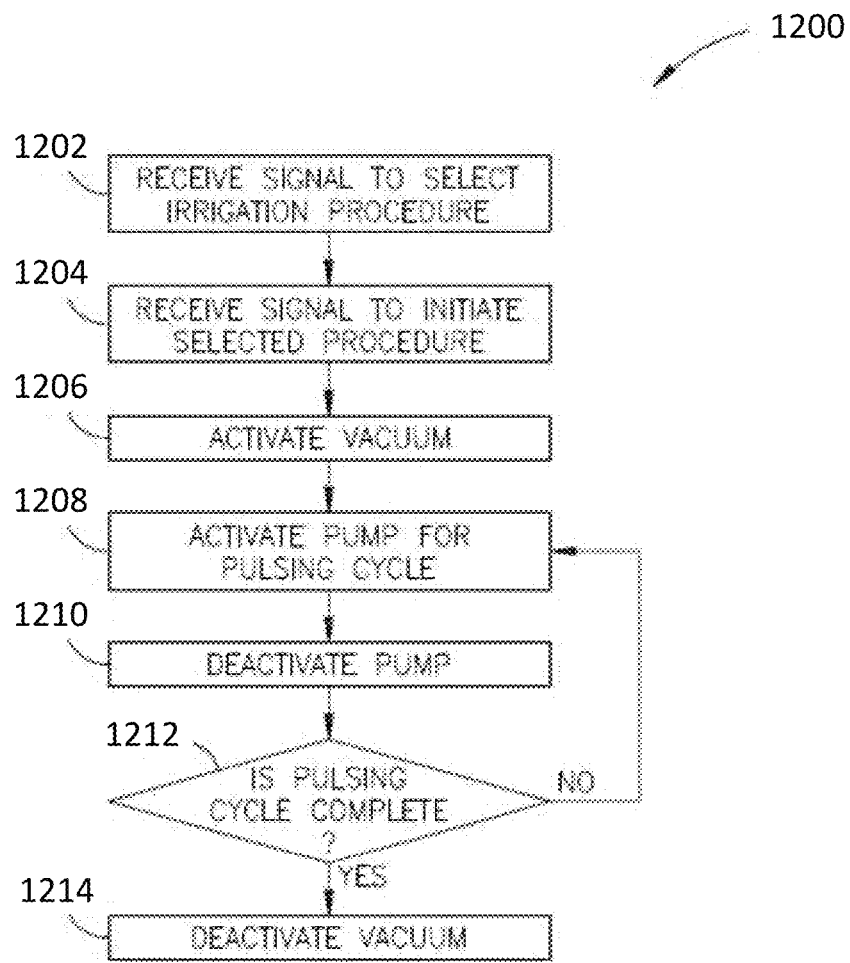
FIG. 27 is a flowchart depicting operational steps of a method of operating an ear irrigation device, according to an embodiment.

FIG. 27 is a flowchart depicting operational steps of a method 1200 of operating an cleaning device, according to an embodiment. The cleaning device may include any ear cleaning device or irrigation device such as described herein. At 1202, a signal is received that selects between various ear cleaning procedures (e.g., irrigation procedures and/or discharge procedures with different pulsing cycles, and the like) stored on one or more memories (e.g., a memory associated with a processor of the ear cleaning device, e.g., controller 150) of controller circuitry (e.g., controller circuitry such as controller 150). At 1204, a signal is received that initiates the currently selected irrigation procedure.

At 1206, a vacuum assembly (e.g., vacuum assembly 126) is activated via a signal generated by the controller circuitry (e.g., controller 150) and transmitted through a user or output interface (e.g., I/O interface 160 or other output interface). At 1208, a pump assembly (e.g., pump assembly 124) is activated for a pulsing cycle. As noted before, activating the pump assembly (e.g., pump assembly 124) results in a fluid or cleaning agent being dispensed from a cleaning agent reservoir (e.g., fluid reservoir 120) via a cleaning fluid fluidly communicative path (e.g., inlet path 116) towards a nozzle (e.g., of delivery element 110), where the cleaning agent can exit under pressure. Thus, sending the signal to activate the pump assembly (e.g., pump assembly 124) causes a certain quantity of a fluid or cleaning agent to be dispensed from the cleaning agent reservoir (e.g., fluid reservoir 120). Optionally, before activing the vacuum assembly and/or pump assembly, the cleaning device, e.g., via an audio output (e.g., speaker) can play a sound that informs the user that the vacuum and/or pumping is initiating.

At 1210, the pump assembly (e.g., pump assembly 124) is deactivated after a time-delay is observed, thus providing one pulse of cleaning agent. The time delay and resulting pulse duration may be up to 2 seconds, for example. In some implementations, the time delay may be more or less than 2 seconds. At 1212, a determination is made as to whether the pulse cycle is complete. If the pulse cycle is not complete, then the method 1200 may proceed back to 1208. If the pulse cycle is complete, then the method 1200 may proceed to 1214. In some implementations, each successive pulse may serve to soften and dislodge ear wax within the user's auditory canal. Each pulse cycle may be, for example, up to 30 seconds, one minute, 90 seconds, or longer. At 1214, the vacuum assembly (e.g., vacuum assembly 126) is deactivated to end the irrigation procedure. In some embodiments, the cleaning procedure including the pulsing and/or suctioning can be about 35 seconds (e.g., from 30-40 seconds). Optionally, after the irrigation or cleaning procedure is complete, the ear cleaning device can automatically power off.

Figure 28:
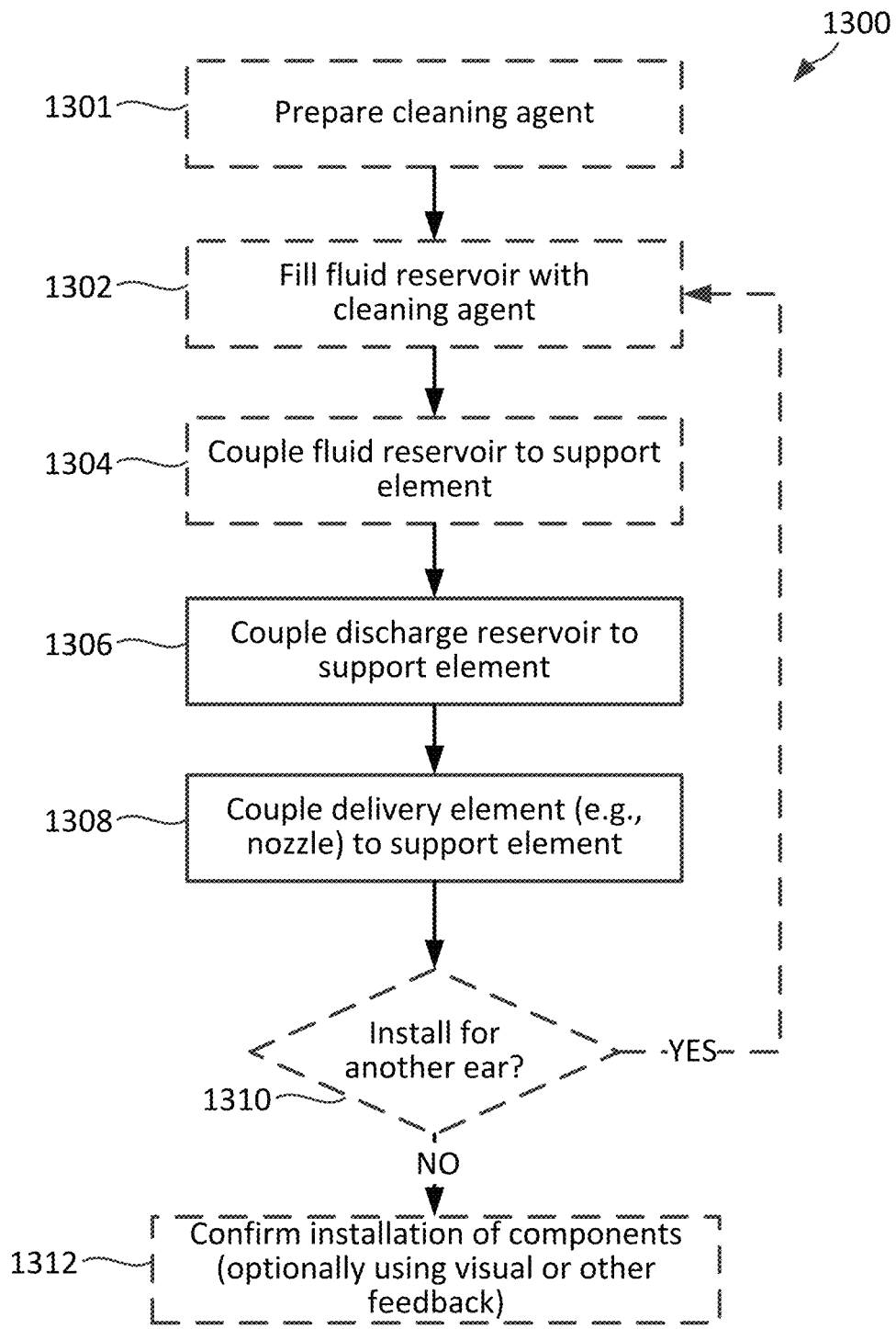
FIG. 28 is a flowchart depicting operational steps of a method of assembling an ear irrigation device, according to an embodiment.

FIG. 28 is a flowchart depicting operational steps of a method 1300 of assembling an ear cleaning device, according to an embodiment. The ear cleaning device may include any irrigation device or ear cleaning device such as described herein.

At 1301, a fluid (e.g., including a cleaning agent) can be prepared for use in an irrigation or cleaning procedure, such as described herein. The fluid can be prepared by mixing a fluid (e.g., a saline solution, water, etc.) with one or more of an anti-bacterial agent, an antibiotic agent, and the like. Additionally or alternatively, the fluid can be heated to a specific temperature (e.g., body temperature). In some embodiments, a fluid can be provided, e.g., in a kit (e.g., kit 1000) to a user for use in an irrigation procedure and therefore this step can be omitted.

At 1302, the method 1300 may optionally include filling a fluid reservoir (e.g., fluid reservoir 120) with a supply of fluid (e.g., fluid including a cleaning agent). In an embodiment, the supply of fluid can include approximately 70 milliliters of fluid.

At 1304, the method 1300 may optionally include coupling the fluid reservoir (e.g., fluid reservoir 120) to a support element (e.g., support element 103). At 1306, a discharge reservoir (e.g., discharge reservoir 130) may be coupled to the support element (e.g., support element 103). The fluid reservoir (e.g., fluid reservoir 120) and the discharge reservoir (e.g., discharge reservoir 130) may be coupled to the support element using any suitable attachment means, in accordance with embodiments of the present disclosure.

At 1308, a delivery element (e.g., delivery element 110) such as one having a nozzle, may be coupled to the support element (e.g., support element 103). The delivery element (e.g., delivery element 110) may be coupled to the support element (e.g., support element 103) using any suitable attachment means, in accordance with embodiments of the present disclosure.

At 1310, the method 1300 may optionally include determining whether an installation (e.g., of earset 201*b* in addition to earset 201*a*) for another ear is required. In response to determining the installation is required, the method 1300 may proceed back to 1302. In response to determining the installation is not required, the method 1300 may proceed to 1312. For example, determining whether an installation is required for another ear may include prompting the user for feedback (e.g., via user input) and making the determination based on the feedback.

At 1312, the method 1300 may optionally include confirming installation of one or more earsets (e.g., earset 201*b* and/or earset 201*a*). Optionally, in some implementations, the installation may be confirmed based on visual data (e.g., imaging data), acoustic data (e.g., ultrasound data), vibrational data (e.g., positional time-series data), or the like. For example, the installation may be confirmed with respect to an expected resonant frequency of the ear cleaning device for which installation of the one or more earsets may be known, determined, or otherwise confirmed. In some implementations, the ear cleaning device can include a sensor (e.g., a light sensor) that can confirm installation. In some implementations, the ear cleaning device can include physical indicia that enables a user to visually, haptically, and/or otherwise confirm installation.

Detailed embodiments of the present disclosure are disclosed herein for purposes of describing and illustrating claimed structures and methods that may be embodied in various forms, and are not intended to be exhaustive in any way, or limited to the disclosed embodiments. Many modifications and variations will be apparent to those of ordinary skill in the art without departing from the scope and spirit of the disclosed embodiments. The terminology used herein was chosen to best explain the principles of the one or more embodiments, practical applications, or technical improvements over current technologies, or to enable those of ordinary skill in the art to understand the embodiments disclosed herein. As described, details of well-known features and techniques may be omitted to avoid unnecessarily obscuring the embodiments of the present disclosure.

References in the specification to "one embodiment," "an embodiment," "an example embodiment," or the like, indicate that the embodiment described may include one or more particular features, structures, or characteristics, but it shall be understood that such particular features, structures, or characteristics may or may not be common to each and every disclosed embodiment of the present invention herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, structures and solutions associated with ear cleaning, including the various components and ratios of such components in cleaning solutions, have not been shown or described in detail to avoid unnecessarily obscuring descriptions of the implementations.

Unless the context requires otherwise, throughout the specification and claims which follow, the word "comprise" and variations thereof, such as "comprises" and "comprising," are to be construed in an open, inclusive sense, that is, as "including, but not limited to."

Reference throughout this specification to "one implementation" or "an implementation" means that a particular feature, structure or characteristic described in connection with the implementation or implementations is included in at least one implementation or implementations. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementation or implementations.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the implementations.

While the present disclosure has been shown and described with reference to certain exemplary embodiments thereof, it will be understood by those skilled in the art that various changes in form and details may be made therein without departing from the spirit and scope of the present disclosure, as defined by the appended claims and their equivalents. Therefore, the embodiments of present disclosure has been provided by way of example for purposes of illustration, and not limitation.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. An apparatus, comprising:
   a support structure including a coupling element detachably coupleable to a delivery element and defining a cavity configured to receive an ear of a subject;
   a first reservoir coupleable to the support structure and configured to contain a first volume of fluid;
   a first channel configured to provide fluid communication between the first reservoir and the coupling element such that the first volume of fluid can be delivered from the first reservoir to the coupling element;
   a vacuum assembly disposed in the support structure and fluidically coupled to a second reservoir, the vacuum assembly configured to draw fluid from the ear of the subject to the second reservoir via a second channel by generating a negative pressure in the second reservoir; and
   a second channel configured to provide fluid communication between the second reservoir and the coupling element such that the second volume of fluid can be received in the second reservoir from the coupling element.

2. The apparatus of claim 1, wherein the coupling element is a first coupling element, the delivery element is a first delivery element, the cavity is a first cavity, the ear is a first ear, and the support structure further includes a second coupling element detachably coupleable to a second delivery element and defines a second cavity configured to receive a second ear of the subject.

3. The apparatus of claim 2, wherein the support structure incudes:
   a first earpiece including the first coupling element;
   a second earpiece including the second coupling element; and
   an adjustable strap coupling the first earpiece to the second earpiece such that the first earpiece is spaced from the second earpiece, the adjustable strap disposable around a head of the subject such that the first ear of the subject is received in the first cavity and the second ear of the subject is received in the second cavity.

4. The apparatus of claim 1, further comprising:
   the second reservoir,
   wherein the second reservoir is detachably coupleable to the support structure.

5. The apparatus of claim 4, wherein the second reservoir includes at least one release tab movable to detach the second reservoir from the support structure.

6. The apparatus of claim 4, wherein the second reservoir includes:
   a first port configured to receive the second volume of fluid into the second reservoir;

a second port configured to couple to the vacuum assembly such that the vacuum assembly can generate a negative pressure within the second reservoir to draw the second volume of fluid into the second reservoir.

7. The apparatus of claim 6, wherein the second reservoir further includes a valve disposed in the first port that is configured to prevent the second volume of fluid from flowing out of the second reservoir via the first port.

8. The apparatus of claim 4, wherein the second reservoir further includes a cap movable between a first position in which the cap covers an opening of the second reservoir such that the second volume of fluid is contained within the second reservoir and a second position in which the cap separates from the opening such that the second volume of fluid can be discharged from the second reservoir via the opening.

9. The apparatus of claim 1, further comprising an annular membrane configured to form a portion of the cavity, the annular membrane configured to deform based on a shape of a head of the subject when the ear of the subject is received in the cavity.

10. The apparatus of claim 1, further comprising a pump assembly configured to pump the first volume of fluid along the first channel toward the coupling element.

11. The apparatus of claim 1, further comprising:
a pump assembly configured to pump the first volume of fluid along the first channel toward the coupling element.

12. The apparatus of claim 11, further comprising:
an input element actuatable to cause the processor to activate the at least one of the pump assembly or the vacuum assembly; and
a processor configured to control at least one of the pump assembly or the vacuum assembly.

13. The apparatus of claim 1, further comprising the delivery element,
the delivery element to which the coupling element is detachably coupleable, the delivery element including a body insertable into an ear canal of the subject and defining:
a first port configured to deliver the first volume of fluid into the ear canal; and
a second port configured to receive the second volume of fluid from the ear canal.

14. A kit, comprising:
a support structure including a housing, the support structure configured to receive an ear of a subject;
a delivery element coupleable to the housing of the support structure including:
a body insertable into an ear canal of a subject and defining:
a first port having at least one opening configured to deliver a first volume of fluid into the ear canal; and
a second port configured to receive a second volume of fluid from the ear canal, the second volume of fluid including a portion of the first volume of fluid and one or more particles of debris dislodged by the first volume of fluid;
the at least one opening of the first port disposed distal to a distal end of the second port such that, when the body is inserted into the ear canal, the first port extends a greater depth into the ear canal than the second port; and
a coupling element configured to detachably couple the delivery element to an irrigation device;
a vacuum assembly disposed in the housing of the support structure; and
a discharge collection reservoir coupleable to the housing of the support structure and in fluidic communication with the vacuum assembly via a pressure relief port integrated into the discharge collection reservoir, the discharge collection reservoir configured to receive the second volume of fluid from the second port.

15. The kit of claim 14, wherein the first port includes a plurality of apertures, each aperture from the plurality of apertures disposed at a different angle with respect to a central axis of the delivery element such that fluid exiting that aperture contacts a different area of the ear canal than the other apertures from the plurality of apertures.

16. The kit of claim 14, wherein a distal end of the first port is radially offset from a distal end of the second port.

17. The kit of claim 14, wherein at least one of the first port or the second port has a cross-sectional area that decreases along a length of the delivery element toward a distal end of the delivery element.

18. The kit of claim 14, wherein the delivery element further includes a filter disposed within the second port and configured to filter the second volume of fluid as the second volume of fluid flows through the filter such that particles from the one or more particles having a dimension larger than a preset value are filtered from the second volume of fluid.

19. The kit of claim 14, wherein the delivery element is a first delivery element and is configured for insertion into a left ear of the subject, the kit further comprising a second delivery element configured for insertion into a right ear of the subject.

* * * * *